United States Patent
Shailubhai et al.

(10) Patent No.: US 10,653,744 B2
(45) Date of Patent: May 19, 2020

(54) FORMULATIONS AND METHODS FOR TREATING ULCERATIVE COLITIS

(71) Applicant: Bausch Health Ireland Limited, Dublin (IE)

(72) Inventors: Kunwar Shailubhai, Audubon, PA (US); Gary S. Jacob, New York, NY (US); Patrick Griffin, New York, NY (US)

(73) Assignee: Bausch Health Ireland Limited, Dublin (IE)

( * ) Notice: Subject to any disclaimer, the term of this patent is extended or adjusted under 35 U.S.C. 154(b) by 0 days.

(21) Appl. No.: 16/069,313

(22) PCT Filed: Jan. 11, 2017

(86) PCT No.: PCT/US2017/013017
§ 371 (c)(1),
(2) Date: Jul. 11, 2018

(87) PCT Pub. No.: WO2017/123634
PCT Pub. Date: Jul. 20, 2017

(65) Prior Publication Data
US 2019/0030116 A1 Jan. 31, 2019

Related U.S. Application Data

(60) Provisional application No. 62/277,329, filed on Jan. 11, 2016.

(51) Int. Cl.
*A61K 38/12* (2006.01)
*A61K 9/00* (2006.01)
*A61K 38/10* (2006.01)
*A61P 1/04* (2006.01)

(52) U.S. Cl.
CPC ............ *A61K 38/12* (2013.01); *A61K 9/0031* (2013.01); *A61K 38/10* (2013.01); *A61P 1/04* (2018.01)

(58) Field of Classification Search
None
See application file for complete search history.

(56) References Cited

U.S. PATENT DOCUMENTS

| | | | |
|---|---|---|---|
| 7,041,786 B2 | 5/2006 | Shailubhai et al. | |
| 7,799,897 B2 | 9/2010 | Jacob et al. | |
| 7,879,802 B2 * | 2/2011 | Shailubhai | C07K 7/08 514/20.6 |
| 8,034,782 B2 | 10/2011 | Shailubhai | |
| 8,114,831 B2 | 2/2012 | Shailubhai et al. | |
| 8,207,295 B2 | 6/2012 | Shailubhai et al. | |
| 8,357,775 B2 | 1/2013 | Shailubhai et al. | |
| 8,367,800 B2 | 2/2013 | Shailubhai | |
| 8,497,348 B2 | 7/2013 | Shailubhai et al. | |
| 8,569,246 B2 | 10/2013 | Shailubhai | |
| 8,637,451 B2 | 1/2014 | Shailubhai et al. | |
| 8,664,354 B2 | 3/2014 | Shailubhai | |
| 8,716,224 B2 | 5/2014 | Shailubhai et al. | |
| 8,901,075 B2 | 12/2014 | Shailubhai et al. | |
| 8,969,514 B2 | 3/2015 | Shailubhai | |
| 9,089,612 B2 | 7/2015 | Shailubhai | |
| 9,914,752 B2 * | 3/2018 | Shailubhai | C07K 7/08 |
| 2003/0170223 A1 | 9/2003 | Ahmad | |
| 2010/0120694 A1 | 5/2010 | Shailubhai et al. | |
| 2010/0221329 A1 | 9/2010 | Shailubhai et al. | |
| 2012/0237593 A1 | 9/2012 | Comiskey et al. | |
| 2013/0210822 A1 | 8/2013 | Hangauer et al. | |
| 2013/0274204 A1 | 10/2013 | Shailubhai et al. | |
| 2014/0242124 A1 * | 8/2014 | Riff | A61K 38/10 424/400 |
| 2014/0287002 A1 | 9/2014 | Shailubhai | |
| 2016/0235807 A1 | 8/2016 | Shailubhai | |

FOREIGN PATENT DOCUMENTS

| | | |
|---|---|---|
| WO | WO 1999/066918 A1 | 6/2002 |
| WO | WO 2008/151257 A2 | 12/2008 |
| WO | WO 2010/065751 A2 | 6/2010 |
| WO | WO 2012/037380 A2 | 3/2012 |
| WO | WO 2012/118972 A2 | 9/2012 |
| WO | WO 2014/197720 A2 | 12/2014 |
| WO | WO 2015/054500 A2 | 4/2015 |
| WO | WO 2015/054649 A2 | 4/2015 |
| WO | WO 2017/123634 A1 | 7/2017 |

OTHER PUBLICATIONS

Beery et al. ("Current approaches to the management of new-onset ulcerative colitis," Clinical and Experimental Gastroenterology 2014:7 111-132) (Year: 2014).*
Lawrance ("Topical Agents for Idiopathic Distal Colitis and Proctitis," J Gastroenterol Hepatol. 2011;26(1):36-43) (Year: 2011).*
Heyman et al. ("Efficacy and Safety of Mesalamine Suppositories for Treatment of Ulcerative Proctitis in Children and Adolescents," Inflamm Bowel Dis. Nov. 2010; 16(11): 1931-1939) (Year: 2010).*
European Patent Application No. 14852901.9, Partial Supplementary European Search Report dated Mar. 22, 2017, 13 pages.
European Patent Application No. 14852901.9, Extended European Search Report dated Aug. 7, 2017, 16 pages.
International Application No. PCT/US2014/059914, International Preliminary Report on Patentability dated Apr. 12, 2016, 7 pages.
International Application No. PCT/US2014/059914, International Search Report and Written Opinion dated Apr. 7, 2015, 11 pages.
International Application No. PCT/US2017/013017, International Preliminary Report on Patentability dated Jul. 17, 2018, 6 pages.
International Application No. PCT/US2017/013017, International Search Report and Written Opinion dated Mar. 22, 2017, 10 pages.

(Continued)

*Primary Examiner* — Christina Bradley
(74) *Attorney, Agent, or Firm* — Saul Ewing Arnstein & Lehr LLP; Domingos J. Silva; Dennis Ostrovsky

(57) ABSTRACT

This invention provides composition and methods to prevent, treat or alleviate a symptom of ulcerative colitis comprising administering to a patient dolcanatide.

7 Claims, No Drawings
Specification includes a Sequence Listing.

(56) References Cited

OTHER PUBLICATIONS

Miller, et al., "Identification of Known Drugs that Act as Inhibitors of NF-κb Signaling and their Mechanism of Action." Biochem Pharmacol. (2010); 79 (9): 1272-1280.
Shailubhai, K., "Plecanatide and dolcanatide, novel guanylate cyclase-C agonists, ameliorate gastrointestinal inflammation in experimental models of murine colitis." World Journal of Gastrointestinal Pharmacology and Therapeutics (2015); 6 (4): 213-222.
Shailubhai, K., et al. "Guanylate Cyclase-C Agonists as a New Class of Drug Candidates to Delay Progression of Colitis to Colonic Tumors in Apc $^{min/+}$ Mice." Annu Sci Meet Am Coll Gastroenterol, Abstract P409, Oct. 28, 2011, Poster, 1 page.
Shailubhai, K., et al. "SP-333, A Guanylate Cyclase-C Agonist, Ameliorates DSS-Colitis in Mice via a Novel Cyclic GMP-Mediated Mechanism." P-198, Posters from the 2012 Advances in Inflammatory Bowel Diseases Crohn's & Colitis Foundation's National Clinical and Research Conference Dec. 13-15, 2012, Hollywood, Florida: Basic Science Poster presentation, Dec. 15, 2012, p. 1-1.

\* cited by examiner

FORMULATIONS AND METHODS FOR TREATING ULCERATIVE COLITIS

CROSS REFERENCE TO RELATED APPLICATIONS

This application is a U.S. National Phase of PCT/US2017/013017, filed Jan. 11, 2017, which claims the benefit of U.S. Provisional Application No. 62/277,329 filed Jan. 11, 2016, the contents of each of which are herein incorporated by reference in their entireties for all purposes

DESCRIPTION OF THE TEXT FILE SUBMITTED ELECTRONICALLY

The contents of the text file submitted electronically herewith are incorporated herein by reference in their entirety: A computer readable format copy of the Sequence Listing named "SYPA-015_N01US_SeqList_ST25.txt". The text file is about 105 kb, was created on Jul. 11, 2018, and is being submitted electronically via EFS-Web.

INCORPORATION BY REFERENCE OF SEQUENCE LISTING

The contents of the text file named "SYPA_015_001WO_SeqList_ST25.txt", which was recorded on Jan. 11, 2017 and is 105 KB in size, are hereby incorporated by reference in their entireties.

FIELD OF THE INVENTION

The present invention relates to the therapeutic use of guanylate cyclase C (GC-C) agonists the treatment of inflammatory bowel disease, such as, ulcerative colitis. The agonists may be used either alone or either concurrently or sequentially with additional active agents to prevent, treat or alleviate one or more symptoms of ulcerative colitis.

BACKGROUND OF THE INVENTION

Ulcerative colitis (UC) is an inflammatory bowel disease that primarily affects the colonic mucosa and sub-mucosa. The most common symptoms of ulcerative colitis are ulcers and inflammation of the inner lining of the colon that lead to symptoms of bloody diarrhea, passage of pus, mucus, and abdominal cramping during bowel movements. Currently, there is no effective therapy to cure the disease. As such, treatment mainly depends on reduction of the symptoms. Most people with mild or moderate ulcerative colitis are treated with corticosteroids (dexamethasone, prednisone, methylprednisone, and hydrocortisone) to reduce inflammation and relieve symptoms. Other drugs typically used to treat symptoms include immunomodulators (azathioprine and 6-mercapto-purine) and aminosalicylates. Many of these drugs are associated with numerous side effects. Dexamethasone, for example, has many side effects on liver and kidney functions.

A need exists for compositions and methods to treat, prevent and alleviate one or more symptoms of ulcerative colitis without side effects

SUMMARY OF THE INVENTION

The invention provides methods for preventing, treating, or alleviating a symptom of ulcerative colitis by rectally administering to a subject in need thereof a therapeutically effective amount of a composition comprising dolcanatide (i.e., SP-333 or SEQ ID NO: 9). The effective amount is between about 1 mg to 10 mg per dose. Preferably, the dose is 6 mg. The composition is administered once daily. Preferably, the composition is administered once daily for 28 days. The composition is administered prior to bedtime. The composition is administered as an enema or a suppository. Optionally, the release of the composition is time dependent. Also provided by the invention are formulations for rectal administration comprising the peptide of SEQ ID NO: 9, where said peptide is a (4,12:7,15) bicycle. The formulation is a liquid such as saline. Alternatively, the formulation is an enema or a suppository.

In another aspect the invention provides a rectal formulation comprising 6 mg of dolcanatide (SEQ ID NO: 9). The formulation is aqueous.

DETAILED DESCRIPTION

It should be understood that singular forms such as "a," "an," and "the" are used throughout this application for convenience, however, except where context or an explicit statement indicates otherwise, the singular forms are intended to include the plural. Further, it should be understood that every journal article, patent, patent application, publication, and the like that is mentioned herein is hereby incorporated by reference in its entirety and for all purposes. All numerical ranges should be understood to include each and every numerical point within the numerical range, and should be interpreted as reciting each and every numerical point individually. The endpoints of all ranges directed to the same component or property are inclusive, and intended to be independently combinable.

"About" includes all values having substantially the same effect, or providing substantially the same result, as the reference value. Thus, the range encompassed by the term "about" will vary depending on context in which the term is used, for instance the parameter that the reference value is associated with. Thus, depending on context, "about" can mean, for example, ±15%, ±10%, ±5%, ±4%, ±3%, ±2%, ±1%, or ±less than 1%. Importantly, all recitations of a reference value preceded by the term "about" are intended to also be a recitation of the reference value alone.

The present invention is based upon the development of agonists of guanylate cyclase-C (GC-C). The agonists are analogs of uroguanylin, guanylin, lymphoguanylin and E. coli ST peptide.

In particular the invention is based upon the discovery that rectal delivery of Dolcanatide (also referred to herein as SP-333 or SEQ ID NO:9) or Plecanatide (also referred to herein as SP-304 or SEQ ID NO:1) to ameliorate the symptoms of ulcerative colitis. Dolcanatide is an analog of uroguanylin with enhanced resistance to standard digestive breakdown by proteases in the intestine. It has been previously demonstrated in a number of preclinical models the potential anti-inflammatory role of uroguanylin and uroguanylin analogs in colitis. In these earlier animal studies, oral treatment with dolcanatide was shown to ameliorate DSS- and TNBS-induced acute colitis in murine models. Uroguanylin analog treatment was also shown to ameliorate spontaneous colitis in T-cell receptor alpha knockout mice, A double-blind, placebo-controlled, four-week study evaluating 28 patients with mild-to-moderate ulcerative colitis was conducted. Patients received 6 mg Dolcanatide dissolved in saline administered intra-rectally each evening for 28 days. Analysis of the data indicates clear signals of improvement in dolcanatide-treated patients compared with placebo-treated patients. In particular, dolcanatide-treated patients after 28 days of treatment were in remission from their ulcerative colitis symptoms. Dolcanatide was also safe and well tolerated.

Accordingly, the invention provides a method for preventing, treating or alleviating a symptom of ulcerative colitis by rectally administering to a subject in need of a therapeutically effective amount Dolcanatide or Plecanatide. In some embodiments, the subject has mild to moderate ulcerative colitis. Symptoms of ulcerative colitis include for example, diarrhea mixed with blood and mucus, and those symptoms recited in Table 1. In some embodiments, ulcerative colitis is scored according to Table 1.

TABLE 1

Ulcerative Colitis Symptom Severity

| Mild | Moderate | Severe | Very Severe (Fulminant) |
|---|---|---|---|
| Up to 4 loose stools per day | 4-6 loose stools per day | More than 6 bloody loose stools per day | More than 10 loose stools per day |
| Stools may be bloody | Stools may be bloody | | Constant blood in stools |
| Mild abdominal pain | Moderate abdominal pain | Fever, anemia, and rapid heart rate | Abdominal tenderness/distention |
| | Anemia | | Blood transfusion may be a requirement |
| | | | Potentially fatal complications |

Also included in the invention are rectal formulations of any of the GC-C agonists represented by Formulas I-XX as well as those amino acid sequences summarized below in Tables 2-8. The GC-C agonists according to the invention are collectively referred to herein as "GCRA peptides". In some embodiments, the GC-C agonist has the sequence of SEQ ID NO: 1 (SP-304), SP-333 (SEQ ID NO: 9); SP373 (SEQ ID NO.:104), SP364 (SEQ ID NO.:100), SP366 (SEQ ID NO.:102) or SED ID NO: 250.

In some embodiments, provided GC-C agonist formulations are useful for administration to a subject undergoing acute opioid use. In some embodiments, provided GC-C agonist formulations are useful for administration to patients suffering from post-operative gastrointestinal dysfunction, bowel dysfunction, or respiratory depression.

GCRA Peptides

The GCRA peptides of the present invention are analogues of uroguanylin, guanylin, lymphoguanylin and ST peptides. No particular length is implied by the term "peptide". In some embodiments, the GCRA peptide is less than 25 amino acids in length, e.g., less than or equal to 20, 15, 14, 13, 12, 11, 10, or 5 amino acids in length.

A preferred GCRA peptide according to the invention is SP-333 (SEQ ID NO:9). In some embodiments, the GCRA peptide is SP-333 (SEQ ID NO: 9), wherein the peptide is a (4,12; 7, 15) bicycle. In some embodiments, the GCRA peptide is SP-304 (SEQ ID NO: 1). In some embodiments, the GCRA peptide is SP-304 (SEQ ID NO: 1), wherein the peptide is a (4,12; 7, 15) bicycle.

The GCRA peptides can be polymers of L-amino acids, D-amino acids, or a combination of both. For example, in various embodiments, the peptides are D retro-inverso peptides. The term "retro-inverso isomer" refers to an isomer of a linear peptide in which the direction of the sequence is reversed and the chirality of each amino acid residue is inverted. See, e.g., Jameson et al., Nature, 368, 744-746 (1994); Brady et al., Nature, 368, 692-693 (1994). The net result of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence of the invention may be made into a D retro-inverso peptide by synthesizing a reverse of the sequence for the corresponding native L-amino acid sequence. For example a GCRA peptide includes the sequence defined by Formulas I-XX and those listed on Tables 2-8.

By inducing cGMP production is meant that the GCRA peptide induces the production of intracellular cGMP. Intracellular cGMP is measured by methods known in the art. For example, the GCRA peptides of the invention stimulate 5%, 10%, 20%, 30%, 40%, 50%, 75%, 90% or more intracellular cGMP compared to naturally occurring GC-C agonists. In further embodiments, the GCRA peptides stimulate apoptosis, e.g., programmed cell death, or activate the cystic fibrosis transmembrane conductance regulator (CFTR).

As used herein PEG3, 3 PEG, is meant to denote polyethylene glycol such as include aminoethyloxy-ethyloxy-acetic acid (AeeA).

As used herein, the term "AMIDE" is meant to denote that the terminal carboxylic acid is replaced with an amide group, i.e., the terminal COOH is replaced with $CONH_2$.

As used herein, the term "pyGlu" refers to pyroglutamic acid.

As used herein, (e.g., in Formulas I-XX) $X_{aa}$ is any natural, unnatural amino acid or amino acid analogue; $M_{aa}$ is a Cysteine (Cys), Penicillamine (Pen) homocysteine, or 3-mercaptoproline. $Xaa_{n1}$ is meant to denote an amino acid sequence of any natural, unnatural amino acid or amino acid analogue that is one, two or three residues in length; $Xaa_{n2}$ is meant to denote an amino acid sequence of any natural, unnatural amino acid or amino acid analogue that is zero or one residue in length; and $Xaa_{n3}$ is meant to denote an amino acid sequence of any natural, unnatural amino acid or amino acid analogue that is zero, one, two, three, four, five or six residues in length. Additionally, any amino acid represented by Xaa, may be an L-amino acid, a D-amino acid, a methylated amino acid, a fluorinated amino acid or any combination of thereof. Preferably the amino acids at the N-terminus, C-terminus or both are D-amino acids. Optionally, any GCRA peptide represented by Formulas I-XX may contain on or more polyethylene glycol residues at the N-terminus, C-terminus or both. An exemplary polyethylene glycol includes aminoethyloxy-ethyloxy-acetic acid and polymers thereof.

Specific examples of GCC agonist peptides that can be used in the methods and formulations of the invention include a peptide selected from Tables 2-8.

In some embodiments, GCC agonist peptides include peptides having the amino acid sequence of Formula I, wherein at least one amino acid of Formula I is a D-amino acid or a methylated amino acid and/or the amino acid at position 16 is a serine. Preferably, the amino acid at position 16 of Formula I is a D-amino acid or a methylated amino acid. For example, the amino acid at position 16 of Formula I is a d-leucine or a d-serine. Optionally, one or more of the amino acids at positions 1-3 of Formula I are D-amino acids or methylated amino acids or a combination of D-amino acids or methylated amino acids. For example, $Asn^1$, $Asp^2$ or $Glu^3$ (or a combination thereof) of Formula I is a D-amino acid or a methylated amino acid. Preferably, the amino acid at position $Xaa^6$ of Formula I is a leucine, serine or tyrosine.

In alternative embodiments, GCC agonist peptides include peptides having the amino acid sequence of Formula II, wherein at least one amino acid of Formula II is a D-amino acid or a methylated amino acid. Preferably, the amino acid denoted by $Xaa_{n2}$ of Formula II is a D-amino acid or a methylated amino acid. In some embodiments, the amino acid denoted by $Xaa_{n2}$ of Formula II is a leucine, a d-leucine, a serine, or a d-serine. Preferably, the one or more amino acids denoted by $Xaa_{n1}$ of Formula II are D-amino acids or methylated amino acids. Preferably, the amino acid at position $Xaa^6$ of Formula II is a leucine, a serine, or a tyrosine.

In some embodiments, GCC agonist peptides include peptides having the amino acid sequence of Formula III, wherein at least one amino acid of Formula III is a D-amino acid or a methylated amino acid and/or Maa is not a cysteine. Preferably, the amino acid denoted by $Xaa_{n2}$ of Formula III is a D-amino acid or a methylated amino acid. In some embodiments the amino acid denoted by $Xaa_{n2}$ of Formula III is a leucine, a d-leucine, a serine, or a d-serine. Preferably, the one or more amino acids denoted by $Xaa_{n1}$ of Formula III are D-amino acids or methylated amino acids. Preferably, the amino acid at position $Xaa^6$ of Formula III is a leucine, a serine, or a tyrosine.

In other embodiments, GCC agonist peptides include peptides having the amino acid sequence of Formula IV, wherein at least one amino acid of Formula IV is a D-amino acid or a methylated amino acid, and/or Maa is not a cysteine. Preferably, the $Xaa_{n2}$ of Formula IV is a D-amino acid or a methylated amino acid. In some embodiments, the amino acid denoted by $Xaa_{n2}$ of Formula IV is a leucine, a d-leucine, a serine, or a d-serine. Preferably, the one or more of the amino acids denoted by $Xaa_{n1}$ of Formula IV are D-amino acids or methylated amino acids. Preferably, the amino acid denoted $Xaa^6$ of Formula IV is a leucine, a serine, or a tyrosine.

In further embodiments, GCC agonist peptides include peptides having the amino acid sequence of Formula V, wherein at least one amino acid of Formula V is a D-amino acid or a methylated amino acid. Preferably, the amino acid at position 16 of Formula V is a D-amino acid or a methylated amino acid. For example, the amino acid at position 16 (i.e., $Xaa^{16}$) of Formula V is a d-leucine or a d-serine. Optionally, one or more of the amino acids at position 1-3 of Formula V are D-amino acids or methylated amino acids or a combination of D-amino acids or methylated amino acids. For example, $Asn^1$, $Asp^2$ or $Glu^3$ (or a combination thereof) of Formula V is a D-amino acids or a methylated amino acid. Preferably, the amino acid denoted at $Xaa^6$ of Formula V is a leucine, a serine, or a tyrosine.

In additional embodiments, GCRA peptides include peptides having the amino acid sequence of Formula VI, VII-a, VII-b, VIII, or IX. Preferably, the amino acid at position 6 of Formula VI, VII-a, VII-b, VIII, or IX is a leucine, a serine or a tyrosine. In some aspects the amino acid at position 16 of Formula VI, VII-a, VII-b, VIII or IX is a leucine or a serine. Preferably, the amino acid at position 16 of Formula VI, VII-a, VII-b, VIII or IX is a D-amino acid or a methylated amino acid.

In additional embodiments, GCRA peptides include peptides having the amino acid sequence of Formula X, XI, XII, XIII, XIV, XV, XVI or XVII. Optionally, one or more amino acids of Formulas X, XI, XII, XIII, XIV, XV, XVI or XVII are D-amino acids or methylated amino acids. Preferably, the amino acid at the carboxyl terminus of the peptides according to Formulas X, XI, XII, XIII, XIV, XV, XVI or XVII is a D-amino acid or a methylated amino acid. For example the amino acid at the carboxyl terminus of the peptides according to Formulas X, XI, XII, XIII, XIV, XV, XVI or XVII is a D-tyrosine.

Preferably, the amino acid denoted by $Xaa^6$ of Formula XIV is a tyrosine, phenylalanine or a serine. Most preferably the amino acid denoted by $Xaa^6$ of Formula XIV is a phenylalanine or a serine. Preferably, the amino acid denoted by $Xaa^4$ of Formula XV, XVI or XVII is a tyrosine, a phenylalanine, or a serine. Most preferably, the amino acid position $Xaa^4$ of Formula XV, XVI or XVII is a phenylalanine or a serine.

In some embodiments, GCRA peptides include peptides containing the amino acid sequence of Formula XVIII. Preferably, the amino acid at position 1 of Formula XVIII is a glutamic acid, aspartic acid, glutamine or lysine. Preferably, the amino acid at position 2 and 3 of Formula XVIII is a glutamic acid, or an aspartic acid. Preferably, the amino acid at position 5 is a glutamic acid. Preferably, the amino acid at position 6 of Formula XVIII is an isoleucine, valine, serine, threonine or tyrosine. Preferably, the amino acid at position 8 of Formula XVIII is a valine or isoleucine. Preferably, the amino acid at position 9 of Formula XVIII is an asparagine. Preferably, the amino acid at position 10 of Formula XVIII is a valine or a methionine. Preferably, the amino acid at position 11 of Formula XVIII is an alanine. Preferably, the amino acid at position 13 of Formula XVIII is a threonine. Preferably, the amino acid at position 14 of Formula XVIII is a glycine. Preferably, the amino acid at position 16 of Formula XVIII is a leucine, serine or threonine In alternative embodiments, GCRA peptides include peptides containing the amino acid sequence of Formula XIX. Preferably, the amino acid at position 1 of Formula XIX is a serine or asparagine. Preferably, the amino acid at position 2 of Formula XIX is a histidine or an aspartic acid. Preferably, the amino acid at position 3 of Formula XIX is a threonine or a glutamic acid. Preferably, the amino acid at position 5 of Formula XIX is a glutamic acid. Preferably, the amino acid at position 6 of Formula XIX is an isoleucine, leucine, valine or tyrosine. Preferably, the amino acid at position 8, 10, 11, or 13 of Formula XIX is an alanine. Preferably, the amino acid at position 9 of Formula XIX is an asparagine or a phenylalanine. Preferably, the amino acid at position 14 of Formula XIX is a glycine.

In further embodiments, GCRA peptides include peptides containing the amino acid sequence of Formula XX. Preferably, the amino acid at position 1 of Formula XX is a glutamine. Preferably, the amino acid at position 2 or 3 of Formula XX is a glutamic acid or an aspartic acid. Preferably, the amino acid at position 5 of Formula XX is a glutamic acid. Preferably, the amino acid at position 6 of Formula XX is threonine, glutamine, tyrosine, isoleucine, or leucine. Preferably, the amino acid at position 8 of Formula XX is isoleucine or valine. Preferably, the amino acid at position 9 of Formula XX is asparagine. Preferably, the amino acid at position 10 of Formula XX is methionine or valine. Preferably, the amino acid at position 11 of Formula XX is alanine. Preferably, the amino acid at position 13 of Formula XX is a threonine. Preferably, the amino acid at position 1 of Formula XX is a glycine. Preferably, the amino acid at position 15 of Formula XX is a tyrosine. Optionally, the amino acid at position 15 of Formula XX is two-amino acid in length and is Cysteine (Cys), Penicillamine (Pen) homocysteine, or 3-mercaptoproline and serine, leucine or threonine.

In certain embodiments, one or more amino acids of the GCRA peptides can be replaced by a non-naturally occurring amino acid or a naturally or non-naturally occurring amino acid analog. There are many amino acids beyond the standard 20 (Ala, Arg, Asn, Asp, Cys, Gln, Glu, Gly, His, Ile, Leu, Lys, Met, Phe, Pro, Ser, Thr, Trp, Tyr, and Val). Some are naturally-occurring others are not. (See, for example, Hunt, The Non-Protein Amino Acids: In Chemistry and Biochemistry of the Amino Acids, Barrett, Chapman and Hall, 1985). For example, an aromatic amino acid can be replaced by 3,4-dihydroxy-L-phenylalanine, 3-iodo-L-tyrosine, triiodothyronine, L-thyroxine, phenylglycine (Phg) or nor-tyrosine (norTyr). Phg and norTyr and other amino acids including Phe and Tyr can be substituted by, e.g., a halogen, —CH3, —OH, —CH2NH3, —C(O)H, —CH2CH3, —CN, —CH2CH2CH3, —SH, or another group. Any amino acid can be substituted by the D-form of the amino acid.

With regard to non-naturally occurring amino acids or naturally and non-naturally occurring amino acid analogs, a number of substitutions in the polypeptide and agonists described herein are possible alone or in combination.

For example, glutamine residues can be substituted with gamma-Hydroxy-Glu or gamma-Carboxy-Glu. Tyrosine residues can be substituted with an alpha substituted amino acid such as L-alpha-methylphenylalanine or by analogues such as: 3-Amino-Tyr; Tyr(CH3); Tyr(PO3(CH3)2); Tyr (SO3H); beta-Cyclohexyl-Ala; beta-(1-Cyclopentenyl)-Ala; beta-Cyclopentyl-Ala; beta-Cyclopropyl-Ala; beta-Quinolyl-Ala; beta-(2-Thiazolyl)-Ala; beta-(Triazole-1-yl)-Ala; beta-(2-Pyridyl)-Ala; beta-(3-Pyridyl)-Ala; Amino-Phe; Fluoro-Phe; Cyclohexyl-Gly; tBu-Gly; beta-(3-benzothienyl)-Ala; beta-(2-thienyl)-Ala; 5-Methyl-Trp; and A-Methyl-Trp. Proline residues can be substituted with homopro (L-pipecolic acid); hydroxy-Pro; 3,4-Dehydro-Pro; 4-fluoro-Pro; or alpha-methyl-Pro or an N(alpha)-C (alpha) cyclized amino acid analogues with the structure: n=0, 1, 2, 3 Alanine residues can be substituted with alpha-substituted or N-methylated amino acid such as alpha-amino isobutyric acid (aib), L/D-alpha-ethylalanine (L/D-isovaline), L/D-methylvaline, or L/D-alpha-methylleucine or a non-natural amino acid such as beta-fluoro-Ala. Alanine can also be substituted with: n=0, 1, 2, 3 Glycine residues can be substituted with alpha-amino isobutyric acid (aib) or L/D-alpha-ethylalanine (L/D-isovaline).

Further examples of unnatural amino acids include: an unnatural analog of alanine (e.g., L-1-Nal or L-2-Nal); an unnatural analog of tyrosine; an unnatural analogue of glutamine; an unnatural analogue of phenylalanine; an unnatural analogue of serine; an unnatural analogue of threonine; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; an amino acid that is amidated at a site that is not naturally amidated, a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid (e.g., an amino acid containing deuterium, tritium, $^{13}$C, $^{15}$N, or $^{18}$O); a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an α-hydroxy containing acid; an amino thio acid containing amino acid; an α, α disubstituted amino acid; a β-amino acid; a cyclic amino acid other than proline; an O-methyl-L-tyrosine; an L-3-(2-naphthyl)alanine; a 3-methyl-phenylalanine; a ρ-acetyl-L-phenylalanine; an O-4-allyl-L-tyrosine; a 4-propyl-L-tyrosine; a tri-O-acetyl-GlcNAcβ-serine; an L-Dopa; a fluorinated phenylalanine; an isopropyl-L-phenylalanine; a p-azido-L-phenylalanine; a p-acyl-L-phenylalanine; a p-benzoyl-L-phenylalanine; an L-phosphoserine; a phosphonoserine; a phosphonotyrosine; a p-iodo-phenylalanine; a 4-fluorophenylglycine; a p-bromophenylalanine; a p-amino-L-phenylalanine; an isopropyl-L-phenylalanine; L-3-(2-naphthyl)alanine; D-3-(2-naphthyl)alanine (dNal); an amino-, isopropyl-, or O-allyl-containing phenylalanine analogue; a dopa, 0-methyl-L-tyrosine; a glycosylated amino acid; a p-(propargyloxy) phenylalanine; dimethyl-Lysine; hydroxy-proline; mercaptopropionic acid; methyl-lysine; 3-nitro-tyrosine; norleucine; pyro-glutamic acid; Z (Carbobenzoxyl); ε-Acetyl-Lysine; β-alanine; β-aspartic acid; β-cyclohexyl-alanine; aminobenzoyl derivative; aminobutyric acid (Abu); citrulline; aminohexanoic acid (Ahx); aminoisobutyric acid (AIB); cyclohexylalanine; d-cyclohexylalanine; cyclohexylglycine; hydroxyproline; nitro-arginine; nitro-phenylalanine; nitro-tyrosine; norvaline; octahydroindole carboxylate; ornithine (Orn); penicillamine (PEN); tetrahydroisoquinoline; diaminobutyric acid; diaminopimelic acid; pyroglutamic acid; homocysteine; homoserine; N-ε-dinitrophenyl-lysine; N-ε-methyl-lysine; N-ε-dimethyl-lysine; N,N,N-ε-trimethyl-lysine; acetamidomethyl protected amino acids and pegylated amino acids. Further examples of unnatural amino acids and amino acid analogs can be found in U.S. 20030108885, U.S. 20030082575, US20060019347 (paragraphs 410-418) and the references cited therein. The polypeptides of the invention can include further modifications including those described in US20060019347, paragraph 589.

"Nal" used herein refers to both L-1-naphthylalanine (L-1-Nal) and L-2-naphthylalanine (L-2-Nal).

In some embodiments, an amino acid can be replaced by a naturally-occurring, non-essential amino acid, e.g., taurine.

Alternatively, the GCRA peptides are cyclic peptides. GCRA cyclic peptides are prepared by methods known in the art. For example, macrocyclization is often accomplished by forming an amide bond between the peptide N- and C-termini, between a side chain and the N- or C-terminus [e.g., with K$_3$Fe(CN)6 at pH 8.5] (Samson et al., Endocrinology, 137: 5182-5185 (1996)), or between two amino acid side chains, such as cysteine. See, e.g., DeGrado, Adv Protein Chem, 39: 51-124 (1988). In some embodiments, the GCRA peptides of the present invention are bicyclic peptides. In various aspects the GCRA peptides are [4,12; 7,15] bicycles.

In some GCRA peptides one or both members of one or both pairs of Cys residues which normally form a disulfide bond can be replaced by homocysteine, penicillamine, 3-mercaptoproline (Kolodziej et al. 1996 Int J Pept Protein Res 48:274); β, β dimethylcysteine (Hunt et al. 1993 Int JPept Protein Res 42:249) or diaminopropionic acid (Smith et al. 1978 J Med Chem 2 1:117) to form alternative internal cross-links at the positions of the normal disulfide bonds.

In addition, one or more disulfide bonds can be replaced by alternative covalent cross-links, e.g., an amide linkage (—CH2CH(O)NHCH2- or —CH2NHCH(O)CH2-), an ester linkage, a thioester linkage, a lactam bridge, a carbamoyl linkage, a urea linkage, a thiourea linkage, a phosphonate ester linkage, an alkyl linkage (—CH2CH2CH2CH2-), an alkenyl linkage(—CH 2CH=CHCH 2-), an ether linkage (—CH2CH2OCH2- or —CH2OCH2CH2-), a thioether linkage (—CH2CH2SCH2- or —CH2SCH2CH2-), an amine linkage (—CH2CH2NHCH2- or —CH2NHCH 2CH2-) or a thioamide linkage (—CH2CH(S)HNHCH 2- or —CH2NHCH(S)CH2-). For example, Ledu et al. (Proc Nat'l Acad. Sci. 100:11263-78, 2003) describe methods for preparing lactam and amide cross-links. Exemplary GCRA peptides which include a lactam bridge include for example SP-370.

The GCRA peptides can have one or more conventional polypeptide bonds replaced by an alternative bond. Such replacements can increase the stability of the polypeptide. For example, replacement of the polypeptide bond between a residue amino terminal to an aromatic residue (e.g. Tyr, Phe, Trp) with an alternative bond can reduce cleavage by carboxy peptidases and may increase half-life in the digestive tract. Bonds that can replace polypeptide bonds include: a retro-inverso bond (C(O)—NH instead of NH—C(O); a reduced amide bond (NH—CH2); a thiomethylene bond (S—CH2 or CH2-S); an oxomethylene bond (O—CH2 or CH2-O); an ethylene bond (CH2-CH2); a thioamide bond (C(S)—NH); a trans-olefine bond (CH=CH); a fluoro substituted trans-olefine bond (CF=CH); a ketomethylene bond (C(O)—CHR or CHR—C(O) wherein R is H or CH3; and a fluoro-ketomethylene bond (C(O)—CFR or CFR—C (O) wherein R is H or F or CH3.

The GCRA peptides can be modified using standard modifications. Modifications may occur at the amino (N—), carboxy (C—) terminus, internally or a combination of any of the preceding. In one aspect described herein, there may be more than one type of modification on the polypeptide. Modifications include but are not limited to: acetylation, amidation, biotinylation, cinnamoylation, farnesylation, formylation, myristoylation, palmitoylation, phosphorylation (Ser, Tyr or Thr), stearoylation, succinylation, sulfurylation and cyclisation (via disulfide bridges or amide cyclisation), and modification by Cys3 or Cys5. The GCRA peptides described herein may also be modified by 2, 4-dinitrophenyl (DNP), DNP-lysine, modification by 7-Amino-4-methyl-coumarin (AMC), flourescein, NBD (7-Nitrobenz-2-Oxa-1,3-Diazole), p-nitro-anilide, rhodamine B, EDANS (5-((2-aminoethyl)amino)naphthalene-1-sulfonic acid), dabcyl, dabsyl, dansyl, texas red, FMOC, and Tamra (Tetramethylrhodamine). The GCRA peptides described herein may also be conjugated to, for example, polyethylene glycol (PEG); alkyl groups (e.g., C1-C20 straight or branched alkyl groups); fatty acid radicals; combinations of PEG, alkyl groups and fatty acid radicals (See, U.S. Pat. No. 6,309,633; Soltero et al., 2001 Innovations in Pharmaceutical Technology 106-110); BSA and KLH (Keyhole Limpet Hemocyanin). The addition of PEG and other polymers which can be used to modify polypeptides of the invention is described in US2006019347 section IX.

In one aspect, the invention provides an Aad-GCRA peptide as taught in, for example, WO20140151206 which is hereby incorporated by reference in its entirety for all purposes. Table 1 of WO20140151206 discloses examples of various alpha-aminoadipic acid derivatives of GCRA Peptides. The Aad-GCRA peptides are analogues uroguanylin, guanylin, lymphoguanylin and ST peptides. Particularly, these analogs contain an α-aminoadipic acid (Ad), preferably at the 3rd position from the N-terminus of each peptide or at the position to the N-terminal side next to the first cysteine ("Cys") residue. For example an Aad-GCRA peptide includes the sequences defined by Formulae I, II, III, IV, V, VI, VII, VII, VIII, IX, XVIII or XXI which can comprise an α-aminoadipic acid.

In some embodiments, the Aad-GCRA peptide is $Asn^1$-$Asp^2$-$Aad^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ (SEQ ID NO: 258; SP-304-Aad), $dAsn^1$-$Asp^2$-$Aad^3$-$Cys^4$-$Glu^5$-$Leu^6$-$Cys^7$-$Val^8$-$Asn^9$-$Val^{10}$-$Cys^{12}$-$Thr^{13}$-$Gly^{14}$-$Cys^{15}$-$dLeu^{16}$ (SEQ ID NO: 253; SP-333-Aad); $Pyglu^1$-$Asp^2$-$Aad^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu$-$AMIDE^{16}$ (SEQ ID NO: 254; SP-373-Aad), $dAsn^1$-$Asp^2$-$Aad^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dSer^{16}$ (SEQ ID NO: 255; SP-364-Aad); $dAsn^1$-$Asp^2$-$Aad^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dTyr^{16}$ (SEQ ID NO: 256; SP-366-Aad); or $Xaa_{n1}$-$Cys^4$-$Xaa^5$-$Xaa^6$-$Xaa^7$-$Xaa^8$-$Xaa^9$-$Xaa^{10}$-$Xaa^{11}$-$Cys^{12}$-$Xaa^{13}$-$Xaa^{14}$-$Xaa^{15}$-$Xaa_{n2}^{16}$ (SEQ ID NO: 257).

Also included in the invention are peptides that biologically or functional equivalent to the peptides described herein. The term "biologically equivalent" or functional equivalent" is intended to mean that the compositions of the present invention are capable of demonstrating some or all of the cGMP production modulatory effects.

GCRA peptides can also include derivatives of GCRA peptides which are intended to include hybrid and modified forms of GCRA peptides in which certain amino acids have been deleted or replaced and modifications such as where one or more amino acids have been changed to a modified amino acid or unusual amino acid and modifications such as glycosylation so long the modified form retains the biological activity of GCRA peptides. By retaining the biological activity, it is meant that cGMP and or apoptosis is induced by the GCRA peptide, although not necessarily at the same level of potency as that of a naturally-occurring GCRA peptide identified.

Preferred variants are those that have conservative amino acid substitutions made at one or more predicted nonessential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a GCRA polypeptide is replaced with another amino acid residue from the same side chain family. Alternatively, in another embodiment, mutations can be introduced randomly along all or part of a GCRA coding sequence, such as by saturation mutagenesis, and the resultant mutants can be screened to identify mutants that retain activity.

TABLE 2

GCRA Peptides (SP-304 and Derivatives)

| Name | Position of Disulfide bonds | Structure | SEQ ID NO |
|---|---|---|---|
| SP-304 | C4:C12, C7:C15 | $Asn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 1 |
| SP-326 | C3:C11, C6:C14 | $Asp^1$-$Glu^2$-$Cys^3$-$Glu^4$-$Leu^5$-$Cys^6$-$Val^7$-$Asn^8$-$Val^9$-$Ala^{10}$-$Cys^{11}$-$Thr^{12}$-$Gly^{13}$-$Cys^{14}$-$Leu^{15}$ | 2 |
| SP-327 | C3:C11, C6:C14 | $Asp^1$-$Glu^2$-$Cys^3$-$Glu^4$-$Leu^5$-$Cys^6$-$Val^7$-$Asn^8$-$Val^9$-$Ala^{10}$-$Cys^{11}$-$Thr^{12}$-$Gly^{13}$-$Cys^{14}$ | 3 |
| SP-328 | C2:C10, C5:C13 | $Glu^1$-$Cys^2$-$Glu^3$-$Leu^4$-$Cys^5$-$Val^6$-$Asn^7$-$Val^8$-$Ala^9$-$Cys^{10}$-$Thr^{11}$-$Gly^{12}$-$Cys^{13}$-$Leu^{14}$ | 4 |
| SP-329 | C2:C10, C5:C13 | $Glu^1$-$Cys^2$-$Glu^3$-$Leu^4$-$Cys^5$-$Val^6$-$Asn^7$-$Val^8$-$Ala^9$-$Cys^{10}$-$Thr^{11}$-$Gly^{12}$-$Cys^{13}$ | 5 |
| SP-330 | C1:C9, C4:C12 | $Cys^1$-$Glu^2$-$Leu^3$-$Cys^4$-$Val^5$-$Asn^6$-$Val^7$-$Ala^8$-$Cys^9$-$Thr^{10}$-$Gly^{11}$-$Cys^{12}$-$Leu^{13}$ | 6 |
| SP-331 | C1:C9, C4:C12 | $Cys^1$-$Glu^2$-$Leu^3$-$Cys^4$-$Val^5$-$Asn^6$-$Val^7$-$Ala^8$-$Cys^9$-$Thr^{10}$-$Gly^{11}$-$Cys^{12}$ | 7 |
| SP332 | C4:C12, C7:C15 | $Cys^1$-$Glu^2$-$Leu^3$-$Cys^4$-$Val^5$-$Asn^6$-$Val^7$-$Ala^8$-$Cys^9$-$Thr^{10}$-$Gly^{11}$-$Cys^{12}$ | 8 |
| SP-333 | C4:C12, C7:C15 | $Asn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$ | 9 |
| SP-334 | C4:C12, C7:C15 | $dAsn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$ | 10 |
| SP-335 | C4:C12, C7:C15 | $dAsn^1$-$dAsp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$ | 11 |
| SP-336 | C4:C12, C7:C15 | $dAsn^1$-$dAsp^2$-$dGlu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$ | 12 |
| SP-337 | C4:C12, C7:C15 | $dAsn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 13 |
| SP-338 | C4:C12, C7:C15 | $dAsn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$ | 14 |
| SP-342 | C4:C12, C7:C15 | $Asn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$ | 15 |
| SP-343 | C4:C12, C7:C15 | PEG3-$Asn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$ | 16 |
| SP-344 | C4:C12, C7:C15 | PEG3-$dAsn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$-PEG3 | 17 |
| SP-347 | C4:C12, C7:C15 | PEG3-$dAsn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$-PEG3 | 18 |
| SP-348 | C4:C12, C7:C15 | PEG3-$dAsn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$ | 19 |
| SP-350 | C4:C12, C7:C15 | PEG3-$Asn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$ | 20 |
| SP-352 | C4:C12, C7:C15 | $Asn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$-PEG3 | 21 |
| SP-358 | C4:C12, C7:C15 | PEG3-$dAsn^1$-$dAsp^2$-$dGlu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$-PEG3 | 22 |

TABLE 2-continued

GCRA Peptides (SP-304 and Derivatives)

| Name | Position of Disulfide bonds | Structure | SEQ ID NO |
|---|---|---|---|
| SP-359 | C4:C12, C7:C15 | PEG3-dAsn$^1$-dAsp$^2$-dGlu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 23 |
| SP-360 | C4:C12, C7:C15 | dAsn$^1$-dAsp$^2$-dGlu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 24 |
| SP-361 | C4:C12, C7:C15 | dAsn$^1$-dAsp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 25 |
| SP-362 | C4:C12, C7:C15 | PEG3-dAsn$^1$-dAsp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 26 |
| SP-368 | C4:C12, C7:C15 | dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dNal$^{16}$ | 27 |
| SP-369 | C4:C12, C7:C15 | dAsn$^1$-Asp$^2$-Glu$^3$-Cys$^4$-Glu$^5$-Leu$^6$-Cys$^7$-Val$^8$-Asn$^9$-AIB$^{10}$-Ala$^{11}$-Cys$^{12}$-Thr$^{13}$-Gly$^{14}$-Cys$^{15}$-dLeu$^{16}$ | 28 |
| SP-370 | C4:C12, 7:15 | dAsn$^1$-Asp$^2$-Glu$^3$-Cys$^4$-Glu$^5$-Leu$^6$-Asp[Lactam]$^7$-Val$^8$-Asn$^9$-Val$^{10}$-Ala$^{11}$-Cys$^{12}$-Thr$^{13}$-Gly$^{14}$-Orn$^{15}$-dLeu$^1$ | 29 |
| SP-371 | C4:C12, C7:C15 | dAsn$^1$-Asp$^2$-Glu$^3$-Cys$^4$-Glu$^5$-Tyr$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 30 |
| SP-372 | C4:C12, C7:C15 | dAsn$^1$-Asp$^2$-Glu$^3$-Cys$^4$-Ser$^5$-Cys$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 31 |
| N1 | C4:C12, C7:C15 | PEG3-Asn$^1$-Asp$^2$-Glu$^3$-Cys$^4$-Glu$^5$-Tyr$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 32 |
| N2 | C4:C12, C7:C15 | dAsn$^1$-Asp$^2$-Glu$^3$-Cys$^4$-Glu$^5$-Tyr$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 33 |
| N3 | C4:C12, C7:C15 | dAsn$^1$-Asp$^2$-Glu$^3$-Cys$^4$-Glu$^5$-Tyr$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 34 |
| N4 | C4:C12, C7:C15 | PEG3-dAsn$^1$-Asp$^2$-Glu$^3$-Cys$^4$-Ser$^5$-Cys$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 35 |
| N5 | C4:C12, C7:C15 | dAsn$^1$-Asp$^2$-Glu$^3$-Cys$^4$-Ser$^5$-Cys$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 36 |
| N6 | C4:C12, C7:C15 | dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 37 |
| N7 | C4:C12, C7:C15 | Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 38 |
| N8 | C4:C12, C7:C15 | PEG3-Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$-PEG3 | 39 |
| N9 | C4:C12, C7:C15 | PEG3-Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 40 |
| N10 | C4:C12, C7:C15 | Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$-PEG3 | 41 |
| N11 | C4:C12, C7:C15 | PEG3-Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dSer$^{16}$ | 42 |
| N12 | C4:C12, C7:C15 | PEG3-Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dSer$^{16}$-PEG3 | 43 |
| N13 | C4:C12, C7:C15 | Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dSer$^{16}$ | 44 |
| Formula I | C4:C12, C7:C15 | Asn$^1$-Asp$^2$-Glu$^3$-Cys$^4$-Xaa$^5$-Xaa$^6$-Cys$^7$-Val$^8$-Asn$^9$-Val$^{10}$-Ala$^{11}$-Cys$^{12}$-Aaa$^{13}$-Xaa$^{14}$-Cys$^{15}$-Xaa$^{16}$ | 45 |
| Formula II | C4:C12, C7:C15 | Xaa$_{n1}$-Cys$^4$-Xaa$^5$-Xaa$^6$-Cys$^7$-Xaa$^8$-Xaa$^9$-Xaa$^{10}$-Xaa$^{11}$-Cys$^{12}$-Xaa$^{13}$-Xaa$^{14}$-Cys$^{15}$-Xaa$_{n2}$ | 46 |

TABLE 2-continued

GCRA Peptides (SP-304 and Derivatives)

| Name | Position of Disulfide bonds | Structure | SEQ ID NO |
|---|---|---|---|
| Formula III | 4:12, 7:15 | $Xaa_{n1}\text{-}Maa^4\text{-}Glu^5\text{-}Xaa^6\text{-}Maa^7\text{-}Val^8\text{-}Asn^9\text{-}Val^{10}\text{-}Ala^{11}\text{-}Maa^{12}\text{-}Thr^{13}\text{-}Gly^{14}\text{-}Maa^{15}\text{-}Xaa_{n2}$ | 47 |
| Formula IV | 4:12, 7:15 | $Xaa_{n1}\text{-}Maa^4\text{-}Xaa^5\text{-}Xaa^6\text{-}Maa^7\text{-}Xaa^8\text{-}Xaa^9\text{-}Xaa^{10}\text{-}Xaa^{11}\text{-}Maa^{12}\text{-}Xaa^{13}\text{-}Xaa^{14}\text{-}Maa^{15}\text{-}Xaa_{n2}$ | 48 |
| Formula V | C4:C12, C7:C15 | $Asn^1\text{-}Asp^2\text{-}Asp^3\text{-}Cys^4\text{-}Xaa^5\text{-}Xaa^6\text{-}Cys^7\text{-}Xaa^8\text{-}Asn^9\text{-}Xaa^{10}\text{-}Xaa^{11}\text{-}Cys^{12}\text{-}Xaa^{13}\text{-}Xaa^{14}\text{-}Cys^{15}\text{-}Xaa^{16}$ | 49 |
| Formula VI | C4:C12, C7:C15 | $dAsn^1\text{-}Glu^2\text{-}Glu^3\text{-}Cys^4\text{-}Xaa^5\text{-}Xaa^6\text{-}Cys^7\text{-}Xaa^8\text{-}Asn^9\text{-}Xaa^{10}\text{-}Xaa^{11}\text{-}Cys^{12}\text{-}Xaa^{13}\text{-}Xaa^{14}\text{-}Cys^{15}\text{-}d\text{-}Xaa^{16}$ | 50 |
| Formula VII-a | C4:C12, C7:C15 | $dAsn^1\text{-}dGlu^2\text{-}Asp^3\text{-}Cys^4\text{-}Xaa^5\text{-}Xaa^6\text{-}Cys^7\text{-}Xaa^8\text{-}Asn^9\text{-}Xaa^{10}\text{-}Xaa^{11}\text{-}Cys^{12}\text{-}Xaa^{13}\text{-}Xaa^{14}\text{-}Cys^{15}\text{-}d\text{-}Xaa^{16}$ | 51 |
| Formula VII-b | C4:C12, C7:C15 | $dAsn^1\text{-}dAsp^2\text{-}Glu^3\text{-}Cys^4\text{-}Xaa^5\text{-}Xaa^6\text{-}Cys^7\text{-}Xaa^8\text{-}Asn^9\text{-}Xaa^{10}\text{-}Xaa^{11}\text{-}Cys^{12}\text{-}Xaa^{13}\text{-}Xaa^{14}\text{-}Cys^{15}\text{-}d\text{-}Xaa^{16}$ | 52 |
| Formula VIII | C4:C12, C7:C15 | $dAsn^1\text{-}dAsp^2\text{-}dGlu^3\text{-}Cys^4\text{-}Xaa^5\text{-}Xaa^6\text{-}Cys^7\text{-}Xaa^8\text{-}Tyr^9\text{-}Xaa^{10}\text{-}Xaa^{11}\text{-}Cys^{12}\text{-}Xaa^{13}\text{-}Xaa^{14}\text{-}Cys^{15}\text{-}d\text{-}Xaa^{16}$ | 53 |
| Formula IX | C4:C12, C7:C15 | $dAsn^1\text{-}dGlu^2\text{-}dGlu^3\text{-}Cys^4\text{-}Xaa^5\text{-}Xaa^6\text{-}Cys^7\text{-}Xaa^8\text{-}Tyr^9\text{-}Xaa^{10}\text{-}Xaa^{11}\text{-}Cys^{12}\text{-}Xaa^{13}\text{-}Xaa^{14}\text{-}Cys^{15}\text{-}d\text{-}Xaa^{16}$ | 54 |
| Formula XXI | C4:C12, C7:C15 | $Xaa_{n1}\text{-}Cys^4\text{-}Xaa^5\text{-}Xaa^6\text{-}Xaa^7\text{-}Xaa^8\text{-}Xaa^9\text{-}Xaa^{10}\text{-}Xaa^{11}\text{-}Cys^{12}\text{-}Xaa^{13}\text{-}Xaa^{14}\text{-}Xaa^{15}\text{-}Xaa_{n2}^{16}$ | 250 |

TABLE 3

Linaclotide and Derivatives

| Name | Position of Disulfide Bonds | Structure | SEQ ID NO: |
|---|---|---|---|
| SP-339 (linaclotide) | C1:C6, C2:C10, C5:C13 | $Cys^1$-$Cys^2$-$Glu^3$-$Tyr^4$-$Cys^5$-$Cys^6$-$Asn^7$-$Pro^8$-$Ala^9$-$Cys^{10}$-$Thr^{11}$-$Gly^{12}$-$Cys^{13}$-$Tyr^{14}$ | 55 |
| SP-340 | C1:C6, C2:C10, C5:C13 | $Cys^1$-$Cys^2$-$Glu^3$-$Tyr^4$-$Cys^5$-$Cys^6$-$Asn^7$-$Pro^8$-$Ala^9$-$Cys^{10}$-$Thr^{11}$-$Gly^{12}$-$Cys^{13}$ | 56 |
| SP-349 | C1:C6, C2:C10, C5:C13 | PEG3-$Cys^1$-$Cys^2$-$Glu^3$-$Tyr^4$-$Cys^5$-$Cys^6$-$Asn^7$-$Pro^8$-$Ala^9$-$Cys^{10}$-$Thr^{11}$-$Gly^{12}$-$Cys^{13}$-$Tyr^{14}$-PEG3 | 57 |
| SP-353 | C3:C8, C4:C12, C7:C15 | $Asn^1$-$Phe^2$-$Cys^3$-$Cys^4$-$Glu^5$-$Ser^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 58 |
| SP-354 | C3:C8, C4:C12, C7:C15 | $Asn^1$-$Phe^2$-$Cys^3$-$Cys^4$-$Glu^5$-$Phe^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 59 |
| SP-355 | C1:C6, C2:C10, C5:C13 | $Cys^1$-$Cys^2$-$Glu^3$-$Tyr^4$-$Cys^5$-$Cys^6$-$Asn^7$-$Pro^8$-$Ala^9$-$Cys^{10}$-$Thr^{11}$-$Gly^{12}$-$Cys^{13}$-dTyr$^{14}$ | 60 |
| SP-357 | C1:C6, C2:C10, C5:C13 | PEG3-$Cys^1$-$Cys^2$-$Glu^3$-$Tyr^4$-$Cys^5$-$Cys^6$-$Asn^7$-$Pro^8$-$Ala^9$-$Cys^{10}$-$Thr^{11}$-$Gly^{12}$-$Cys^{13}$-$Tyr^{14}$ | 61 |
| SP-374 | C3:C8, C4:C12, C7:C15 | $Asn^1$-$Phe^2$-$Cys^3$-$Cys^4$-$Glu^5$-$Thr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 62 |
| SP-375 | C3:C8, C4:C12, C7:C15 | $Asn^1$-$Phe^2$-$Cys^3$-$Cys^4$-$Glu^5$-$Ser^6$-$Cys^7$-$Cys^8$-$Asn^9$-$Pro^{10}$-$Ala^{11}$-$Cys^{12}$-$Thr^{13}$-$Gly^{14}$-$Cys^{15}$-dTyr$^{16}$ | 63 |
| SP-376 | C3:C8, C4:C12, C7:C15 | $Asn^1$-$Phe^2$-$Cys^3$-$Cys^4$-$Glu^5$-$Ser^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 64 |
| SP-377 | C3:C8, C4:C12, C7:C15 | $Asn^1$-$Phe^2$-$Cys^3$-$Cys^4$-$Glu^5$-$Ser^6$-$Cys^7$-$Cys^8$-$Asn^9$-$Pro^{10}$-$Ala^{11}$-$Cys^{12}$-$Thr^{13}$-$Gly^{14}$-$Cys^{15}$-dTyr$^{16}$ | 65 |
| SP-378 | C3:C8, C4:C12, C7:C15 | $Asn^1$-$Phe^2$-$Cys^3$-$Cys^4$-$Glu^5$-$Thr^6$-$Cys^7$-$Cys^8$-$Asn^9$-$Pro^{10}$-$Ala^{11}$-$Cys^{12}$-$Thr^{13}$-$Gly^{14}$-$Cys^{15}$-dTyr$^{16}$ | 66 |
| SP-379 | C3:C8, C4:C12, C7:C15 | dAsn$^1$-$Phe^2$-$Cys^3$-$Cys^4$-$Glu^5$-$Thr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 67 |
| SP-380 | C3:C8, C4:C12, C7:C15 | dAsn$^1$-$Phe^2$-$Cys^3$-$Cys^4$-$Glu^5$-$Thr^6$-$Cys^7$-$Cys^8$-$Asn^9$-$Pro^{10}$-$Ala^{11}$-$Cys^{12}$-$Thr^{13}$-$Gly^{14}$-$Cys^{15}$-dTyr$^{16}$ | 68 |
| SP-381 | C3:C8, C4:C12, C7:C15 | $Asn^1$-$Phe^2$-$Cys^3$-$Cys^4$-$Glu^5$-$Phe^6$-$Cys^7$-$Cys^8$-$Asn^9$-$Pro^{10}$-$Ala^{11}$-$Cys^{12}$-$Thr^{13}$-$Gly^{14}$-$Cys^{15}$-dTyr$^{16}$ | 69 |
| SP-382 | C3:C8, C4:C12, C7:15 | dAsn$^1$-$Phe^2$-$Cys^3$-$Cys^4$-$Glu^5$-$Phe^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 70 |
| SP-383 | C3:C8, C4:C12, C7:15 | dAsn$^1$-$Phe^2$-$Cys^3$-$Cys^4$-$Glu^5$-$Phe^6$-$Cys^7$-$Cys^8$-$Asn^9$-$Pro^{10}$-$Ala^{11}$-$Cys^{12}$-$Thr^{13}$-$Gly^{14}$-$Cys^{15}$-dTyr$^{16}$ | 71 |

TABLE 3-continued

Linaclotide and Derivatives

| Name | Position of Disulfide Bonds | Structure | SEQ ID NO: |
|---|---|---|---|
| SP384 | C1:C6, C2:C10, C5:C13 | Cys$^1$-Cys$^2$-Glu$^3$-Tyr$^4$-Cys$^5$-Cys$^6$-Asn$^7$-Pro$^8$-Ala$^9$-Cys$^{10}$-Thr$^{11}$-Gly$^{12}$-Cys$^{13}$-Tyr$^{14}$-dTyr$^{16}$ | 72 |
| N14 | C1:C6, C2:C10, C5:C13 | PEG3-Cys$^1$-Cys$^2$-Glu$^3$-Tyr$^4$-Cys$^5$-Cys$^6$-Asn$^7$-Pro$^8$-Ala$^9$-Cys$^{10}$-Thr$^{11}$-Gly$^{12}$-Cys$^{13}$-PEG3 | 73 |
| N15 | C1:C6, C2:C10, C5:C13 | PEG3-Cys$^1$-Cys$^2$-Glu$^3$-Tyr$^4$-Cys$^5$-Cys$^6$-Asn$^7$-Pro$^8$-Ala$^9$-Cys$^{10}$-Thr$^{11}$-Gly$^{12}$-Cys$^{13}$-PEG3 | 74 |
| N16 | C1:C6, C2:C10, C5:C13 | Cys$^1$-Cys$^2$-Glu$^3$-Tyr$^4$-Cys$^5$-Cys$^6$-Asn$^7$-Pro$^8$-Ala$^9$-Cys$^{10}$-Thr$^{11}$-Gly$^{12}$-Cys$^{13}$-PEG3 | 75 |
| N17 | C3:C8, C4:C12, C7:C15 | PEG3-Asn$^1$-Phe$^2$-Cys$^3$-Cys$^4$-Glu$^5$-Ser$^6$-Cys$^7$-Cys$^8$-Asn$^9$-Pro$^{10}$-Ala$^{11}$-Cys$^{12}$-Thr$^{13}$-Gly$^{14}$-Cys$^{15}$ | 76 |
| N18 | C3:C8, C4:C12, C7:C15 | PEG3-Asn$^1$-Phe$^2$-Cys$^3$-Cys$^4$-Glu$^5$-Ser$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$-PEG3 | 77 |
| N19 | C3:C8, C4:C12, C7:C15 | Asn$^1$-Phe$^2$-Cys$^3$-Cys$^4$-Glu$^5$-Ser$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$-PEG3 | 78 |
| N20 | C3:C8, C4:C12, C7:C15 | PEG3-Asn$^1$-Phe$^2$-Cys$^3$-Cys$^4$-Glu$^5$-Phe$^6$-Cys$^7$-Cys$^8$-Asn$^9$-Pro$^{10}$-Ala$^{11}$-Cys$^{12}$-Thr$^{13}$-Gly$^{14}$-Cys$^{15}$ | 79 |
| N21 | C3:C8, C4:C12, C7:C15 | PEG3-Asn$^1$-Phe$^2$-Cys$^3$-Cys$^4$-Glu$^5$-Phe$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$-PEG3 | 80 |
| N22 | C3:C8, C4:C12, C7:C15 | Asn$^1$-Phe$^2$-Cys$^3$-Cys$^4$-Glu$^5$-Phe$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$ | 81 |
| N23 | C3:C8, C4:C12, C7:C15 | PEG3-Asn$^1$-Phe$^2$-Cys$^3$-Cys$^4$-Glu$^5$-Tyr$^6$-Cys$^7$-Cys$^8$-Asn$^9$-Pro$^{10}$-Ala$^{11}$-Cys$^{12}$-Thr$^{13}$-Gly$^{14}$-Cys$^{15}$ | 82 |
| N24 | C3:C8, C4:C12, C7:C15 | PEG3-Asn$^1$-Phe$^2$-Cys$^3$-Cys$^4$-Glu$^5$-Tyr$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$-PEG3 | 83 |
| N25 | C3:C8, C4:C12, C7:C15 | Asn$^1$-Phe$^2$-Cys$^3$-Cys$^4$-Glu$^5$-Tyr$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$ | 84 |
| N26 | C1:C6, C2:C10, C5:C13 | Cys$^1$-Cys$^2$-Glu$^3$-Ser$^4$-Cys$^5$-Cys$^6$-Asn$^7$-Pro$^8$-Ala$^9$-Cys$^{10}$-Thr$^{11}$-Gly$^{12}$-Cys$^{13}$-Tyr$^{14}$ | 85 |
| N27 | C1:C6, C2:C10, C5:C13 | Cys$^1$-Cys$^2$-Glu$^3$-Phe$^4$-Cys$^5$-Cys$^6$-Asn$^7$-Pro$^8$-Ala$^9$-Cys$^{10}$-Thr$^{11}$-Gly$^{12}$-Cys$^{13}$-Tyr$^{14}$ | 86 |
| N28 | C1:C6, C2:C10, C5:C13 | Cys$^1$-Cys$^2$-Glu$^3$-Ser$^4$-Cys$^5$-Cys$^6$-Asn$^7$-Pro$^8$-Ala$^9$-Cys$^{10}$-Thr$^{11}$-Gly$^{12}$-Cys$^{13}$ | 87 |
| N29 | C1:C6, C2:C10, C5:C13 | Cys$^1$-Cys$^2$-Glu$^3$-Phe$^4$-Cys$^5$-Cys$^6$-Asn$^7$-Pro$^8$-Ala$^9$-Cys$^{10}$-Thr$^{11}$-Gly$^{12}$-Cys$^{13}$ | 88 |
| N30 | 1:6, 2:10, 5:13 | Pen$^1$-Pen$^2$-Glu$^3$-Tyr$^4$-Pen$^5$-Pen$^6$-Asn$^7$-Pro$^8$-Ala$^9$-Pen$^{10}$-Thr$^{11}$-Gly$^{12}$-Pen$^{13}$-Tyr$^{14}$ | 89 |
| N31 | 1:6, 2:10, 5:13 | Pen$^1$-Pen$^2$-Glu$^3$-Tyr$^4$-Pen$^5$-Pen$^6$-Asn$^7$-Pro$^8$-Ala$^9$-Pen$^{10}$-Thr$^{11}$-Gly$^{12}$-Pen$^{13}$ | 90 |

TABLE 3-continued

Linaclotide and Derivatives

| Name | Position of Disulfide Bonds | Structure | SEQ ID NO: |
|---|---|---|---|
| Formula X | C9:C14, C10:C18, C13:C21 | $Xaa^1-Xaa^2-Xaa^3-Xaa^4-Xaa^5-Xaa^6-Asn^7-Tyr^8-Cys^9-Cys^{10}-Xaa^{11}-Tyr^{12}-Cys^{13}-Cys^{14}-Xaa^{15}-Xaa^{16}-Xaa^{17}-Cys^{18}-Xaa^{19}-Xaa^{20}-Cys^{21}-Xaa^{22}$ | 91 |
| Formula XI | C9:C14, C10:C18, C13:C21 | $Xaa^1-Xaa^2-Xaa^3-Xaa^4-Xaa^5-Xaa^6-Asn^7-Phe^8-Cys^9-Cys^{10}-Xaa^{11}-Phe^{12}-Cys^{13}-Cys^{14}-Xaa^{15}-Xaa^{16}-Xaa^{17}-Cys^{18}-Xaa^{19}-Xaa^{20}-Cys^{21}-Xaa^{22}$ | 92 |
| Formula XII | C3:C8, C4:C12, C7:C15 | $Asn^1-Phe^2-Cys^3-Cys^4-Xaa^5-Phe^6-Cys^7-Cys^8-Xaa^9-Xaa^{10}-Xaa^{11}-Cys^{12}-Xaa^{13}-Xaa^{14}-Cys^{15}-Xaa^{16}$ | 93 |
| Formula XIII | 3:8, 4:12, 7:15 | $Asn^1-Phe^2-Pen^3-Cys^4-Xaa^5-Phe^6-Cys^7-Pen^8-Xaa^9-Xaa^{10}-Xaa^{11}-Cys^{12}-Xaa^{13}-Xaa^{14}-Cys^{15}-Xaa^{16}$ | 94 |
| Formula XIV | 3:8, 4:12, 7:15 | $Asn^1-Phe^2-Maa^3-Maa^4-Xaa^5-Maa^6-Maa^7-Maa^8-Xaa^9-Xaa^{10}-Xaa^{11}-Maa^{12}-Xaa^{13}-Xaa^{14}-Maa^{15}-Xaa^{16}$ | 95 |
| Formula XV | 1:6, 2:10, 5:13 | $Maa^1-Maa^2-Glu^3-Xaa^4-Maa^5-Maa^6-Asn^7-Pro^8-Ala^9-Maa^{10}-Thr^{11}-Gly^{12}-Maa^{13}-Tyr^{14}$ | 96 |
| Formula XVI | 1:6, 2:10, 5:13 | $Maa^1-Maa^2-Glu^3-Xaa^4-Maa^5-Maa^6-Asn^7-Pro^8-Ala^9-Maa^{10}-Thr^{11}-Gly^{12}-Maa^{13}$ | 97 |
| Formula XVII | 1:6, 2:10, 5:13 | $Xaa_{n3}-Maa^1-Maa^2-Maa^3-Xaa^4-Maa^5-Maa^6-Xaa^7-Xaa^8-Xaa^9-Maa^{10}-Xaa^{11}-Maa^{12}-Maa^{13}-Xaa_{n2}$ | 98 |

TABLE 4

GCRA Peptides

| Name | Position of Disulfide bonds | Structure | SEQ ID NO: |
|---|---|---|---|
| SP-363 | C4:C12, C7:C15 | dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu-AMIDE$^{16}$ | 99 |
| SP-364 | C4:C12, C7:C15 | dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dSer$^{16}$ | 100 |
| SP-365 | C4:C12, C7:C15 | dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dSer-AMIDE$^{16}$ | 101 |
| SP-366 | C4:C12, C7:C15 | dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dTyr$^{16}$ | 102 |
| SP-367 | C4:C12, C7:C15 | dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dTyr-AMIDE$^{16}$ | 103 |
| SP-373 | C4:C12, C7:C15 | Pyglu$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu-AMIDE$^{16}$ | 104 |
| / | C4:C12, C7:C15 | Pyglu$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 251 |
| SP-304diPEG | C4:C12, C7:C15 | PEG3-Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$-PEG3 | 105 |
| SP-304N-PEG | C4:C12, C7:C15 | PEG3-Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 106 |
| SP-304C-PEG | C4:C12, C7:C15 | Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$-PEG3 | 107 |

TABLE 5

SP-304 Analogs, Uroguanylin, and Uroguanylin Analogs

| Name | Position of Disulfide bonds | Structure | SEQ ID NO |
|---|---|---|---|
| Formula XVIII | C4:C12, C7:C15 | Xaa$^1$-Xaa$^2$-Xaa$^3$-Maa$^4$-Xaa$^5$-Xaa$^6$-Maa$^7$-Xaa$^8$-Xaa$^9$-Xaa$^{10}$-Xaa$^{11}$-Maa$^{12}$-Xaa$^{13}$-Xaa$^{14}$-Maa$^{15}$-Xaa$^{16}$ | 108 |
| Uroguanylin | C4:C12, C7:C15 | Asn$^1$-Asp$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 109 |
| N32 | C4:C12, C7:C15 | Glu$^1$-Asp$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 110 |
| N33 | C4:C12, C7:C15 | Glu$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 111 |
| N34 | C4:C12, C7:C15 | Glu$^1$-Glu$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 112 |
| N35 | C4:C12, C7:C15 | Glu$^1$-Glu$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 113 |
| N36 | C4:C12, C7:C15 | Asp$^1$-Asp$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 114 |
| N37 | C4:C12, C7:C15 | Asp$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 115 |
| N38 | C4:C12, C7:C15 | Asp$^1$-Glu$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 116 |
| N39 | C4:C12, C7:C15 | Asp$^1$-Glu$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 117 |
| N40 | C4:C12, C7:C15 | Gln$^1$-Asp$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 118 |
| N41 | C4:C12, C7:C15 | Gln$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 119 |

TABLE 5-continued

SP-304 Analogs, Uroguanylin, and Uroguanylin Analogs

| Name | Position of Disulfide bonds | Structure | SEQ ID NO |
|---|---|---|---|
| N42 | C4:C12, C7:C15 | Gln$^1$-Glu$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 120 |
| N43 | C4:C12, C7:C15 | Gln$^1$-Glu$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 121 |
| N44 | C4:C12, C7:C15 | Lys$^1$-Asp$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 122 |
| N45 | C4:C12, C7:C15 | Lys$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 123 |
| N46 | C4:C12, C7:C15 | Lys$^1$-Glu$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 124 |
| N47 | C4:C12, C7:C15 | Lys$^1$-Glu$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 125 |
| N48 | C4:C12, C7:C15 | Glu$^1$-Asp$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 126 |
| N49 | C4:C12, C7:C15 | Glu$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 127 |
| N50 | C4:C12, C7:C15 | Glu$^1$-Glu$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 128 |
| N51 | C4:C12, C7:C15 | Glu$^1$-Glu$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 129 |
| N52 | C4:C12, C7:C15 | Asp$^1$-Asp$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-$^6$Gly$^{14}$-Cys$^{15}$-Leu$^1$ | 130 |
| N53 | C4:C12, C7:C15 | Asp$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 131 |
| N54 | C4:C12, C7:C15 | Asp$^1$-Glu$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 132 |
| N55 | C4:C12, C7:C15 | Asp$^1$-Glu$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 133 |
| N56 | C4:C12, C7:C15 | Gln$^1$-Asp$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 134 |
| N57 | C4:C12, C7:C15 | Gln$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 135 |
| N58 | C4:C12, C7:C15 | Gln$^1$-Glu$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 136 |
| N59 | C4:C12, C7:C15 | Gln$^1$-Glu$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 137 |
| N60 | C4:C12, C7:C15 | Lys$^1$-Asp$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 138 |
| N61 | C4:C12, C7:C15 | Lys$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 139 |
| N62 | C4:C12, C7:C15 | Lys$^1$-Glu$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 140 |
| N63 | C4:C12, C7:C15 | Lys$^1$-Glu$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Leu$^{16}$ | 141 |
| N65 | C4:C12, C7:C15 | Glu$^1$-Asp$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 142 |
| N66 | C4:C12, C7:C15 | Glu$^1$-Asp$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 143 |
| N67 | C4:C12, C7:C15 | Glu$^1$-Glu$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 144 |

TABLE 5-continued

SP-304 Analogs, Uroguanylin, and Uroguanylin Analogs

| Name | Position of Disulfide bonds | Structure | SEQ ID NO |
|---|---|---|---|
| N68 | C4:C12, C7:C15 | $Glu^1$-$Glu^2$-$Glu^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 145 |
| N69 | C4:C12, C7:C15 | $Asp^1$-$Asp^2$-$Asp^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 146 |
| N70 | C4:C12, C7:C15 | $Asp^1$-$Asp^2$-$Glu^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 147 |
| N71 | C4:C12, C7:C15 | $Asp^1$-$Glu^2$-$Asp^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 148 |
| N72 | C4:C12, C7:C15 | $Asp^1$-$Glu^2$-$Glu^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 149 |
| N73 | C4:C12, C7:C15 | $Gln^1$-$Asp^2$-$Asp^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 150 |
| N74 | C4:C12, C7:C15 | $Gln^1$-$Asp^2$-$Glu^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 151 |
| N75 | C4:C12, C7:C15 | $Gln^1$-$Glu^2$-$Asp^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 152 |
| N76 | C4:C12, C7:C15 | $Gln^1$-$Glu^2$-$Glu^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 153 |
| N77 | C4:C12, C7:C15 | $Lys^1$-$Asp^2$-$Asp^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 154 |
| N78 | C4:C12, C7:C15 | $Lys^1$-$Asp^2$-$Glu^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 155 |
| N79 | C4:C12, C7:C15 | $Lys^1$-$Glu^2$-$Asp^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 156 |
| N80 | C4:C12, C7:C15 | $Lys^1$-$Glu^2$-$Glu^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 157 |
| N81 | C4:C12, C7:C15 | $Glu^1$-$Asp^2$-$Asp^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 158 |
| N82 | C4:C12, C7:C15 | $Glu^1$-$Asp^2$-$Glu^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 159 |
| N83 | C4:C12, C7:C15 | $Glu^1$-$Glu^2$-$Asp^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 160 |
| N84 | C4:C12, C7:C15 | $Glu^1$-$Glu^2$-$Glu^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 161 |
| N85 | C4:C12, C7:C15 | $Asp^1$-$Asp^2$-$Asp^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 162 |
| N86 | C4:C12, C7:C15 | $Asp^1$-$Asp^2$-$Glu^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 163 |
| N87 | C4:C12, C7:C15 | $Asp^1$-$Glu^2$-$Asp^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 164 |
| N88 | C4:C12, C7:C15 | $Asp^1$-$Glu^2$-$Glu^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 165 |
| N89 | C4:C12, C7:C15 | $Gln^1$-$Asp^2$-$Asp^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 166 |
| N90 | C4:C12, C7:C15 | $Gln^1$-$Asp^2$-$Glu^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 167 |
| N91 | C4:C12, C7:C15 | $Gln^1$-$Glu^2$-$Asp^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 168 |
| N92 | C4:C12, C7:C15 | $Gln^1$-$Glu^2$-$Glu^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 169 |

TABLE 5-continued

SP-304 Analogs, Uroguanylin, and Uroguanylin Analogs

| Name | Position of Disulfide bonds | Structure | SEQ ID NO |
|---|---|---|---|
| N93 | C4:C12, C7:C15 | $Lys^1$-$Asp^2$-$Asp^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 170 |
| N94 | C4:C12, C7:C15 | $Lys^1$-$Asp^2$-$Glu^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 171 |
| N95 | C4:C12, C7:C15 | $Lys^1$-$Glu^2$-$Asp^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 172 |
| N96 | C4:C12, C7:C15 | $Lys^1$-$Glu^2$-$Glu^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Leu^{16}$ | 173 |

TABLE 6

Guanylin and Analogs

| Name | Position of Disulfide bonds | Structure | SEQ ID NO |
|---|---|---|---|
| Formula XIX | 4:12, 7:15 | $Xaa^1$-$Xaa^2$-$Xaa^3$-$Maa^4$-$Xaa^5$-$Xaaa^6$-$Maa^7$-$Xaa^8$-$Xaa^9$-$Xaa^{10}$-$Xaa^{11}$-$Maa^{12}$-$Xaa^{13}$-$Xaa^{14}$-$Maa^{15}$ | 174 |
| Guanylin | C4:C12, C7:C15 | $Ser^1$-$His^2$-$Thr^3$-$Cys^4$-$Glu^5$-$Ile^6$-$Cys^7$-$Ala^8$-$Phe^9$-$Ala^{10}$-$Ala^{11}$-$Cys^{12}$-$Ala^{13}$-$Gly^{14}$-$Cys^{15}$ | 175 |
| Human Guanylin | C4:C12, C7:C15 | $Pro^1$-$Gly^2$-$Thr^3$-$Cys^4$-$Glu^5$-$Ile^6$-$Cys^7$-$Ala^8$-$Tyr^9$-$Ala^{10}$-$Ala^{11}$-$Cys^{12}$-$Thr^{13}$-$Gly^{14}$-$Cys^{15}$ | 252 |
| N97 | C4:C12, C7:C15 | $Ser^1$-$His^2$-$Thr^3$-$Cys^4$-$Glu^5$-$Ile^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 176 |
| N98 | C4:C12, C7:C15 | $Ser^1$-$His^2$-$Thr^3$-$Cys^4$-$Glu^5$-$Leu^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 177 |
| N99 | C4:C12, C7:C15 | $Ser^1$-$His^2$-$Thr^3$-$Cys^4$-$Glu^5$-$Val^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 178 |
| N100 | C4:C12, C7:C15 | $Ser^1$-$His^2$-$Thr^3$-$Cys^4$-$Glu^5$-$Tyr^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 179 |
| N101 | C4:C12, C7:C15 | $Ser^1$-$His^2$-$Thr^3$-$Cys^4$-$Glu^5$-$Ile^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 180 |
| N102 | C4:C12, C7:C15 | $Ser^1$-$His^2$-$Thr^3$-$Cys^4$-$Glu^5$-$Leu^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 181 |
| N103 | C4:C12, C7:C15 | $Ser^1$-$His^2$-$Thr^3$-$Cys^4$-$Glu^5$-$Val^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 182 |
| N104 | C4:C12, C7:C15 | $Ser^1$-$His^2$-$Thr^3$-$Cys^4$-$Glu^5$-$Tyr^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 183 |
| N105 | C4:C12, C7:C15 | $Ser^1$-$His^2$-$Thr^3$-$Cys^4$-$Glu^5$-$Ile^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 184 |
| N106 | C4:C12, C7:C15 | $Ser^1$-$His^2$-$Thr^3$-$Cys^4$-$Glu^5$-$Leu^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 185 |
| N107 | C4:C12, C7:C15 | $Ser^1$-$His^2$-$Thr^3$-$Cys^4$-$Glu^5$-$Val^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 186 |
| N108 | C4:C12, C7:C15 | $Ser^1$-$His^2$-$Thr^3$-$Cys^4$-$Glu^5$-$Tyr^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 187 |
| N109 | C4:C12, C7:C15 | $Ser^1$-$His^2$-$Thr^3$-$Cys^4$-$Glu^5$-$Ile^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 188 |
| N110 | C4:C12, C7:C15 | $Ser^1$-$His^2$-$Thr^3$-$Cys^4$-$Glu^5$-$Leu^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 189 |
| N111 | C4:C12, C7:C15 | $Ser^1$-$His^2$-$Thr^3$-$Cys^4$-$Glu^5$-$Val^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 190 |
| N112 | C4:C12, C7:C15 | $Ser^1$-$His^2$-$Thr^3$-$Cys^4$-$Glu^5$-$Tyr^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 191 |
| N113 | C4:C12, C7:C15 | $Asn^1$-$Asp^2$-$Glu^3$-$Cys^4$-$Glu^5$-$Ile^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 192 |
| N114 | C4:C12, C7:C15 | $Asn^1$-$Asp^2$-$Glu^3$-$Cys^4$-$Glu^5$-$Leu^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 193 |
| N115 | C4:C12, C7:C15 | $Asn^1$-$Asp^2$-$Glu^3$-$Cys^4$-$Glu^5$-$Val^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 194 |
| N116 | C4:C12, C7:C15 | $Asn^1$-$Asp^2$-$Glu^3$-$Cys^4$-$Glu^5$-$Tyr^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 195 |
| N117 | C4:C12, C7:C15 | $Asn^1$-$Asp^2$-$Glu^3$-$Cys^4$-$Glu^5$-$Ile^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 196 |

TABLE 6-continued

Guanylin and Analogs

| Name | Position of Disulfide bonds | Structure | SEQ ID NO |
|---|---|---|---|
| N118 | C4:C12, C7:C15 | $Asn^1$-$Asp^2$-$Glu^3$-$Cys^4$-$Glu^5$-$Leu^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 197 |
| N119 | C4:C12, C7:C15 | $Asn^1$-$Asp^2$-$Glu^3$-$Cys^4$-$Glu^5$-$Val^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 198 |
| N120 | C4:C12, C7:C15 | $Asn^1$-$Asp^2$-$Glu^3$-$Cys^4$-$Glu^5$-$Tyr^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 199 |
| N121 | C4:C12, C7:C15 | $Asn^1$-$Asp^2$-$Glu^3$-$Cys^4$-$Glu^5$-$Ile^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 200 |
| N122 | C4:C12, C7:C15 | $Asn^1$-$Asp^2$-$Glu^3$-$Cys^4$-$Glu^5$-$Leu^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 201 |
| N123 | C4:C12, C7:C15 | $Asn^1$-$Asp^2$-$Glu^3$-$Cys^4$-$Glu^5$-$Val^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 202 |
| N124 | C4:C12, C7:C15 | $Asn^1$-$Asp^2$-$Glu^3$-$Cys^4$-$Glu^5$-$Tyr^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 203 |
| N125 | C4:C12, C7:C15 | $Asn^1$-$Asp^2$-$Glu^3$-$Cys^4$-$Glu^5$-$Ile^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 204 |
| N126 | C4:C12, C7:C15 | $Asn^1$-$Asp^2$-$Glu^3$-$Cys^4$-$Glu^5$-$Leu^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 205 |
| N127 | C4:C12, C7:C15 | $Asn^1$-$Asp^2$-$Glu^3$-$Cys^4$-$Glu^5$-$Val^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 206 |
| N128 | C4:C12, C7:C15 | $Asn^1$-$Asp^2$-$Glu^3$-$Cys^4$-$Glu^5$-$Tyr^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 207 |

TABLE 7

Lymphoguanylin and Analogs

| Name | Position of Disulfide bonds | Structure | SEQ ID NO |
|---|---|---|---|
| FormulaXX | 4:12 | $Xaa^1$-$Xaa^2$-$Xaa^3$-$Maa^4$-$Xaa^5$-$Xaa^6$-$Maa^7$-$Xaa^8$-$Xaa^9$-$xaa^{10}$-$Xaa^{11}$-$Maa^{12}$-$Xaa^{13}$-$Xaa^{14}$-$Xaa_{n1}^{15}$ | 208 |
| Lympho-guanylin | C4:C12 | $Gln^1$-$Glu^2$-$Glu^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 209 |
| N129 | C4:C12 | $Gln^1$-$Glu^2$-$Glu^3$-$Cys^4$-$Glu^5$-$Thr^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 210 |
| N130 | C4:C12 | $Gln^1$-$Asp^2$-$Glu^3$-$Cys^4$-$Glu^5$-$Thr^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 211 |
| N131 | C4:C12 | $Gln^1$-$Asp^2$-$Asp^3$-$Cys^4$-$Glu^5$-$Thr^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 212 |
| N132 | C4:C12 | $Gln^1$-$Glu^2$-$Asp^3$-$Cys^4$-$Glu^5$-$Thr^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 213 |
| N133 | C4:C12 | $Gln^1$-$Glu^2$-$Glu^3$-$Cys^4$-$Glu^5$-$Glu^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 214 |
| N134 | C4:C12 | $Gln^1$-$Asp^2$-$Glu^3$-$Cys^4$-$Glu^5$-$Glu^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 215 |
| N135 | C4:C12 | $Glni$-$Asp^2$-$Asp^3$-$Cys^4$-$Glu^5$-$Glu^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 216 |
| N136 | C4:C12 | $Gln^1$-$Glu^2$-$Asp^3$-$Cys^4$-$Glu^5$-$Glu^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 217 |
| N137 | C4:C12 | $Gln^1$-$Glu^2$-$Glu^3$-$Cys^4$-$Glu^5$-$Tyr^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 218 |
| N138 | C4:C12 | $Gln^1$-$Asp^2$-$Glu^3$-$Cys^4$-$Glu^5$-$Tyr^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 219 |
| N139 | C4:C12 | $Gln^1$-$Asp^2$-$Asp^3$-$Cys^4$-$Glu^5$-$Tyr^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 220 |
| N140 | C4:C12 | $Gln^1$-$Glu^2$-$Asp^3$-$Cys^4$-$Glu^5$-$Tyr^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 221 |
| N141 | C4:C12 | $Gln^1$-$Glu^2$-$Glu^3$-$Cys^4$-$Glu^5$-$Ile^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 222 |
| N142 | C4:C12 | $Gln^1$-$Asp^2$-$Glu^3$-$Cys^4$-$Glu^5$-$Ile^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 223 |
| N143 | C4:C12 | $Gln^1$-$Asp^2$-$Asp^3$-$Cys^4$-$Glu^5$-$Ile^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 224 |
| N144 | C4:C12 | $Gln^1$-$Glu^2$-$Asp^3$-$Cys^4$-$Glu^5$-$Ile^6$-$Cys^7$-$Ile^8$-$Asn^9$-$Met^{10}$-$Ala^{11}$-$Cys^{12}$-$Thr^{13}$-$Gly^{14}$-$Tyr^{15}$ | 225 |
| N145 | C4:C12, C7:C15 | $Gln^1$-$Glu^2$-$Glu^3$-$Cys^4$-$Glu^5$-$Thr^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 226 |

TABLE 7-continued

Lymphoguanylin and Analogs

| Name | Position of Disulfide bonds | Structure | SEQ ID NO |
|---|---|---|---|
| N146 | C4:C12, C7:C15 | Gln$^1$-Asp$^2$-Glu$^3$-Cys$^4$-Glu$^5$-Thr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 227 |
| N147 | C4:C12, C7:C15 | Gln$^1$-Asp$^2$-Asp$^3$-Cys$^4$-Glu$^5$-Thr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 228 |
| N148 | C4:C12, C7:C15 | Gln$^1$-Glu$^2$-Asp$^3$-Cys$^4$-Glu$^5$-Thr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 229 |
| N149 | C4:C12, C7:C15 | Gln$^1$-Glu$^2$-Glu$^3$-Cys$^4$-Glu$^5$-Glu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 230 |
| N150 | C4:C12, C7:C15 | Gln$^1$-Asp$^2$-Glu$^3$-Cys$^4$-Glu$^5$-Glu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 231 |
| N151 | C4:C12, C7:C15 | Gln$^1$-Asp$^2$-Asp$^3$-Cys$^4$-Glu$^5$-Glu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 232 |
| N152 | C4:C12, C7:C15 | Gln$^1$-Glu$^2$-Asp$^3$-Cys$^4$-Glu$^5$-Glu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 233 |
| N153 | C4:C12, C7:C15 | Gln$^1$-Glu$^2$-Glu$^3$-Cys$^4$-Glu$^5$-Tyr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 234 |
| N154 | C4:C12, C7:C15 | Gln$^1$-Asp$^2$-Glu$^3$-Cys$^4$-Glu$^5$-Tyr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 235 |
| N155 | C4:C12, C7:C15 | Gln$^1$-Asp$^2$-Asp$^3$-Cys$^4$-Glu$^5$-Tyr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 236 |
| N156 | C4:C12, C7:C15 | Gln$^1$-Glu$^2$-Asp$^3$-Cys$^4$-Glu$^5$-Tyr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 237 |
| N157 | C4:C12, C7:C15 | Gln$^1$-Glu$^2$-Glu$^3$-Cys$^4$-Glu$^5$-Ile$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 238 |
| N158 | C4:C12, C7:C15 | Gln$^1$-Asp$^2$-Glu$^3$-Cys$^4$-Glu$^5$-Ile$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 239 |
| N159 | C4:C12, C7:C15 | Gln$^1$-Asp$^2$-Asp$^3$-Cys$^4$-Glu$^5$-Ile$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 240 |
| N160 | C4:C12, C7:C15 | Gln$^1$-Glu$^2$-Asp$^3$-Cys$^4$-Glu$^5$-Ile$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 241 |

TABLE 8

ST Peptide and Analogues

| Name | Position of Disulfide bonds | Structure | SEQ ID NO |
|---|---|---|---|
| STPeptide | C9:C14, C10:C18, C13:C21 | Asn$^1$-Ser$^2$-Ser$^3$-Asn$^4$-Ser$^5$-Ser$^6$-Asn$^7$-Tyr$^8$-Cys$^9$-Cys$^{10}$-Glu$^{11}$-Lys$^{12}$-Cys$^{13}$-Cys$^{14}$-Asn$^{15}$-Pro$^{16}$-Ala$^{17}$-Cys$^{18}$-Thr$^{19}$-Gly$^{20}$-Cys$^{21}$-Tyr$^{22}$ | 242 |
| N161 | C3:C8, C4:C12, C7:C15 | PEG3-Asn$^1$-Phe$^2$-Cys$^3$-Cys$^4$-Glu$^5$-Thr$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$-PEG3 | 243 |
| N162 | C3:C8, C4:C12, C7:C15 | PEG3-Asn$^1$-Phe$^2$-Cys$^3$-Cys$^4$-Glu$^5$-Thr$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$ | 244 |
| N163 | C3:C8, C4:C12, C7:C15 | Asn$^1$-Phe$^2$-Cys$^3$-Cys$^4$-Glu$^5$-Thr$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$-PEG3 | 245 |
| N164 | C3:C8, C4:C12, C7:C15 | Asn$^1$-Phe$^2$-Cys$^3$-Cys$^4$-Glu$^5$-Tyr$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$ | 246 |
| N165 | C3:C8, C4:C12, C7:C15 | dAsn$^1$-Phe$^2$-Cys$^3$-Cys$^4$-Glu$^5$-Tyr$^6$-Cys$^7$-Cys$^8$-Asn$^9$-Pro$^{10}$-Ala$^{11}$-Cys$^{12}$-Thr$^{13}$-Gly$^{14}$-Cys$^{15}$-dTyr$^{16}$ | 247 |

TABLE 8-continued

ST Peptide and Analogues

| Name | Position of Disulfide bonds | Structure | SEQ ID NO |
|---|---|---|---|
| N166 | C3:C8, C4:C12, C7:C15 | Asn$^1$-Phe$^2$-Cys$^3$-Cys$^4$-Glu$^5$-Tyr$^6$-Cys$^7$-Cys$^8$-Asn$^9$-Pro$^{10}$-Ala$^{11}$-Cys$^{12}$-Thr$^{13}$-Gly$^{14}$-Cys$^{15}$-dTyr$^{16}$ | 248 |
| N167 | C3:C8, C4:C12, C7:C15 | dAsn$^1$-Phe$^2$-Cys$^3$-Cys$^4$-Glu$^5$-Tyr$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$ | 249 |

The term "consisting essentially of" includes peptides that are identical to a recited sequence (any one from Tables 2-8) and other sequences that do not differ substantially in terms of either structure or function. For the purpose of the present application, a peptide differs substantially if its structure varies by more than three amino acids from a peptide of any one from Tables 2-8 or if its activation of cellular cGMP production is reduced or enhanced by more than 50%. Preferably, substantially similar peptides should differ by no more than two amino acids and not differ by more than about 25% with respect to activating cGMP production.

Also included within the meaning of substantially homologous is any GCRA peptide which may be isolated by virtue of cross-reactivity with antibodies to the GCRA peptide.

Preparation of GCRA Peptides

GCRA peptides are easily prepared using modern cloning techniques, or may be synthesized by solid state methods or by site-directed mutagenesis. A GCRA peptide may include dominant negative forms of a polypeptide. Exemplary methods for preparing the GCRA peptide included the methods disclosed in WO/2012/118972 and WO/2013/138352, the contents of which are hereby incorporate by prefer in their entireties.

Chemical synthesis may generally be performed using standard solution phase or solid phase peptide synthesis techniques, in which a peptide linkage occurs through the direct condensation of the amino group of one amino acid with the carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (See, Gross and Meienhofer, eds., "The Peptides: Analysis, Synthesis, Biology," Vol. 1-4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. Solubility considerations are also a factor. Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., J. Am. Chem. Soc., 1963, 85:2149, which involves assembling a linear peptide chain on a resin support using protected amino acids. Solid phase peptide synthesis typically utilizes either the Boc or Fmoc strategy, which is well known in the art.

Those of ordinary skill in the art will recognize that, in solid phase synthesis, deprotection and coupling reactions must go to completion and the side-chain blocking groups must be stable throughout the synthesis. In addition, solid phase synthesis is generally most suitable when peptides are to be made on a small scale.

Acetylation of the N-terminal can be accomplished by reacting the final peptide with acetic anhydride before cleavage from the resin. C-amidation is accomplished using an appropriate resin such as methylbenzhydrylamine resin using the Boc technology.

Alternatively the GCRA peptides are produced by modern cloning techniques. For example, the GCRA peptides are produced either in bacteria including, without limitation, E. coli, or in other existing systems for polypeptide or protein production (e.g., Bacillus subtilis, baculovirus expression systems using Drosophila Sf9 cells, yeast or filamentous fungal expression systems, mammalian cell expression systems), or they can be chemically synthesized. If the GCRA peptide or variant peptide is to be produced in bacteria, e.g., E. coli, the nucleic acid molecule encoding the polypeptide may also encode a leader sequence that permits the secretion of the mature polypeptide from the cell. Thus, the sequence encoding the polypeptide can include the pre sequence and the pro sequence of, for example, a naturally-occurring bacterial ST polypeptide. The secreted, mature polypeptide can be purified from the culture medium.

The sequence encoding a GCRA peptide described herein can be inserted into a vector capable of delivering and maintaining the nucleic acid molecule in a bacterial cell. The DNA molecule may be inserted into an autonomously replicating vector (suitable vectors include, for example, pGEM3Z and pcDNA3, and derivatives thereof). The vector nucleic acid may be a bacterial or bacteriophage DNA such as bacteriophage lambda or M13 and derivatives thereof.

Construction of a vector containing a nucleic acid described herein can be followed by transformation of a host cell such as a bacterium. Suitable bacterial hosts include but are not limited to, E. coli, B subtilis, Pseudomonas, Salmonella. The genetic construct also includes, in addition to the encoding nucleic acid molecule, elements that allow expression, such as a promoter and regulatory sequences. The expression vectors may contain transcriptional control sequences that control transcriptional initiation, such as promoter, enhancer, operator, and repressor sequences.

A variety of transcriptional control sequences are well known to those in the art. The expression vector can also include a translation regulatory sequence (e.g., an untranslated 5' sequence, an untranslated 3' sequence, or an internal ribosome entry site). The vector can be capable of autonomous replication or it can integrate into host DNA to ensure stability during polypeptide production.

The protein coding sequence that includes a GCRA peptide described herein can also be fused to a nucleic acid encoding a polypeptide affinity tag, e.g., glutathione S-transferase (GST), maltose E binding protein, protein A, FLAG tag, hexa-histidine, myc tag or the influenza HA tag, in order to facilitate purification. The affinity tag or reporter fusion joins the reading frame of the polypeptide of interest to the reading frame of the gene encoding the affinity tag such that a translational fusion is generated. Expression of the fusion gene results in translation of a single polypeptide that includes both the polypeptide of interest and the affinity tag. In some instances where affinity tags are utilized, DNA sequence encoding a protease recognition site will be fused between the reading frames for the affinity tag and the polypeptide of interest.

Genetic constructs and methods suitable for production of immature and mature forms of the GCRA peptides and variants described herein in protein expression systems other than bacteria, and well known to those skilled in the art, can also be used to produce polypeptides in a biological system.

The peptides disclosed herein may be modified by attachment of a second molecule that confers a desired property upon the peptide, such as increased half-life in the body, for example, pegylation. Such modifications also fall within the scope of the term "variant" as used herein.

By "inhibiting" or "inhibition" or "reduce", it means the GCRA peptide decreases the activity and/or production of a protein by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%, or more relative to the activity and/or production of the protein without the GCRA peptide.

By "induce", it means the GCRA peptide increases the activity and/or production of a protein by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%, or more relative to the activity and/or production of the protein without the GCRA peptide.

The term "treatment" or "treating" refers to reducing or alleviating symptoms in a subject, preventing symptoms from worsening or progressing, and/or preventing disease in a subject who is free therefrom. For a given subject, improvement, worsening, regression, or progression of a symptom may be determined by any objective or subjective measure. Efficacy of the treatment may be measured as an improvement in morbidity or mortality (e.g., lengthening of survival curve for a selected population). Thus, effective treatment would include therapy of existing disease, control of disease by slowing or stopping its progression, prevention of disease occurrence, reduction in the number or severity of symptoms, or a combination thereof. The effect may be shown in a controlled study using one or more statistically significant criteria.

The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

Intracellular cGMP produced by exposing, e.g., contacting a tissue (e.g., gastrointestinal tissue; lung tissue, esophageal tissue) or cell with GCRA agonists. By inducing is meant an increase in cGMP production compared to a tissue or cell that has not been in contact with GCRA peptide or variant. Tissues or cells are directly contacted with a GCRA peptide or variant. Alternatively, the GCRA peptide or variant is administered systemically. GCRA peptide or variant are administered in an amount sufficient to increase intracellular cGMP concentration. cGMP production is measured by a cell-based assay known in the ar.

Disorders are treated, prevented or alleviated by administering to a subject, e.g., a mammal such as a human in need thereof, a therapeutically effective dose of a GCRA peptide. The GCRA peptides may be in a pharmaceutical composition in unit dose form, together with one or more pharmaceutically acceptable excipients. The term "unit dose form" refers to a single drug delivery entity, e.g., a tablet, capsule, solution or inhalation formulation. The amount of peptide present should be sufficient to have a positive therapeutic effect when administered to a patient. Typically a therapeutically effective amount is a unit dose form between 0.1 mg to 10 mg. Preferably the unit dose form is 1, 2, 3, 4, 5, 6, 7, 8, 9, or 10 mg. More preferably the unit dose is 3 mg or 6 mg. Most preferably the unit dose for is 6 mg. What constitutes a "positive therapeutic effect" will depend upon the particular condition being treated and will include any significant improvement in a condition readily recognized by one of skill in the art.

The GCRA peptides can be administered alone or in combination with another therapeutic agent, for example, those to treat, prevent, or ameliorate symptoms of inflammatory bowel disease, e.g., ulcerative colitis. Exemplary therapeutic agents, include but are not limited budesonide, iclosporin, tacrolimu, fexofenadine 5-ASA drugs such as sulfasalazine and mesalazine, corticosteroids such as prednisone, immunosuppressive medications such as azathioprine and biological agents such as infliximab and adalimumab.

Alternatively, two or more different GCRA peptides are administered. For example, SP-333 is administered with SEQ ID NO: 1 (SP-304), SP373 (SEQ ID NO.:104), SP364 (SEQ ID NO.:100), SP366 (SEQ ID NO.:102) or SED ID NO: 250. Preferably, SP-333 is administered rectally. Also for example, SP-304 is administered with SEQ ID NO: 9 (SP-333), SP373 (SEQ ID NO.:104), SP364 (SEQ ID NO.: 100), SP366 (SEQ ID NO.:102) or SED ID NO: 250. Preferably, SP-304 is administered rectally.

The term "combination therapy" means administering two or more active agents concurrently or sequentially. Concurrent administration may be achieved with a formulation in which two or more active agents are mixed, or with simultaneous administration of two or more active agents formulated independently. Sequential administration of two or more active agents may be achieved with two or more active agents, formulated independently, administered in sequence with one agent administered first followed by the second agent administered seconds, minutes, hours, or days after the first agent.

Combination therapy can be achieved by administering two or more agents, e.g., a GCRA peptide described herein or a composition described herein and another compound, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so.

The GCRA peptides described herein may be combined with phosphodiesterase inhibitors, e.g., sulindae sulfone, Zaprinast, sildenafil, vardenafil or tadalafil to further enhance levels of cGMP in the target tissues or organs.

Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y, Y-Y-X, X-X-Y-Y, etc.

Combination therapy can also include the administration of two or more agents via different routes or locations. For example, the GCRA peptide, preferably SP-333 is administered rectally and the other agent is administered orally, subcutaneously or intravenously. Alternatively, both the GCRA peptide and the other agent are administered rectally. In each case, the agents can either simultaneously or sequentially. Approximated dosages for some of the combination therapy agents described herein are found in the "BNF Recommended Dose" column of tables on pages 11-17 of WO01/76632 (the data in the tables being attributed to the March 2000 British National Formulary) and can also be found in other standard formularies and other drug prescribing directories. For some drugs, the customary prescribed dose for an indication will vary somewhat from country to country.

The GCRA peptides, alone or in combination, can be combined with any pharmaceutically acceptable carrier or medium. Thus, they can be combined with materials that do not produce an adverse, allergic or otherwise unwanted reaction when administered to a patient. The carriers or mediums used can include solvents, dispersants, coatings, absorption promoting agents, controlled release agents, and one or more inert excipients (which include starches, polyols, granulating agents, microcrystalline cellulose (e.g. celphere, Celphere Beads®), diluents, lubricants, binders, disintegrating agents, and the like), etc. If desired, tablet dosages of the disclosed compositions may be coated by standard aqueous or nonaqueous techniques.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include: sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a GCRA agonist) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. Such as mannitol, fructooligosaccharides, polyethylene glycol and other excipients. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In some embodiments, the compounds are administered rectally. Drugs administered rectally generally have a faster onset, higher bioavailability, shorter peak, and shorter duration than drugs administered orally. Rectally administered drugs also reach the circulatory system with less alteration and in greater concentrations thereby increasing drug efficacy.

The compounds can also be prepared in the form of suppositories (e.g., with conventional suppository bases such as cocoa butter and other glycerides) or retention enemas for rectal delivery. In some embodiments, the compounds are prepared in an aqueous formulation. In some embodiments, the compounds are prepared in a liquid formulation. In some embodiments, the compounds are prepared in saline.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, incorporated fully herein by reference.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

The pharmaceutical compositions can be included in a container, pack, or dispenser together with instructions for administration.

Compositions of the present invention may also optionally include other therapeutic ingredients, anti-caking agents, preservatives, sweetening agents, colorants, flavors, desiccants, plasticizers, dyes, glidants, anti-adherents, anti-static agents, surfactants (wetting agents), anti-oxidants, film-coating agents, and the like. Any such optional ingredient must be compatible with the compound described herein to insure the stability of the formulation.

The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myo-inositol, and the like, and hydrates thereof, and amino acids, for example alanine, glycine and betaine, and polypeptides and proteins, for example albumen.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents such as: BINDERS: corn starch, potato starch, other starches, gelatin, natural and synthetic gums such as acacia, xanthan, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone (e.g., povidone, crospovidone, copovidone, etc), methyl cellulose, Methocel, pre-gelatinized starch (e.g., STARCH 1500® and STARCH 1500 LM®, sold by Colorcon, Ltd.), hydroxypropyl methyl cellulose, microcrystalline cellulose (FMC Corporation, Marcus Hook, Pa., USA), or mixtures thereof, FILLERS: talc, calcium carbonate (e.g., granules or powder), dibasic calcium phosphate, tribasic calcium phosphate, calcium sulfate (e.g., granules or powder), microcrystalline cellulose, powdered cellulose, dextrates, kaolin, mannitol, silicic acid, sorbitol, starch, pre-gelatinized starch, dextrose, fructose, honey, lactose anhydrate, lactose monohydrate, lactose and aspartame, lactose and cellulose, lactose and microcrystalline cellulose, maltodextrin, maltose, mannitol, microcrystalline cellulose & guar gum, molasses, sucrose, or mixtures thereof, DISINTEGRANTS: agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums (like gellan), low-substituted hydroxypropyl cellulose, or mixtures thereof, LUBRICANTS: calcium stearate, magnesium stearate, mineral oil, light mineral oil, glycerin, sorbitol, mannitol, polyethylene glycol, other glycols, stearic acid, sodium lauryl sulfate, sodium stearyl fumarate, vegetable based fatty acids lubricant, talc, hydrogenated vegetable oil (e.g., peanut oil, cottonseed oil, sunflower oil, sesame oil, olive oil, corn oil and soybean oil), zinc stearate, ethyl oleate, ethyl laurate, agar, syloid silica gel (AEROSIL 200, W.R. Grace Co., Baltimore, Md. USA), a coagulated aerosol of synthetic silica (Deaussa Co., Piano, Tex. USA), a pyrogenic silicon dioxide (CAB-O-SIL, Cabot Co., Boston, Mass. USA), or mixtures thereof, ANTI-CAKING AGENTS: calcium silicate, magnesium silicate, silicon dioxide, colloidal silicon dioxide, talc, or mixtures thereof, ANTIMICROBIAL AGENTS: benzalkonium chloride, benzethonium chloride, benzoic acid, benzyl alcohol, butyl paraben, cetylpyridinium chloride, cresol, chlorobutanol, dehydroacetic acid, ethylparaben, methylparaben, phenol, phenylethyl alcohol, phenoxyethanol, phenylmercuric acetate, phenylmercuric nitrate, potassium sorbate, propylparaben, sodium benzoate, sodium dehydroacetate, sodium propionate, sorbic acid, thimersol, thymo, or mixtures thereof, and COATING AGENTS: sodium carboxymethyl cellulose, cellulose acetate phthalate, ethylcellulose, gelatin, pharmaceutical glaze, hydroxypropyl cellulose, hydroxypropyl methylcellulose (hypromellose), hydroxypropyl methyl cellulose phthalate, methylcellulose, polyethylene glycol, polyvinyl acetate phthalate, shellac, sucrose, titanium dioxide, carnauba wax, microcrystalline wax, gellan gum, maltodextrin, methacrylates, microcrystalline cellulose and carrageenan or mixtures thereof.

The formulation can also include other excipients and categories thereof including but not limited to L-histidine, Pluronic®, Poloxamers (such as Lutrol® and Poloxamer 188), ascorbic acid, glutathione, permeability enhancers (e.g. lipids, sodium cholate, acylcarnitine, salicylates, mixed bile salts, fatty acid micelles, chelators, fatty acid, surfactants, medium chain glycerides), protease inhibitors (e.g. soybean trypsin inhibitor, organic acids), pH lowering agents and absorption enhancers effective to promote bioavailability (including but not limited to those described in U.S. Pat. Nos. 6,086,918 and 5,912,014), creams and lotions (like maltodextrin and carrageenans); materials for chewable tablets (like dextrose, fructose, lactose monohydrate, lactose and aspartame, lactose and cellulose, maltodextrin, maltose, mannitol, microcrystalline cellulose and guar gum, sorbitol crystalline); parenterals (like mannitol and povidone); plasticizers (like dibutyl sebacate, plasticizers for coatings, polyvinylacetate phthalate); powder lubricants (like glyceryl behenate); soft gelatin capsules (like sorbitol special solution); spheres for coating (like sugar spheres); spheronization agents (like glyceryl behenate and microcrystalline cellulose); suspending/gelling agents (like carrageenan, gellan gum, mannitol, microcrystalline cellulose, povidone, sodium starch glycolate, xanthan gum); sweeteners (like aspartame, aspartame and lactose, dextrose, fructose, honey, maltodextrin, maltose, mannitol, molasses, sorbitol crystalline, sorbitol special solution, sucrose); wet granulation agents (like calcium carbonate, lactose anhydrous, lactose monohydrate, maltodextrin, mannitol, microcrystalline cellulose, povidone, starch), caramel, carboxymethylcellulose sodium, cherry cream flavor and cherry flavor, citric acid anhydrous, citric acid, confectioner's sugar, D&C Red No. 33, D&C Yellow #10 Aluminum Lake, disodium edetate, ethyl alcohol 15%, FD&C Yellow No. 6 aluminum lake, FD&C Blue #1 Aluminum Lake, FD&C Blue No. 1, FD&C blue no. 2 aluminum lake, FD&C Green No. 3, FD&C Red No. 40, FD&C Yellow No. 6 Aluminum Lake, FD&C Yellow No. 6, FD&C Yellow No. 10, glycerol palmitostearate, glyceryl monostearate, indigo carmine, lecithin, manitol, methyl and propyl parabens, mono ammonium glycyrrhizinate, natural and artificial orange flavor, pharmaceutical glaze, poloxamer 188, Polydextrose, polysorbate 20, polysorbate 80, polyvidone, pregelatinized corn starch, pregelatinized starch, red iron oxide, saccharin sodium, sodium carboxymethyl ether, sodium chloride, sodium citrate, sodium phosphate, strawberry flavor, synthetic black iron oxide, synthetic red iron oxide, titanium dioxide, and white wax.

Solid oral dosage forms may optionally be treated with coating systems (e.g. Opadry® fx film coating system, for example Opadry® blue (OY-LS-20921), Opadry® white (YS-2-7063), Opadry® white (YS-1-7040), and black ink (S-1-8 106).

The agents either in their free form or as a salt can be combined with a polymer such as polylactic-glycoloic acid (PLGA), poly-(I)-lactic-glycolic-tartaric acid (P(I)LGT) (WO 01/12233), polyglycolic acid (U.S. 3,773,919), polylactic acid (U.S. 4,767,628), poly(ε-caprolactone) and poly (alkylene oxide) (U.S. 20030068384) to create a sustained release formulation. Such formulations can be used to implants that release a polypeptide or another agent over a period of a few days, a few weeks or several months depending on the polymer, the particle size of the polymer, and the size of the implant (See, e.g., U.S. Pat. No. 6,620, 422). Other sustained release formulations and polymers for use in are described in EP 0 467 389 A2, WO 93/24150, U.S. Pat. No. 5,612,052, WO 97/40085, WO 03/075887, WO 01/01964A2, U.S. Pat. No. 5,922,356, WO 94/155587, WO 02/074247A2, WO 98/25642, U.S. Pat. Nos. 5,968,895, 6,180,608, U.S. 20030171296, U.S. 20020176841, U.S. Pat. Nos. 5,672,659, 5,893,985, 5,134,122, 5,192,741, 5,192, 741, 4,668,506, 4,713,244, 5,445,832, 4,931,279, 5,980,945, WO 02/058672, WO 97/26015, WO 97/04744, and US20020019446. In such sustained release formulations microparticles (Delie and Blanco-Prieto 2005 Molecule 10:65-80) of polypeptide are combined with microparticles of polymer. One or more sustained release implants can be placed in the large intestine, the small intestine or both. U.S. Pat. No. 6,011,011 and WO 94/06452 describe a sustained release formulation providing either polyethylene glycols (i.e. PEG 300 and PEG 400) or triacetin. WO 03/053401 describes a formulation which may both enhance bioavailability and provide controlled releaseof the agent within the GI tract. Additional controlled release formulations are described in WO 02/38129, EP 326151, U.S. Pat. No. 5,236,704, WO 02/30398, WO 98/13029; U.S. 20030064105, U.S. 20030138488A1, U.S. 20030216307A1, U.S. Pat. No. 6,667,060, WO 01/49249, WO 01/49311, WO 01/49249, WO 01/49311, and U.S. Pat. No. 5,877,224 materials which may include those described in WO04041195 (including the seal and enteric coating described therein) and pH-sensitive coatings that achieve delivery in the colon including those described in U.S. Pat. No. 4,910,021 and W9001329. U.S. Pat. No. 4,910,021 describes using a pH-sensitive material to coat a capsule. WO9001329 describes using pH-sensitive coatings on beads containing acid, where the acid in the bead core prolongs dissolution of the pH-sensitive coating. U.S. Pat. No. 5,175, 003 discloses a dual mechanism polymer mixture composed of pH-sensitive enteric materials and film-forming plasticizers capable of conferring permeability to the enteric material, for use in drug-delivery systems; a matrix pellet composed of a dual mechanism polymer mixture permeated with a drug and sometimes covering a pharmaceutically neutral nucleus; a membrane-coated pellet comprising a matrix pellet coated with a dual mechanism polymer mixture envelope of the same or different composition; and a pharmaceutical dosage form containing matrix pellets. The matrix pellet releases acid-soluble drugs by diffusion in acid pH and by disintegration at pH levels of nominally about 5.0 or higher.

In some embodiments, the compositions described herein are formulated in a pH dependent release form. Alternatively, such compositions are formulated in a form that releases the peptides at a specific region of the gastrointestinal (GI) tract (e.g., duodenum, jejunum, ileum, terminal ileum, or ascending colon). The formulation may contain an inert carrier coated with a composition and an enteric coating which releases the peptides at a specific pH (such as pH5 or pH7). Preferred pH for duodenum or jejunum release is pH 4.5-5.5 or pH 5.5-6.5. Preferred pH for ileum, terminal ileum, or ascending colon release is pH 5.5-6.5 or pH 6.5-7.5. Preferably, the inert carrier is a selected from mannitol, lactose, a microcrystalline cellulose, or starch.

The GCRA peptides described herein may be formulated in the pH triggered targeted control release systems described in WO04052339. The agents described herein may be formulated according to the methodology described in any of WO03105812 (extruded hyrdratable polymers); WO0243767 (enzyme cleavable membrane translocators); WO03007913 and WO03086297 (mucoadhesive systems); WO02072075 (bilayer laminated formulation comprising pH lowering agent and absorption enhancer); WO04064769 (amidated polypeptides); WO05063156 (solid lipid suspension with pseudotropic and/or thixotropic properties upon melting); WO03035029 and WO03035041 (erodible, gastric retentive dosage forms); US5007790 and US5972389 (sustained release dosage forms); WO041 1271 1 (oral extended release compositions); WO05027878, WO02072033, and WO02072034 (delayed release compositions with natural or synthetic gum); WO05030182 (controlled release formulations with an ascending rate of release); WO05048998 (microencapsulation system); U.S. Pat. No. 5,952,314 (biopolymer); U.S. Pat. No. 5,108,758 (glassy amylose matrix delivery); U.S. Pat. No. 5,840,860 (modified starch based delivery). JP10324642 (delivery system comprising chitosan and gastric resistant material such as wheat gliadin or zein); U.S. Pat. Nos. 5,866,619 and 6,368,629 (saccharide containing polymer); U.S. Pat. No. 6,531,152 (describes a drug delivery system containing a water soluble core (Ca pectinate or other water-insoluble polymers) and outer coat which bursts (e.g. hydrophobic polymer-Eudragrit)); U.S. Pat. Nos. 6,234,464; 6,403,130 (coating with polymer containing casein and high methoxy pectin; WO0174 175 (Maillard reaction product); WO05063206 (solubility increasing formulation); WO040 19872 (transferring fusion proteins).

Rectal Formulations

In preferred embodiments, the GCC agonists are formulated for rectal delivery. More preferably SP-333 or SP-304 is formulated for rectal delivery. For example, the GCC agonists are administered rectally by means of an enema, a suppository, rectal catheters or liposomally. In some embodiments, the release of the composition is time dependent.

In particular, compositions for rectal administration include solutions and emulsions.

The compositions of the present invention may also be formulated as suspensions in aqueous, non-aqueous or mixed media. Preferred aqueous solutions include saline. Aqueous suspensions may further contain substances which increase the viscosity of the suspension including, for example, sodium carboxymethylcellulose, sorbitol and/or dextran. The suspension may also contain stabilizers. In some embodiments, the formulation is an aqueous formulation. In some embodiments, the formulation is a liquid formulation. In some embodiments, the liquid is saline.

In some embodiments, the formulations for rectal administration comprise the peptide of SEQ ID NO: 9, where said peptide is a (4,12:7,15) bicycle. In some embodiments, the formulations for rectal administration comprise the peptide of SEQ ID NO: 1, where said peptide is a (4,12:7,15) bicycle. In some embodiments, the formulation is a liquid such as saline. In some embodiments, formulation is aqueous. In some embodiments the formulations for rectal administration comprise 6 mg of dolcanatide (SEQ ID NO: 9).

In some embodiments, the formulation is an enema or a suppository. Formulations for rectal administration may be presented as a suppository, which may be prepared by mixing the GCC agonists, preferably SP-333 with one or more suitable non-irritating carriers comprising, for example, cocoa butter, polyethylene glycol, a suppository wax, or a salicylate, and which is solid at room temperature, but liquid at body temperature and, therefore, will melt in the appropriate body cavity and release the encapsulated compound(s) and composition(s). suppositories, and enemas.

Dosage

Dosage levels of active ingredients in a pharmaceutical composition can also be varied so as to achieve a transient or sustained concentration of the compound in a subject, especially in and around the site of inflammation or disease area, and to result in the desired response. It is well within the skill of the art to start doses of the compound at levels lower than required to achieve the desired effect and to gradually increase the dosage until the desired effect is achieved. It will be understood that the specific dose level for any particular subject will depend on a variety of factors, including body weight, general health, diet, natural history of disease, route and scheduling of administration, combination with one or more other drugs, and severity of disease.

An effective dosage of the composition will typically be between 0.1 mg to 10 mg. Adjustments in dosage will be made using methods that are routine in the art and will be based upon the particular composition being used and clinical considerations.

Dosage levels of the GCR agonist for use in methods of this invention typically are from about 0.1 mg to about 10 mg daily. For example, an effective dosage of the GCRA peptide e.g. SP-333 or SP-304) for use in methods of this invention is about 0.1 to 100 mg per day, or optionally twice a day. In some embodiments, an effective dosage of the CGRA peptide (e.g. SP-333 or SP-304) for use in methods of this invention is about 0.1, about 0.2. about 0.3, about 0.4.about 0.5, about 0.6, about 0.7, about 0.8, about 0.9, about 1.0, about 1.5, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 9.5, about 10, about 20, about 30, about 40, about 50, about 60, about 70, about 80, about 90, or about 100 mg per day, or optionally twice a day. Preferably the GCRA peptide is given after in the evening, such as after dinner or before bedtime. In some embodiments, the GCRA peptide is SP-333 and is administered at a dose of about 2 mg to about 8 mg. In some embodiments, the GCRA peptide is SP-333 and is administered at a dose of about 2.7 mg, about 3 mg, about 5.7 mg, or about 6 mg. In some embodiments, the GCRA peptide is SP-304 and is administered at a dose of about 2 mg to about 10 mg. In some embodiments, the GCRA peptide is SP-304 and is administered at a dose of about 3 mg, about 6 mg, or about 9 mg.

In some embodiments, the GCR agonist is administered weekly, daily, or multi-daily. In preferred embodiments, the GCR agonist is administered daily.

The GCRA peptide can be administered until ulcerative colitis symptoms improve. In some embodiments, the GCRA peptide is administered for about 1 day to about 10 years. In some embodiments, the CGRA peptide is administered for about 1 day, about 2 days, about 3 days, about 4 days, about 5 days, about 6 days, about 7 days, about 2 weeks, about 3 weeks, about 4 weeks, about 1 month, about 2 months, about 3 months, about 4 months, about 5 months, about 6 months, about 7 months, about 8 months, about 9 months, about 10 months, about 11 months, about 12 months, about 1 year, about 2 years, about 5 years or longer. In some embodiments, the GCRA peptide is administered for 28 days.

The GCRA peptide can be administered once daily until ulcerative colitis symptoms improve. In some embodiments, the GCRA peptide is administered once daily for about 1 day to about 10 years. In some embodiments, the CGRA peptide is administered for about 1 day, about 2 days, about 3 days, about 4 days, about 5 days, about 6 days, about 7 days, about 2 weeks, about 3 weeks, about 4 weeks, about 1 month, about 2 months, about 3 months, about 4 months, about 5 months, about 6 months, about 7 months, about 8 months, about 9 months, about 10 months, about 11 months, about 12 months, about 1 year, about 2 years, about 5 years or longer. In some embodiments, the GCRA peptide is administered once daily for 28 days. In some embodiments SP-333 is administered once daily for 28 days.

The total daily dose of each inhibitor can be administered to the patient in a single dose, or in multiple subdoses. Preferably the total daily dose is administered as a single dose. Typically, subdoses can be administered two to six times per day, preferably two to four times per day, and even more preferably two to three times per day. Doses can be in immediate release form or sustained release form sufficiently effective to obtain the desired control over the medical condition.

The dosage regimen to prevent, treat, give relief from, or ameliorate a medical condition or disorder, or to otherwise protect against or treat a medical condition with the combinations and compositions of the present invention is selected in accordance with a variety of factors. These factors include, but are not limited to, the type, age, weight, sex, diet, and medical condition of the subject, the severity of the disease, the route of administration, pharmacological considerations such as the activity, efficacy, pharmacokinetics and toxicology profiles of the particular inhibitors employed, whether a drug delivery system is utilized, and whether the inhibitors are administered with other active ingredients. Thus, the dosage regimen actually employed may vary widely and therefore deviate from the preferred dosage regimen set forth above.

EXAMPLES

Example 1

Rectal Delivery of Dolcanatide Improved Ulcerative Colitis Symptoms

A double-blind, placebo-controlled, four week study was performed evaluating 28 patients with mild to moderate ulcerative colitis. Subjects were treated with either saline (placebo) or Dolcanatide (SP-333; SEQ ID NO: 9). Six mg of Dolcanatide was dissolved in saline and administered intra-rectally every evening for 28 days. At the end of treatment, dolcanatide-treated patients exhibited clear signals of improvement compared with placebo-treated patients. Particularly, dolcanatide-treated patients were in remission from their ulcerative colitis symptoms after treatment for 28 days.

Example 2

Rectal Delivery of Plecanatide Improved Ulcerative Colitis Symptoms

Subjects with mild-to-moderate ulcerative colitis will receive intra-rectal administration of either saline or 3 mg, 6 mg, or 9 mg Plecanatide (SP-304; SEQ ID NO: 1) for at least 28 days. At the end of treatment, subjects will be evaluated for presence and severity of ulcerative colitis symptoms in Plecanatide-treated subjects compared with placebo-treated subjects.

We claim:

1. A method for preventing, treating, or alleviating a symptom of ulcerative colitis, the method comprising rectally administering once daily for at least 28 days to a subject in need thereof a therapeutically effective amount of a composition comprising 6 mg of dolcanatide (SEQ ID NO: 9), and inducing remission of the symptoms of ulcerative colitis in the subject.

2. The method of claim 1, wherein the composition is administered prior to bedtime.

3. The method of claim 1, wherein the composition is an enema.

4. The method of claim 1, wherein the composition is a suppository.

5. The method of claim 1, wherein the release of the composition is time dependent.

6. The method of claim 1, wherein the composition is a liquid.

7. The method of claim 6, wherein the liquid is saline.

* * * * *

SEQUENCE LISTING

```
<160> NUMBER OF SEQ ID NOS: 258

<210> SEQ ID NO 1
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 1

Asn Asp Glu Cys Glu Leu Cys Val Asn Val Ala Cys Thr Gly Cys Leu
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 2

Asp Glu Cys Glu Leu Cys Val Asn Val Ala Cys Thr Gly Cys Leu
1               5                   10                  15

<210> SEQ ID NO 3
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 3
```

Asp Glu Cys Glu Leu Cys Val Asn Val Ala Cys Thr Gly Cys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Chemcially Synthesized

<400> SEQUENCE: 4

Glu Cys Glu Leu Cys Val Asn Val Ala Cys Thr Gly Cys Leu
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 5

Glu Cys Glu Leu Cys Val Asn Val Ala Cys Thr Gly Cys
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 6

Cys Glu Leu Cys Val Asn Val Ala Cys Thr Gly Cys Leu
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 7

Cys Glu Leu Cys Val Asn Val Ala Cys Thr Gly Cys
1               5                   10

<210> SEQ ID NO 8
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein LEU is a D amino acid

<400> SEQUENCE: 8

Asn Asp Glu Cys Glu Leu Cys Val Asn Val Ala Cys Thr Gly Cys Leu
1               5                   10                  15

<210> SEQ ID NO 9
<211> LENGTH: 16
<212> TYPE: PRT
<213> ORGANISM: Artificial Sequence
<220> FEATURE:

```
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (16)..(16)
<223> OTHER INFORMATION: wherein LEU is a D amino acid

<400> SEQUENCE: 9

Asn Asp Glu Cys Glu Leu Cys Val Asn Val Ala Cys Thr Gly Cys Leu
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (2)..(2)
<223> OTHER INFORMATION: wherein ASP is a D amino acid
<220> FEATURE:
<221> NAME/KEY: MISC_FEATURE
<222> LOCATION: (16)..(16)
<223> OTHER INFORMATION: wherein LEU is a D amino acid

<400> SEQUENCE: 10

Asn Asp Glu Cys Glu Leu Cys Val Asn Val Ala Cys Thr Gly Cys Leu
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (2)..(2)
<223> OTHER INFORMATION: wherein ASP is a D amino acid
<220> FEATURE:
<221> NAME/KEY: MISC_FEATURE
<222> LOCATION: (3)..(3)
<223> OTHER INFORMATION: wherein GLU is a D amino acid
<220> FEATURE:
<221> NAME/KEY: MISC_FEATURE
<222> LOCATION: (16)..(16)
<223> OTHER INFORMATION: wherein LEU is a D amino acid

<400> SEQUENCE: 11

Asn Asp Glu Cys Glu Leu Cys Val Asn Val Ala Cys Thr Gly Cys Leu
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
```

```
<223> OTHER INFORMATION: wherein ASN is a D amino acid

<400> SEQUENCE: 12

Asn Asp Glu Cys Glu Leu Cys Val Asn Val Ala Cys Thr Gly Cys Leu
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (6)..(6)
<223> OTHER INFORMATION: wherein LEU is a D amino acid
<220> FEATURE:
<221> NAME/KEY: MISC_FEATURE
<222> LOCATION: (16)..(16)
<223> OTHER INFORMATION: wherein LEU is a D amino acid

<400> SEQUENCE: 13

Asn Asp Glu Cys Glu Leu Cys Val Asn Val Ala Cys Thr Gly Cys Leu
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 14

Asn Asp Glu Cys Glu Leu Cys Val Asn Val Ala Cys Thr Gly Cys
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein Asn at position 1 is attached to
      polyethylene glycol
<220> FEATURE:
<221> NAME/KEY: MISC_FEATURE
<222> LOCATION: (16)..(16)
<223> OTHER INFORMATION: wherein Leu is a D amino acid
<220> FEATURE:
<221> NAME/KEY: MISC_FEATURE
<222> LOCATION: (16)..(16)
<223> OTHER INFORMATION: wherein Leu at position 16 is attached to
      polyethylene glycol

<400> SEQUENCE: 15

Asn Asp Glu Cys Glu Leu Cys Val Asn Val Ala Cys Thr Gly Cys Leu
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Chemically Synthesized
```

```
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (16)..(16)
<223> OTHER INFORMATION: wherein LEU is a D amino acid
<220> FEATURE:
<221> NAME/KEY: MISC_FEATURE
<222> LOCATION: (16)..(16)
<223> OTHER INFORMATION: wherein LEU at position 16 is attached to
      polyethylene glycol

<400> SEQUENCE: 16

Asn Asp Glu Cys Glu Leu Cys Val Asn Val Ala Cys Thr Gly Cys Leu
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (2)..(2)
<223> OTHER INFORMATION: wherein ASP is a D amino acid
<220> FEATURE:
<221> NAME/KEY: MISC_FEATURE
<222> LOCATION: (16)..(16)
<223> OTHER INFORMATION: wherein LEU is a D amino acid
<220> FEATURE:
<221> NAME/KEY: MISC_FEATURE
<222> LOCATION: (16)..(16)
<223> OTHER INFORMATION: wherein LEU at position 16 is attached to
      polyethylene glycol

<400> SEQUENCE: 17

Asn Asp Glu Cys Glu Leu Cys Val Asn Val Ala Cys Thr Gly Cys Leu
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (16)..(16)
<223> OTHER INFORMATION: wherein LEU at position 16 is attached to
      polyethylene glycol
<220> FEATURE:
<221> NAME/KEY: MISC_FEATURE
<222> LOCATION: (16)..(16)
<223> OTHER INFORMATION: wherein LEU is a D amino acid
```

```
<400> SEQUENCE: 18

Asn Asp Glu Cys Glu Leu Cys Val Asn Val Ala Cys Thr Gly Cys Leu
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (16)..(16)
<223> OTHER INFORMATION: wherein LEU is a D amino acid

<400> SEQUENCE: 19

Asn Asp Glu Cys Glu Leu Cys Val Asn Val Ala Cys Thr Gly Cys Leu
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (16)..(16)
<223> OTHER INFORMATION: wherein LEU is a D amino acid

<400> SEQUENCE: 20

Asn Asp Glu Cys Glu Leu Cys Val Asn Val Ala Cys Thr Gly Cys Leu
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein LEU at position 16 is attached to
      polyethylene glycol
<220> FEATURE:
<221> NAME/KEY: MISC_FEATURE
<222> LOCATION: (16)..(16)
<223> OTHER INFORMATION: wherein LEU is a D amino acid

<400> SEQUENCE: 21

Asn Asp Glu Cys Glu Leu Cys Val Asn Val Ala Cys Thr Gly Cys Leu
1               5                   10                  15

<210> SEQ ID NO 22
<211> LENGTH: 16
```

```
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (2)..(2)
<223> OTHER INFORMATION: wherein ASP is a D amino acid
<220> FEATURE:
<221> NAME/KEY: MISC_FEATURE
<222> LOCATION: (3)..(3)
<223> OTHER INFORMATION: wherein GLU is a D amino acid
<220> FEATURE:
<221> NAME/KEY: MISC_FEATURE
<222> LOCATION: (16)..(16)
<223> OTHER INFORMATION: wherein LEU is a D amino acid
<220> FEATURE:
<221> NAME/KEY: MISC_FEATURE
<222> LOCATION: (16)..(16)
<223> OTHER INFORMATION: wherein LEU at position 16 is attached to
      polyethylene glycol

<400> SEQUENCE: 22

Asn Asp Glu Cys Glu Leu Cys Val Asn Val Ala Cys Thr Gly Cys Leu
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (2)..(2)
<223> OTHER INFORMATION: wherein ASP is a D amino acid
<220> FEATURE:
<221> NAME/KEY: MISC_FEATURE
<222> LOCATION: (3)..(3)
<223> OTHER INFORMATION: wherein GLU is a D amino acid
<220> FEATURE:
<221> NAME/KEY: MISC_FEATURE
<222> LOCATION: (16)..(16)
<223> OTHER INFORMATION: wherein LEU is a D amino acid

<400> SEQUENCE: 23

Asn Asp Glu Cys Glu Leu Cys Val Asn Val Ala Cys Thr Gly Cys Leu
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
```

```
<222> LOCATION: (1)..(1)
<223> OTHER INFORMATION: wherein ASN is a D amino acid
<220> FEATURE:
<221> NAME/KEY: MISC_FEATURE
<222> LOCATION: (2)..(2)
<223> OTHER INFORMATION: wherein ASP is a D amino acid
<220> FEATURE:
<221> NAME/KEY: MISC_FEATURE
<222> LOCATION: (3)..(3)
<223> OTHER INFORMATION: wherein GLU is a D amino acid
<220> FEATURE:
<221> NAME/KEY: MISC_FEATURE
<222> LOCATION: (16)..(16)
<223> OTHER INFORMATION: wherein LEU at position 16 is attached to
      polyethylene glycol
<220> FEATURE:
<221> NAME/KEY: MISC_FEATURE
<222> LOCATION: (16)..(16)
<223> OTHER INFORMATION: wherein LEU is a D amino acid

<400> SEQUENCE: 24

Asn Asp Glu Cys Glu Leu Cys Val Asn Val Ala Cys Thr Gly Cys Leu
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (2)..(2)
<223> OTHER INFORMATION: wherein ASP is a D amino acid
<220> FEATURE:
<221> NAME/KEY: MISC_FEATURE
<222> LOCATION: (16)..(16)
<223> OTHER INFORMATION: wherein LEU at position 16 is attached to
      polyethylene glycol
<220> FEATURE:
<221> NAME/KEY: MISC_FEATURE
<222> LOCATION: (16)..(16)
<223> OTHER INFORMATION: wherein LEU is a D amino acid

<400> SEQUENCE: 25

Asn Asp Glu Cys Glu Leu Cys Val Asn Val Ala Cys Thr Gly Cys Leu
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (2)..(2)
<223> OTHER INFORMATION: wherein ASP is a D amino acid
<220> FEATURE:
<221> NAME/KEY: MISC_FEATURE
<222> LOCATION: (16)..(16)
<223> OTHER INFORMATION: wherein LEU is a D amino acid
```

<400> SEQUENCE: 26

Asn Asp Glu Cys Glu Leu Cys Val Asn Val Ala Cys Thr Gly Cys Leu
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (16)..(16)
<223> OTHER INFORMATION: wherein XAA is 3-(2-naphthyl)alanine
<220> FEATURE:
<221> NAME/KEY: MISC_FEATURE
<222> LOCATION: (16)..(16)
<223> OTHER INFORMATION: wherein XAA is a D amino acid

<400> SEQUENCE: 27

Asn Asp Glu Cys Glu Leu Cys Val Asn Val Ala Cys Thr Gly Cys Xaa
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (8)..(8)
<223> OTHER INFORMATION: wherein XAA is alpha-amino isobutyric acid
<220> FEATURE:
<221> NAME/KEY: MISC_FEATURE
<222> LOCATION: (10)..(10)
<223> OTHER INFORMATION: wherein XAA is alpha-amino isobutyric acid
<220> FEATURE:
<221> NAME/KEY: MISC_FEATURE
<222> LOCATION: (16)..(16)
<223> OTHER INFORMATION: wherein LEU is a D amino acid

<400> SEQUENCE: 28

Asn Asp Glu Cys Glu Leu Cys Xaa Asn Xaa Ala Cys Thr Gly Cys Leu
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (7)..(7)
<223> OTHER INFORMATION: wherein ASP at position 7 is attached to a
      Lactam bridge
<220> FEATURE:
<221> NAME/KEY: MISC_FEATURE
<222> LOCATION: (15)..(15)

```
<223> OTHER INFORMATION: wherein XAA is Ornithine
<220> FEATURE:
<221> NAME/KEY: MISC_FEATURE
<222> LOCATION: (16)..(16)
<223> OTHER INFORMATION: wherein LEU is a D amino acid

<400> SEQUENCE: 29

Asn Asp Glu Cys Glu Leu Asp Val Asn Val Ala Cys Thr Gly Xaa Leu
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (16)..(16)
<223> OTHER INFORMATION: wherein LEU is a D amino acid

<400> SEQUENCE: 30

Asn Asp Glu Cys Glu Tyr Cys Val Asn Val Ala Cys Thr Gly Cys Leu
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (16)..(16)
<223> OTHER INFORMATION: wherein LEU is a D amino acid

<400> SEQUENCE: 31

Asn Asp Glu Cys Glu Ser Cys Val Asn Val Ala Cys Thr Gly Cys Leu
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (16)..(16)
<223> OTHER INFORMATION: wherein LEU is a D amino acid
<220> FEATURE:
<221> NAME/KEY: MISC_FEATURE
<222> LOCATION: (16)..(16)
<223> OTHER INFORMATION: wherein LEU at position 16 is attached to
      polyethylene glycol
```

```
<400> SEQUENCE: 32

Asn Asp Glu Cys Glu Tyr Cys Val Asn Val Ala Cys Thr Gly Cys Leu
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (16)..(16)
<223> OTHER INFORMATION: wherein LEU is a D amino acid

<400> SEQUENCE: 33

Asn Asp Glu Cys Glu Tyr Cys Val Asn Val Ala Cys Thr Gly Cys Leu
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (16)..(16)
<223> OTHER INFORMATION: wherein LEU at position 16 is attached to
      polyethylene glycol
<220> FEATURE:
<221> NAME/KEY: MISC_FEATURE
<222> LOCATION: (16)..(16)
<223> OTHER INFORMATION: wherein LEU is a D amino acid

<400> SEQUENCE: 34

Asn Asp Glu Cys Glu Tyr Cys Val Asn Val Ala Cys Thr Gly Cys Leu
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (16)..(16)
<223> OTHER INFORMATION: wherein LEU is a D amino acid
<220> FEATURE:
<221> NAME/KEY: MISC_FEATURE
```

```
<222> LOCATION: (16)..(16)
<223> OTHER INFORMATION: wherein LEU at position 16 is attached to
      polyethylene glycol

<400> SEQUENCE: 35

Asn Asp Glu Cys Glu Ser Cys Val Asn Val Ala Cys Thr Gly Cys Leu
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (16)..(16)
<223> OTHER INFORMATION: wherein LEU is a D amino acid

<400> SEQUENCE: 36

Asn Asp Glu Cys Glu Ser Cys Val Asn Val Ala Cys Thr Gly Cys Leu
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (16)..(16)
<223> OTHER INFORMATION: wherein LEU at position 16 is attached to
      polyethylene glycol
<220> FEATURE:
<221> NAME/KEY: MISC_FEATURE
<222> LOCATION: (16)..(16)
<223> OTHER INFORMATION: wherein LEU is a D amino acid

<400> SEQUENCE: 37

Asn Asp Glu Cys Glu Ser Cys Val Asn Val Ala Cys Thr Gly Cys Leu
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 38

Asn Asp Glu Cys Glu Leu Cys Val Asn Val Ala Cys Thr Gly Cys Ser
1               5                   10                  15

<210> SEQ ID NO 39
<211> LENGTH: 16
<212> TYPE: PRT
<213> ORGANISM: Artificial Sequence
```

```
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (16)..(16)
<223> OTHER INFORMATION: wherein SER at position 16 is attached to
      polyethylene glycol

<400> SEQUENCE: 39

Asn Asp Glu Cys Glu Leu Cys Val Asn Val Ala Cys Thr Gly Cys Ser
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol

<400> SEQUENCE: 40

Asn Asp Glu Cys Glu Leu Cys Val Asn Val Ala Cys Thr Gly Cys Ser
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein SER at position 16 is attached to
      polyethylene glycol

<400> SEQUENCE: 41

Asn Asp Glu Cys Glu Leu Cys Val Asn Val Ala Cys Thr Gly Cys Ser
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (16)..(16)
<223> OTHER INFORMATION: wherein SER is a D amino acid
<220> FEATURE:
<221> NAME/KEY: MISC_FEATURE
<222> LOCATION: (16)..(16)
<223> OTHER INFORMATION: wherein SER at position 16 is attached to
      polyethylene glycol

<400> SEQUENCE: 42

Asn Asp Glu Cys Glu Leu Cys Val Asn Val Ala Cys Thr Gly Cys Ser
```

```
<210> SEQ ID NO 43
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (16)..(16)
<223> OTHER INFORMATION: wherein SER is a D amino acid

<400> SEQUENCE: 43

Asn Asp Glu Cys Glu Leu Cys Val Asn Val Ala Cys Thr Gly Cys Ser
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein SER at position 16 is attached to
      polyethylene glycol
<220> FEATURE:
<221> NAME/KEY: MISC_FEATURE
<222> LOCATION: (16)..(16)
<223> OTHER INFORMATION: wherein SER is a D amino acid

<400> SEQUENCE: 44

Asn Asp Glu Cys Glu Leu Cys Val Asn Val Ala Cys Thr Gly Cys Ser
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (5)..(6)
<223> OTHER INFORMATION: XAA is natural, unnatural, an analogue, L, D,
      or methylated amino acid or any combination
<220> FEATURE:
<221> NAME/KEY: MISC_FEATURE
<222> LOCATION: (8)..(11)
<223> OTHER INFORMATION: XAA is natural, unnatural, an analogue, L, D,
      or methylated amino acid or any combination
<220> FEATURE:
<221> NAME/KEY: MISC_FEATURE
<222> LOCATION: (13)..(14)
<223> OTHER INFORMATION: XAA is natural, unnatural, an analogue, L, D,
      or methylated amino acid or any combination
<220> FEATURE:
<221> NAME/KEY: MISC_FEATURE
<222> LOCATION: (16)..(16)
<223> OTHER INFORMATION: XAA is natural, unnatural, an analogue, L, D,
      or methylated amino acid or any combination

<400> SEQUENCE: 45

Asn Asp Glu Cys Xaa Xaa Cys Xaa Xaa Xaa Xaa Cys Xaa Xaa Cys Xaa
1               5                   10                  15
```

```
<210> SEQ ID NO 46
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: XAA is none or a natural, unnatural or an
      analogue amino acid, may be L, D, or a methylated amino acid, or
      any combination.
<220> FEATURE:
<221> NAME/KEY: MISC_FEATURE
<222> LOCATION: (2)..(2)
<223> OTHER INFORMATION: XAA is none or a natural, unnatural or an
      analogue amino acid, may be L, D, or a methylated amino acid, or
      any combination.
<220> FEATURE:
<221> NAME/KEY: MISC_FEATURE
<222> LOCATION: (3)..(3)
<223> OTHER INFORMATION: XAA is any natural, unnatural or an analogue
      amino acid, may be L, D, or a methylated amino acid, or any
      combination.
<220> FEATURE:
<221> NAME/KEY: MISC_FEATURE
<222> LOCATION: (5)..(6)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (8)..(11)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (13)..(14)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (16)..(16)
<223> OTHER INFORMATION: XAA is none or one natural, unnatural or an
      analogue amino acid, may be L, D, or a methylated amino acid, or
      any combination

<400> SEQUENCE: 46

Xaa Xaa Xaa Cys Xaa Xaa Cys Xaa Xaa Xaa Xaa Cys Xaa Xaa Cys Xaa
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: XAA is none or a natural, unnatural or an
      analogue amino acid, may be L, D, or a methylated amino acid or
      any combination thereof
<220> FEATURE:
<221> NAME/KEY: MISC_FEATURE
<222> LOCATION: (2)..(2)
<223> OTHER INFORMATION: XAA is none or a natural, unnatural or an
      analogue amino acid, may be L, D, or a methylated amino acid or
      any combination thereof
<220> FEATURE:
<221> NAME/KEY: MISC_FEATURE
<222> LOCATION: (3)..(3)
<223> OTHER INFORMATION: XAA is any natural, unnatural or an analogue
      amino acid, may be L, D, or a methylated amino acid or any
      combination thereof
<220> FEATURE:
<221> NAME/KEY: MISC_FEATURE
```

-continued

```
<222> LOCATION: (4)..(4)
<223> OTHER INFORMATION: XAA is a cysteine, penicillamine, homocysteine,
      or 3-mercaptoproline
<220> FEATURE:
<221> NAME/KEY: MISC_FEATURE
<222> LOCATION: (6)..(6)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (7)..(7)
<223> OTHER INFORMATION: XAA is a cysteine, penicillamine, homocysteine,
      or 3-mercaptoproline
<220> FEATURE:
<221> NAME/KEY: MISC_FEATURE
<222> LOCATION: (12)..(12)
<223> OTHER INFORMATION: XAA is a cysteine, penicillamine, homocysteine,
      or 3-mercaptoproline
<220> FEATURE:
<221> NAME/KEY: MISC_FEATURE
<222> LOCATION: (15)..(15)
<223> OTHER INFORMATION: XAA is a cysteine, penicillamine, homocysteine,
      or 3-mercaptoproline
<220> FEATURE:
<221> NAME/KEY: MISC_FEATURE
<222> LOCATION: (16)..(16)
<223> OTHER INFORMATION: XAA is natural, unnatural or an analogue, zero
      or one residue in length, may be L, D, or a methylated amino acid
      or any combination thereof

<400> SEQUENCE: 47

Xaa Xaa Xaa Xaa Glu Xaa Xaa Val Asn Val Ala Xaa Thr Gly Xaa Xaa
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: XAA is none or a natural, unnatural or an
      analogue amino acid, may be L, D, or a methylated amino acid or
      any combination thereof
<220> FEATURE:
<221> NAME/KEY: MISC_FEATURE
<222> LOCATION: (2)..(2)
<223> OTHER INFORMATION: XAA is none or a natural, unnatural or an
      analogue amino acid, may be L, D, or a methylated amino acid or
      any combination thereof
<220> FEATURE:
<221> NAME/KEY: MISC_FEATURE
<222> LOCATION: (3)..(3)
<223> OTHER INFORMATION: XAA is any natural, unnatural or an analogue
      amino acid, may be L, D, or a methylated amino acid or any
      combination thereof
<220> FEATURE:
<221> NAME/KEY: MISC_FEATURE
<222> LOCATION: (4)..(4)
<223> OTHER INFORMATION: XAA is a cysteine, penicillamine, homocysteine,
      or 3-mercaptoproline
<220> FEATURE:
<221> NAME/KEY: MISC_FEATURE
<222> LOCATION: (5)..(6)
<223> OTHER INFORMATION: XAA is any natural, unnatural or an analogue
      amino acid, may be L, D, or a methylated amino acid or any
      combination thereof
<220> FEATURE:
<221> NAME/KEY: MISC_FEATURE
<222> LOCATION: (7)..(7)
<223> OTHER INFORMATION: XAA is a cysteine, penicillamine, homocysteine,
      or 3-mercaptoproline
<220> FEATURE:
<221> NAME/KEY: MISC_FEATURE
<222> LOCATION: (8)..(11)
```

```
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (12)..(12)
<223> OTHER INFORMATION: XAA is a cysteine, penicillamine, homocysteine,
      or 3-mercaptoproline
<220> FEATURE:
<221> NAME/KEY: MISC_FEATURE
<222> LOCATION: (13)..(14)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (15)..(15)
<223> OTHER INFORMATION: XAA is a cysteine, penicillamine, homocysteine,
      or 3-mercaptoproline
<220> FEATURE:
<221> NAME/KEY: MISC_FEATURE
<222> LOCATION: (16)..(16)
<223> OTHER INFORMATION: XAA is natural, unnatural or an analogue, zero
      or one residue in length, may be L, D, or a methylated amino acid
      or any combination thereof

<400> SEQUENCE: 48

Xaa Xaa Xaa Xaa Xaa Xaa Xaa Xaa Xaa Xaa Xaa Xaa Xaa Xaa Xaa Xaa
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (5)..(6)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (8)..(8)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (10)..(11)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (13)..(14)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (16)..(16)
<223> OTHER INFORMATION: XAA is natural, unnatural, analogue, L, D, or
      methylated amino acid or any combination

<400> SEQUENCE: 49

Asn Asp Asp Cys Xaa Xaa Cys Xaa Asn Xaa Xaa Cys Xaa Xaa Cys Xaa
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
```

```
<221> NAME/KEY: MISC_FEATURE
<222> LOCATION: (5)..(6)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (8)..(8)
<223> OTHER INFORMATION: XAA is any natural, unnatural, analogue, L, D,
      or methylated amino acid or any combination
<220> FEATURE:
<221> NAME/KEY: MISC_FEATURE
<222> LOCATION: (10)..(11)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (13)..(14)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (16)..(16)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (16)..(16)
<223> OTHER INFORMATION: XAA is a D amino acid

<400> SEQUENCE: 50

Asn Glu Glu Cys Xaa Xaa Cys Xaa Asn Xaa Xaa Cys Xaa Xaa Cys Xaa
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (2)..(2)
<223> OTHER INFORMATION: wherein GLU is a D amino acid
<220> FEATURE:
<221> NAME/KEY: MISC_FEATURE
<222> LOCATION: (5)..(6)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (8)..(8)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (10)..(11)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (13)..(14)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (16)..(16)
<223> OTHER INFORMATION: XAA is a D amino acid
<220> FEATURE:
<221> NAME/KEY: MISC_FEATURE
<222> LOCATION: (16)..(16)
<223> OTHER INFORMATION: x is natural, unnatural, analogue, L, D, or
      methylated amino acid or any combination
```

```
<400> SEQUENCE: 51

Asn Glu Asp Cys Xaa Xaa Cys Xaa Asn Xaa Xaa Cys Xaa Xaa Cys Xaa
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (2)..(2)
<223> OTHER INFORMATION: wherein ASP is a D amino acid
<220> FEATURE:
<221> NAME/KEY: MISC_FEATURE
<222> LOCATION: (5)..(6)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (8)..(8)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (10)..(11)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (13)..(14)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (16)..(16)
<223> OTHER INFORMATION: XAA is a D amino acid
<220> FEATURE:
<221> NAME/KEY: MISC_FEATURE
<222> LOCATION: (16)..(16)
<223> OTHER INFORMATION: XAA is natural, unnatural, analogue, L, D, or
      methylated amino acid or any combination

<400> SEQUENCE: 52

Asn Asp Glu Cys Xaa Xaa Cys Xaa Asn Xaa Xaa Cys Xaa Xaa Cys Xaa
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (2)..(2)
<223> OTHER INFORMATION: wherein ASP is a D amino acid
<220> FEATURE:
<221> NAME/KEY: MISC_FEATURE
<222> LOCATION: (3)..(3)
<223> OTHER INFORMATION: wherein GLU is a D amino acid
<220> FEATURE:
<221> NAME/KEY: MISC_FEATURE
<222> LOCATION: (5)..(6)
<223> OTHER INFORMATION: XAA is natural, unnatural, analogue, L, D, or
      methylated amino acid or any combination
```

```
<220> FEATURE:
<221> NAME/KEY: MISC_FEATURE
<222> LOCATION: (8)..(8)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (10)..(11)
<223> OTHER INFORMATION: x is natural, unnatural, analogue, L, D, or
      methylated amino acid or any combination
<220> FEATURE:
<221> NAME/KEY: MISC_FEATURE
<222> LOCATION: (13)..(14)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (16)..(16)
<223> OTHER INFORMATION: XAA is a D amino acid
<220> FEATURE:
<221> NAME/KEY: MISC_FEATURE
<222> LOCATION: (16)..(16)
<223> OTHER INFORMATION: XAA is natural, unnatural, analogue, L, D, or
      methylated amino acid or any combination

<400> SEQUENCE: 53

Asn Asp Glu Cys Xaa Xaa Cys Xaa Tyr Xaa Xaa Cys Xaa Xaa Cys Xaa
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (2)..(2)
<223> OTHER INFORMATION: wherein GLU is a D amino acid
<220> FEATURE:
<221> NAME/KEY: MISC_FEATURE
<222> LOCATION: (3)..(3)
<223> OTHER INFORMATION: wherein GLU is a D amino acid
<220> FEATURE:
<221> NAME/KEY: MISC_FEATURE
<222> LOCATION: (5)..(6)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (8)..(8)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (10)..(11)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (13)..(14)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (16)..(16)
<223> OTHER INFORMATION: XAA is a D amino acid
<220> FEATURE:
<221> NAME/KEY: MISC_FEATURE
<222> LOCATION: (16)..(16)
<223> OTHER INFORMATION: x is natural, unnatural, analogue, L, D, or
      methylated amino acid or any combination
```

<400> SEQUENCE: 54

Asn Glu Glu Cys Xaa Xaa Cys Xaa Tyr Xaa Xaa Cys Xaa Xaa Cys Xaa
1               5                   10                  15

<210> SEQ ID NO 55
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 55

Cys Cys Glu Tyr Cys Cys Asn Pro Ala Cys Thr Gly Cys Tyr
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 56

Cys Cys Glu Tyr Cys Cys Asn Pro Ala Cys Thr Gly Cys
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein CYS at position 1 is attached to
      polyethylene glycol
<220> FEATURE:
<221> NAME/KEY: MISC_FEATURE
<222> LOCATION: (14)..(14)
<223> OTHER INFORMATION: wherein TYR at position 14 is attached to
      polyethylene glycol

<400> SEQUENCE: 57

Cys Cys Glu Tyr Cys Cys Asn Pro Ala Cys Thr Gly Cys Tyr
1               5                   10

<210> SEQ ID NO 58
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 58

Asn Phe Cys Cys Glu Ser Cys Cys Asn Pro Ala Cys Thr Gly Cys Tyr
1               5                   10                  15

<210> SEQ ID NO 59
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 59

Asn Phe Cys Cys Glu Phe Cys Cys Asn Pro Ala Cys Thr Gly Cys Tyr
1               5                   10                  15

```
<210> SEQ ID NO 60
<211> LENGTH: 14
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (14)..(14)
<223> OTHER INFORMATION: wherein TYR is a D amino acid

<400> SEQUENCE: 60

Cys Cys Glu Tyr Cys Cys Asn Pro Ala Cys Thr Gly Cys Tyr
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein CYS at position 1 is attached to
      polyethylene glycol

<400> SEQUENCE: 61

Cys Cys Glu Tyr Cys Cys Asn Pro Ala Cys Thr Gly Cys Tyr
1               5                   10

<210> SEQ ID NO 62
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 62

Asn Phe Cys Cys Glu Thr Cys Cys Asn Pro Ala Cys Thr Gly Cys Tyr
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein TYR is a D amino acid

<400> SEQUENCE: 63

Asn Phe Cys Cys Glu Ser Cys Cys Asn Pro Ala Cys Thr Gly Cys Tyr
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid

<400> SEQUENCE: 64
```

Asn Phe Cys Cys Glu Ser Cys Cys Asn Pro Ala Cys Thr Gly Cys Tyr
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (16)..(16)
<223> OTHER INFORMATION: wherein TYR is a D amino acid

<400> SEQUENCE: 65

Asn Phe Cys Cys Glu Ser Cys Cys Asn Pro Ala Cys Thr Gly Cys Tyr
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein TYR is a D amino acid

<400> SEQUENCE: 66

Asn Phe Cys Cys Glu Thr Cys Cys Asn Pro Ala Cys Thr Gly Cys Tyr
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid

<400> SEQUENCE: 67

Asn Phe Cys Cys Glu Thr Cys Cys Asn Pro Ala Cys Thr Gly Cys Tyr
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (16)..(16)
<223> OTHER INFORMATION: wherein TYR is a D amino acid

<400> SEQUENCE: 68

Asn Phe Cys Cys Glu Thr Cys Cys Asn Pro Ala Cys Thr Gly Cys Tyr
1               5                   10                  15

```
<210> SEQ ID NO 69
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein TYR is a D amino acid

<400> SEQUENCE: 69

Asn Phe Cys Cys Glu Phe Cys Cys Asn Pro Ala Cys Thr Gly Cys Tyr
1               5                   10                  15

<210> SEQ ID NO 70
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid

<400> SEQUENCE: 70

Asn Phe Cys Cys Glu Phe Cys Cys Asn Pro Ala Cys Thr Gly Cys Tyr
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (16)..(16)
<223> OTHER INFORMATION: wherein TYR is a D amino acid

<400> SEQUENCE: 71

Asn Phe Cys Cys Glu Phe Cys Cys Asn Pro Ala Cys Thr Gly Cys Tyr
1               5                   10                  15

<210> SEQ ID NO 72
<211> LENGTH: 14
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (14)..(14)
<223> OTHER INFORMATION: wherein TYR at position 14 is attached to
      polyethylene glycol

<400> SEQUENCE: 72

Cys Cys Glu Tyr Cys Cys Asn Pro Ala Cys Thr Gly Cys Tyr
1               5                   10

<210> SEQ ID NO 73
<211> LENGTH: 13
<212> TYPE: PRT
<213> ORGANISM: Artificial Sequence
```

```
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein CYS at position 1 is attached to
      polyethylene glycol
<220> FEATURE:
<221> NAME/KEY: MISC_FEATURE
<222> LOCATION: (13)..(13)
<223> OTHER INFORMATION: wherein CYS at position 13 is attached to
      polyethylene glycol

<400> SEQUENCE: 73

Cys Cys Glu Tyr Cys Cys Asn Pro Ala Cys Thr Gly Cys
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein CYS at position 1 is attached to
      polyethylene glycol

<400> SEQUENCE: 74

Cys Cys Glu Tyr Cys Cys Asn Pro Ala Cys Thr Gly Cys
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (13)..(13)
<223> OTHER INFORMATION: wherein CYS at position 13 is attached to
      polyethylene glycol

<400> SEQUENCE: 75

Cys Cys Glu Tyr Cys Cys Asn Pro Ala Cys Thr Gly Cys
1               5                   10

<210> SEQ ID NO 76
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (16)..(16)
<223> OTHER INFORMATION: wherein TYR at position 16 is attached to
      polyethylene glycol

<400> SEQUENCE: 76

Asn Phe Cys Cys Glu Ser Cys Cys Asn Pro Ala Cys Thr Gly Cys Tyr
1               5                   10                  15

<210> SEQ ID NO 77
```

```
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol

<400> SEQUENCE: 77

Asn Phe Cys Cys Glu Ser Cys Cys Asn Pro Ala Cys Thr Gly Cys Tyr
1               5                   10                  15

<210> SEQ ID NO 78
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein TYR at position 16 is attached to
      polyethylene glycol

<400> SEQUENCE: 78

Asn Phe Cys Cys Glu Ser Cys Cys Asn Pro Ala Cys Thr Gly Cys Tyr
1               5                   10                  15

<210> SEQ ID NO 79
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (16)..(16)
<223> OTHER INFORMATION: wherein TYR at position 16 is attached to
      polyethylene glycol

<400> SEQUENCE: 79

Asn Phe Cys Cys Glu Phe Cys Cys Asn Pro Ala Cys Thr Gly Cys Tyr
1               5                   10                  15

<210> SEQ ID NO 80
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol

<400> SEQUENCE: 80

Asn Phe Cys Cys Glu Phe Cys Cys Asn Pro Ala Cys Thr Gly Cys Tyr
1               5                   10                  15

<210> SEQ ID NO 81
<211> LENGTH: 16
<212> TYPE: PRT
```

```
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein TYR at position 16 is attached to
      polyethylene glycol

<400> SEQUENCE: 81

Asn Phe Cys Cys Glu Phe Cys Cys Asn Pro Ala Cys Thr Gly Cys Tyr
1               5                   10                  15

<210> SEQ ID NO 82
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol
<220> FEATURE:
<221> NAME/KEY: MISC_FEATURE
<222> LOCATION: (16)..(16)
<223> OTHER INFORMATION: wherein TYR at position 16 is attached to
      polyethylene glycol

<400> SEQUENCE: 82

Asn Phe Cys Cys Glu Tyr Cys Cys Asn Pro Ala Cys Thr Gly Cys Tyr
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN at position 1 is attached to
      polyethylene glycol

<400> SEQUENCE: 83

Asn Phe Cys Cys Glu Tyr Cys Cys Asn Pro Ala Cys Thr Gly Cys Tyr
1               5                   10                  15

<210> SEQ ID NO 84
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein TYR at position 16 is attached to
      polyethylene glycol

<400> SEQUENCE: 84

Asn Phe Cys Cys Glu Tyr Cys Cys Asn Pro Ala Cys Thr Gly Cys Tyr
1               5                   10                  15

<210> SEQ ID NO 85
<211> LENGTH: 14
<212> TYPE: PRT
<213> ORGANISM: Artificial Sequence
<220> FEATURE:
```

```
<223> OTHER INFORMATION: Chemically Synthesized

<400> SEQUENCE: 85

Cys Cys Glu Ser Cys Cys Asn Pro Ala Cys Thr Gly Cys Tyr
1               5                   10

<210> SEQ ID NO 86
<211> LENGTH: 14
<212> TYPE: PRT
<213> ORGANISM: Artificial Sequence
<220> FEATURE:
<223> OTHER INFORMATION: Chemically Synthesized

<400> SEQUENCE: 86

Cys Cys Glu Phe Cys Cys Asn Pro Ala Cys Thr Gly Cys Tyr
1               5                   10

<210> SEQ ID NO 87
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 87

Cys Cys Glu Ser Cys Cys Asn Pro Ala Cys Thr Gly Cys
1               5                   10

<210> SEQ ID NO 88
<211> LENGTH: 13
<212> TYPE: PRT
<213> ORGANISM: Artificial Sequence
<220> FEATURE:
<223> OTHER INFORMATION: Chemically Synthesized

<400> SEQUENCE: 88

Cys Cys Glu Phe Cys Cys Asn Pro Ala Cys Thr Gly Cys
1               5                   10

<210> SEQ ID NO 89
<211> LENGTH: 14
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(2)
<223> OTHER INFORMATION: wherein XAA is penicillamine
<220> FEATURE:
<221> NAME/KEY: MISC_FEATURE
<222> LOCATION: (5)..(6)
<223> OTHER INFORMATION: wherein XAA is penicillamine
<220> FEATURE:
<221> NAME/KEY: MISC_FEATURE
<222> LOCATION: (10)..(10)
<223> OTHER INFORMATION: wherein XAA is penicillamine
<220> FEATURE:
<221> NAME/KEY: MISC_FEATURE
<222> LOCATION: (13)..(13)
<223> OTHER INFORMATION: wherein XAA is penicillamine

<400> SEQUENCE: 89

Xaa Xaa Glu Tyr Xaa Xaa Asn Pro Ala Xaa Thr Gly Xaa Tyr
1               5                   10

<210> SEQ ID NO 90
<211> LENGTH: 13
<212> TYPE: PRT
```

```
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(2)
<223> OTHER INFORMATION: wherein XAA is penicillamine
<220> FEATURE:
<221> NAME/KEY: MISC_FEATURE
<222> LOCATION: (5)..(6)
<223> OTHER INFORMATION: wherein XAA is penicillamine
<220> FEATURE:
<221> NAME/KEY: MISC_FEATURE
<222> LOCATION: (10)..(10)
<223> OTHER INFORMATION: wherein XAA is penicillamine
<220> FEATURE:
<221> NAME/KEY: MISC_FEATURE
<222> LOCATION: (13)..(13)
<223> OTHER INFORMATION: wherein XAA is penicillamine

<400> SEQUENCE: 90

Xaa Xaa Glu Tyr Xaa Xaa Asn Pro Ala Xaa Thr Gly Xaa
 1               5                  10

<210> SEQ ID NO 91
<211> LENGTH: 22
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(6)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (11)..(11)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (15)..(17)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (19)..(20)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (22)..(22)
<223> OTHER INFORMATION: XAA is natural, unnatural, analogue, L, D, or
      methylated amino acid or any combination

<400> SEQUENCE: 91

Xaa Xaa Xaa Xaa Xaa Xaa Asn Tyr Cys Cys Xaa Tyr Cys Cys Xaa Xaa
 1               5                  10                  15

Xaa Cys Xaa Xaa Cys Xaa
                 20

<210> SEQ ID NO 92
<211> LENGTH: 22
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(6)
<223> OTHER INFORMATION: XAA is natural, unnatural, analogue, L, D, or
      methylated amino acid or any combination
<220> FEATURE:
```

```
<221> NAME/KEY: MISC_FEATURE
<222> LOCATION: (11)..(11)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (15)..(17)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (19)..(20)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (22)..(22)
<223> OTHER INFORMATION: XAA is natural, unnatural, analogue, L, D, or
      methylated amino acid or any combination

<400> SEQUENCE: 92

Xaa Xaa Xaa Xaa Xaa Xaa Asn Phe Cys Cys Xaa Phe Cys Cys Xaa Xaa
1               5                   10                  15

Xaa Cys Xaa Xaa Cys Xaa
            20

<210> SEQ ID NO 93
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (5)..(5)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (9)..(11)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (13)..(14)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (16)..(16)
<223> OTHER INFORMATION: XAA is natural, unnatural, analogue, L, D, or
      methylated amino acid or any combination

<400> SEQUENCE: 93

Asn Phe Cys Cys Xaa Phe Cys Cys Xaa Xaa Xaa Cys Xaa Xaa Cys Xaa
1               5                   10                  15

<210> SEQ ID NO 94
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (3)..(3)
<223> OTHER INFORMATION: wherein XAA is penicillamine
<220> FEATURE:
<221> NAME/KEY: MISC_FEATURE
<222> LOCATION: (5)..(5)
<223> OTHER INFORMATION: XAA is natural, unnatural, analogue, L, D, or
      methylated amino acid or any combination
<220> FEATURE:
<221> NAME/KEY: MISC_FEATURE
```

```
<222> LOCATION: (8)..(8)
<223> OTHER INFORMATION: wherein XAA is penicillamine
<220> FEATURE:
<221> NAME/KEY: MISC_FEATURE
<222> LOCATION: (9)..(11)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (13)..(14)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (16)..(16)
<223> OTHER INFORMATION: XAA is natural, unnatural, analogue, L, D, or
      methylated amino acid or any combination

<400> SEQUENCE: 94

Asn Phe Xaa Cys Xaa Phe Cys Xaa Xaa Xaa Xaa Cys Xaa Xaa Cys Xaa
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (3)..(4)
<223> OTHER INFORMATION: wherein XAA is a cysteine, penicillamine,
      homocysteine, or 3-mercaptoproline
<220> FEATURE:
<221> NAME/KEY: MISC_FEATURE
<222> LOCATION: (5)..(6)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (7)..(8)
<223> OTHER INFORMATION: wherein XAA is a cysteine, penicillamine,
      homocysteine, or 3-mercaptoproline
<220> FEATURE:
<221> NAME/KEY: MISC_FEATURE
<222> LOCATION: (9)..(11)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (12)..(12)
<223> OTHER INFORMATION: wherein XAA is a cysteine, penicillamine,
      homocysteine, or 3-mercaptoproline
<220> FEATURE:
<221> NAME/KEY: MISC_FEATURE
<222> LOCATION: (13)..(14)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (15)..(15)
<223> OTHER INFORMATION: wherein XAA is a cysteine, penicillamine,
      homocysteine, or 3-mercaptoproline
<220> FEATURE:
<221> NAME/KEY: MISC_FEATURE
<222> LOCATION: (16)..(16)
<223> OTHER INFORMATION: XAA is natural, unnatural, analogue, L, D, or
      methylated amino acid or any combination

<400> SEQUENCE: 95

Asn Phe Xaa Xaa Xaa Xaa Xaa Xaa Xaa Xaa Xaa Xaa Xaa Xaa Xaa Xaa
1               5                   10                  15

<210> SEQ ID NO 96
<211> LENGTH: 14
```

```
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(2)
<223> OTHER INFORMATION: wherein XAA is a cysteine, penicillamine,
      homocysteine, or 3-mercaptoproline
<220> FEATURE:
<221> NAME/KEY: MISC_FEATURE
<222> LOCATION: (4)..(4)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (5)..(6)
<223> OTHER INFORMATION: wherein XAA is a cysteine, penicillamine,
      homocysteine, or 3-mercaptoproline
<220> FEATURE:
<221> NAME/KEY: MISC_FEATURE
<222> LOCATION: (10)..(10)
<223> OTHER INFORMATION: wherein XAA is a cysteine, penicillamine,
      homocysteine, or 3-mercaptoproline
<220> FEATURE:
<221> NAME/KEY: MISC_FEATURE
<222> LOCATION: (13)..(13)
<223> OTHER INFORMATION: wherein XAA is a cysteine, penicillamine,
      homocysteine, or 3-mercaptoproline

<400> SEQUENCE: 96

Xaa Xaa Glu Xaa Xaa Xaa Asn Pro Ala Xaa Thr Gly Xaa Tyr
1               5                   10

<210> SEQ ID NO 97
<211> LENGTH: 13
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(2)
<223> OTHER INFORMATION: wherein XAA is a cysteine, penicillamine,
      homocysteine, or 3-mercaptoproline
<220> FEATURE:
<221> NAME/KEY: MISC_FEATURE
<222> LOCATION: (4)..(4)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (5)..(6)
<223> OTHER INFORMATION: wherein XAA is a cysteine, penicillamine,
      homocysteine, or 3-mercaptoproline
<220> FEATURE:
<221> NAME/KEY: MISC_FEATURE
<222> LOCATION: (10)..(10)
<223> OTHER INFORMATION: wherein XAA is a cysteine, penicillamine,
      homocysteine, or 3-mercaptoproline
<220> FEATURE:
<221> NAME/KEY: MISC_FEATURE
<222> LOCATION: (13)..(13)
<223> OTHER INFORMATION: wherein XAA is a cysteine, penicillamine,
      homocysteine, or 3-mercaptoproline

<400> SEQUENCE: 97

Xaa Xaa Glu Xaa Xaa Xaa Asn Pro Ala Xaa Thr Gly Xaa
1               5                   10

<210> SEQ ID NO 98
<211> LENGTH: 20
<212> TYPE: PRT
<213> ORGANISM: Artificial Sequence
<220> FEATURE:
```

```
<223> OTHER INFORMATION: Chemically Synthesized
<220> FEATURE:
<221> NAME/KEY: MISC_FEATURE
<222> LOCATION: (1)..(1)
<223> OTHER INFORMATION: XAA is none or a natural, unnatural, analogue,
      L, D, or methylated amino acid or any combination
<220> FEATURE:
<221> NAME/KEY: MISC_FEATURE
<222> LOCATION: (2)..(2)
<223> OTHER INFORMATION: XAA is none or a natural, unnatural, analogue,
      L, D, or methylated amino acid or any combination
<220> FEATURE:
<221> NAME/KEY: MISC_FEATURE
<222> LOCATION: (3)..(3)
<223> OTHER INFORMATION: XAA is none or a natural, unnatural, analogue,
      L, D, or methylated amino acid or any combination
<220> FEATURE:
<221> NAME/KEY: MISC_FEATURE
<222> LOCATION: (4)..(4)
<223> OTHER INFORMATION: XAA is none or a natural, unnatural, analogue,
      L, D, or methylated amino acid or any combination
<220> FEATURE:
<221> NAME/KEY: MISC_FEATURE
<222> LOCATION: (5)..(5)
<223> OTHER INFORMATION: XAA is none or a natural, unnatural, analogue,
      L, D, or methylated amino acid or any combination
<220> FEATURE:
<221> NAME/KEY: MISC_FEATURE
<222> LOCATION: (6)..(6)
<223> OTHER INFORMATION: XAA is none or a natural, unnatural, analogue,
      L, D, or methylated amino acid or any combination
<220> FEATURE:
<221> NAME/KEY: MISC_FEATURE
<222> LOCATION: (7)..(8)
<223> OTHER INFORMATION: wherein XAA is a cysteine, penicillamine,
      homocysteine, or 3-mercaptoproline
<220> FEATURE:
<221> NAME/KEY: MISC_FEATURE
<222> LOCATION: (9)..(10)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (11)..(12)
<223> OTHER INFORMATION: wherein XAA is a cysteine, penicillamine,
      homocysteine, or 3-mercaptoproline
<220> FEATURE:
<221> NAME/KEY: MISC_FEATURE
<222> LOCATION: (13)..(15)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (16)..(16)
<223> OTHER INFORMATION: wherein XAA is a cysteine, penicillamine,
      homocysteine, or 3-mercaptoproline
<220> FEATURE:
<221> NAME/KEY: MISC_FEATURE
<222> LOCATION: (17)..(18)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (19)..(19)
<223> OTHER INFORMATION: wherein XAA is a cysteine, penicillamine,
      homocysteine, or 3-mercaptoproline
<220> FEATURE:
<221> NAME/KEY: MISC_FEATURE
<222> LOCATION: (20)..(20)
<223> OTHER INFORMATION: XAA is none or a natural, unnatural, analogue,
      L, D, or methylated amino acid or any combination

<400> SEQUENCE: 98

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa
            20
```

```
<210> SEQ ID NO 99
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (16)..(16)
<223> OTHER INFORMATION: wherein LEU is a D amino acid
<220> FEATURE:
<221> NAME/KEY: MISC_FEATURE
<222> LOCATION: (16)..(16)
<223> OTHER INFORMATION: wherein LEU is conjugated to an AMIDE

<400> SEQUENCE: 99

Asn Asp Glu Cys Glu Leu Cys Val Asn Val Ala Cys Thr Gly Cys Leu
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (16)..(16)
<223> OTHER INFORMATION: wherein SER is a D amino acid

<400> SEQUENCE: 100

Asn Asp Glu Cys Glu Leu Cys Val Asn Val Ala Cys Thr Gly Cys Ser
1               5                   10                  15

<210> SEQ ID NO 101
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (16)..(16)
<223> OTHER INFORMATION: wherein SER is a D amino acid
<220> FEATURE:
<221> NAME/KEY: MISC_FEATURE
<222> LOCATION: (16)..(16)
<223> OTHER INFORMATION: wherein SER is conjugated to an AMIDE

<400> SEQUENCE: 101

Asn Asp Glu Cys Glu Leu Cys Val Asn Val Ala Cys Thr Gly Cys Ser
1               5                   10                  15

<210> SEQ ID NO 102
<211> LENGTH: 16
<212> TYPE: PRT
<213> ORGANISM: Artificial Sequence
<220> FEATURE:
<223> OTHER INFORMATION: Chemically Synthesized
```

```
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (16)..(16)
<223> OTHER INFORMATION: wherein TYR is a D amino acid

<400> SEQUENCE: 102

Asn Asp Glu Cys Glu Leu Cys Val Asn Val Ala Cys Thr Gly Cys Tyr
1               5                   10                  15

<210> SEQ ID NO 103
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (16)..(16)
<223> OTHER INFORMATION: wherein TYR is a D amino acid
<220> FEATURE:
<221> NAME/KEY: MISC_FEATURE
<222> LOCATION: (16)..(16)
<223> OTHER INFORMATION: wherein TYR is conjugated to an AMIDE

<400> SEQUENCE: 103

Asn Asp Glu Cys Glu Leu Cys Val Asn Val Ala Cys Thr Gly Cys Tyr
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein GLU is conjugated to Py
<220> FEATURE:
<221> NAME/KEY: MISC_FEATURE
<222> LOCATION: (16)..(16)
<223> OTHER INFORMATION: wherein LEU is conjugated to an AMIDE
<220> FEATURE:
<221> NAME/KEY: MISC_FEATURE
<222> LOCATION: (16)..(16)
<223> OTHER INFORMATION: wherein LEU is a D amino acid

<400> SEQUENCE: 104

Glu Asp Glu Cys Glu Leu Cys Val Asn Val Ala Cys Thr Gly Cys Leu
1               5                   10                  15

<210> SEQ ID NO 105
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is attached to polyethylene glycol
<220> FEATURE:
<221> NAME/KEY: MISC_FEATURE
<222> LOCATION: (16)..(16)
<223> OTHER INFORMATION: wherein LEU is attached to polyethylene glycol
```

-continued

```
<400> SEQUENCE: 105

Asn Asp Glu Cys Glu Leu Cys Val Asn Val Ala Cys Thr Gly Cys Leu
1               5                   10                  15

<210> SEQ ID NO 106
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is attached to polyethylene glycol

<400> SEQUENCE: 106

Asn Asp Glu Cys Glu Leu Cys Val Asn Val Ala Cys Thr Gly Cys Leu
1               5                   10                  15

<210> SEQ ID NO 107
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein LEU is attached to polyethylene glycol

<400> SEQUENCE: 107

Asn Asp Glu Cys Glu Leu Cys Val Asn Val Ala Cys Thr Gly Cys Leu
1               5                   10                  15

<210> SEQ ID NO 108
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(3)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (4)..(4)
<223> OTHER INFORMATION: wherein XAA is a cysteine, penicillamine,
      homocysteine, or 3-mercaptoproline
<220> FEATURE:
<221> NAME/KEY: MISC_FEATURE
<222> LOCATION: (5)..(6)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (7)..(7)
<223> OTHER INFORMATION: wherein XAA is a cysteine, penicillamine,
      homocysteine, or 3-mercaptoproline
<220> FEATURE:
<221> NAME/KEY: MISC_FEATURE
<222> LOCATION: (8)..(11)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (12)..(12)
<223> OTHER INFORMATION: wherein XAA is a cysteine, penicillamine,
      homocysteine, or 3-mercaptoproline
<220> FEATURE:
<221> NAME/KEY: MISC_FEATURE
```

```
<222> LOCATION: (13)..(14)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (15)..(15)
<223> OTHER INFORMATION: wherein XAA is a cysteine, penicillamine,
      homocysteine, or 3-mercaptoproline
<220> FEATURE:
<221> NAME/KEY: MISC_FEATURE
<222> LOCATION: (16)..(16)
<223> OTHER INFORMATION: XAA is natural, unnatural, analogue, L, D, or
      methylated amino acid or any combination

<400> SEQUENCE: 108

Xaa Xaa Xaa Xaa Xaa Xaa Xaa Xaa Xaa Xaa Xaa Xaa Xaa Xaa Xaa Xaa
1               5                   10                  15

<210> SEQ ID NO 109
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 109

Asn Asp Asp Cys Glu Leu Cys Val Asn Val Ala Cys Thr Gly Cys Leu
1               5                   10                  15

<210> SEQ ID NO 110
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 110

Glu Asp Asp Cys Glu Leu Cys Val Asn Val Ala Cys Thr Gly Cys Leu
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 111

Glu Asp Glu Cys Glu Leu Cys Val Asn Val Ala Cys Thr Gly Cys Leu
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 112

Glu Glu Asp Cys Glu Leu Cys Val Asn Val Ala Cys Thr Gly Cys Leu
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: Chemically Synthesized
```

```
<400> SEQUENCE: 113

Glu Glu Glu Cys Glu Leu Cys Val Asn Val Ala Cys Thr Gly Cys Leu
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 114

Asp Asp Asp Cys Glu Leu Cys Val Asn Val Ala Cys Thr Gly Cys Leu
1               5                   10                  15

<210> SEQ ID NO 115
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 115

Asp Asp Glu Cys Glu Leu Cys Val Asn Val Ala Cys Thr Gly Cys Leu
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 116

Asp Glu Asp Cys Glu Leu Cys Val Asn Val Ala Cys Thr Gly Cys Leu
1               5                   10                  15

<210> SEQ ID NO 117
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 117

Asp Glu Glu Cys Glu Leu Cys Val Asn Val Ala Cys Thr Gly Cys Leu
1               5                   10                  15

<210> SEQ ID NO 118
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 118

Gln Asp Asp Cys Glu Leu Cys Val Asn Val Ala Cys Thr Gly Cys Leu
1               5                   10                  15

<210> SEQ ID NO 119
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 119
```

```
Gln Asp Glu Cys Glu Leu Cys Val Asn Val Ala Cys Thr Gly Cys Leu
1               5                   10                  15
```

<210> SEQ ID NO 120
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 120

```
Gln Glu Asp Cys Glu Leu Cys Val Asn Val Ala Cys Thr Gly Cys Leu
1               5                   10                  15
```

<210> SEQ ID NO 121
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 121

```
Gln Glu Glu Cys Glu Leu Cys Val Asn Val Ala Cys Thr Gly Cys Leu
1               5                   10                  15
```

<210> SEQ ID NO 122
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 122

```
Lys Asp Asp Cys Glu Leu Cys Val Asn Val Ala Cys Thr Gly Cys Leu
1               5                   10                  15
```

<210> SEQ ID NO 123
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 123

```
Lys Asp Glu Cys Glu Leu Cys Val Asn Val Ala Cys Thr Gly Cys Leu
1               5                   10                  15
```

<210> SEQ ID NO 124
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 124

```
Lys Glu Asp Cys Glu Leu Cys Val Asn Val Ala Cys Thr Gly Cys Leu
1               5                   10                  15
```

<210> SEQ ID NO 125
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 125

```
Lys Glu Glu Cys Glu Leu Cys Val Asn Val Ala Cys Thr Gly Cys Leu
1               5                   10                  15
```

<210> SEQ ID NO 126
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 126

```
Glu Asp Asp Cys Glu Leu Cys Val Asn Val Ala Cys Thr Gly Cys Ser
1               5                   10                  15
```

<210> SEQ ID NO 127
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 127

```
Glu Asp Glu Cys Glu Leu Cys Val Asn Val Ala Cys Thr Gly Cys Ser
1               5                   10                  15
```

<210> SEQ ID NO 128
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 128

```
Glu Glu Asp Cys Glu Leu Cys Val Asn Val Ala Cys Thr Gly Cys Ser
1               5                   10                  15
```

<210> SEQ ID NO 129
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 129

```
Glu Glu Glu Cys Glu Leu Cys Val Asn Val Ala Cys Thr Gly Cys Ser
1               5                   10                  15
```

<210> SEQ ID NO 130
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 130

```
Asp Asp Asp Cys Glu Leu Cys Val Asn Val Ala Cys Thr Gly Cys Ser
1               5                   10                  15
```

<210> SEQ ID NO 131
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 131

```
Asp Asp Glu Cys Glu Leu Cys Val Asn Val Ala Cys Thr Gly Cys Ser
```

```
<210> SEQ ID NO 132
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 132

Asp Glu Asp Cys Glu Leu Cys Val Asn Val Ala Cys Thr Gly Cys Ser
1               5                   10                  15

<210> SEQ ID NO 133
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 133

Asp Glu Glu Cys Glu Leu Cys Val Asn Val Ala Cys Thr Gly Cys Ser
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 134

Gln Asp Asp Cys Glu Leu Cys Val Asn Val Ala Cys Thr Gly Cys Ser
1               5                   10                  15

<210> SEQ ID NO 135
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 135

Gln Asp Glu Cys Glu Leu Cys Val Asn Val Ala Cys Thr Gly Cys Ser
1               5                   10                  15

<210> SEQ ID NO 136
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 136

Gln Glu Asp Cys Glu Leu Cys Val Asn Val Ala Cys Thr Gly Cys Ser
1               5                   10                  15

<210> SEQ ID NO 137
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 137

Gln Glu Glu Cys Glu Leu Cys Val Asn Val Ala Cys Thr Gly Cys Ser
1               5                   10                  15
```

<210> SEQ ID NO 138
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 138

Lys Asp Asp Cys Glu Leu Cys Val Asn Val Ala Cys Thr Gly Cys Ser
1               5                   10                  15

<210> SEQ ID NO 139
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 139

Lys Asp Glu Cys Glu Leu Cys Val Asn Val Ala Cys Thr Gly Cys Ser
1               5                   10                  15

<210> SEQ ID NO 140
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 140

Lys Glu Asp Cys Glu Leu Cys Val Asn Val Ala Cys Thr Gly Cys Ser
1               5                   10                  15

<210> SEQ ID NO 141
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 141

Lys Glu Glu Cys Glu Leu Cys Val Asn Val Ala Cys Thr Gly Cys Ser
1               5                   10                  15

<210> SEQ ID NO 142
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 142

Glu Asp Asp Cys Glu Leu Cys Ile Asn Met Ala Cys Thr Gly Cys Leu
1               5                   10                  15

<210> SEQ ID NO 143
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 143

Glu Asp Glu Cys Glu Leu Cys Ile Asn Met Ala Cys Thr Gly Cys Leu
1               5                   10                  15

<210> SEQ ID NO 144
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 144

Glu Glu Asp Cys Glu Leu Cys Ile Asn Met Ala Cys Thr Gly Cys Leu
1               5                   10                  15

<210> SEQ ID NO 145
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 145

Glu Glu Glu Cys Glu Leu Cys Ile Asn Met Ala Cys Thr Gly Cys Leu
1               5                   10                  15

<210> SEQ ID NO 146
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 146

Asp Asp Asp Cys Glu Leu Cys Ile Asn Met Ala Cys Thr Gly Cys Leu
1               5                   10                  15

<210> SEQ ID NO 147
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 147

Asp Asp Glu Cys Glu Leu Cys Ile Asn Met Ala Cys Thr Gly Cys Leu
1               5                   10                  15

<210> SEQ ID NO 148
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 148

Asp Glu Asp Cys Glu Leu Cys Ile Asn Met Ala Cys Thr Gly Cys Leu
1               5                   10                  15

<210> SEQ ID NO 149
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 149

Asp Glu Glu Cys Glu Leu Cys Ile Asn Met Ala Cys Thr Gly Cys Leu
1               5                   10                  15

```
<210> SEQ ID NO 150
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 150

Gln Asp Asp Cys Glu Leu Cys Ile Asn Met Ala Cys Thr Gly Cys Leu
1               5                   10                  15

<210> SEQ ID NO 151
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 151

Gln Asp Glu Cys Glu Leu Cys Ile Asn Met Ala Cys Thr Gly Cys Leu
1               5                   10                  15

<210> SEQ ID NO 152
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 152

Gln Glu Asp Cys Glu Leu Cys Ile Asn Met Ala Cys Thr Gly Cys Leu
1               5                   10                  15

<210> SEQ ID NO 153
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 153

Gln Glu Glu Cys Glu Leu Cys Ile Asn Met Ala Cys Thr Gly Cys Leu
1               5                   10                  15

<210> SEQ ID NO 154
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 154

Lys Asp Asp Cys Glu Leu Cys Ile Asn Met Ala Cys Thr Gly Cys Leu
1               5                   10                  15

<210> SEQ ID NO 155
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 155

Lys Asp Glu Cys Glu Leu Cys Ile Asn Met Ala Cys Thr Gly Cys Leu
1               5                   10                  15

<210> SEQ ID NO 156
```

<211> LENGTH: 16
<212> TYPE: PRT
<213> ORGANISM: Artificial Sequence
<220> FEATURE:
<223> OTHER INFORMATION: Chemically Synthesized

<400> SEQUENCE: 156

Lys Glu Asp Cys Glu Leu Cys Ile Asn Met Ala Cys Thr Gly Cys Leu
1               5                   10                  15

<210> SEQ ID NO 157
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 157

Lys Glu Glu Cys Glu Leu Cys Ile Asn Met Ala Cys Thr Gly Cys Leu
1               5                   10                  15

<210> SEQ ID NO 158
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 158

Glu Asp Asp Cys Glu Leu Cys Ile Asn Met Ala Cys Thr Gly Cys Ser
1               5                   10                  15

<210> SEQ ID NO 159
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 159

Glu Asp Glu Cys Glu Leu Cys Ile Asn Met Ala Cys Thr Gly Cys Ser
1               5                   10                  15

<210> SEQ ID NO 160
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 160

Glu Glu Asp Cys Glu Leu Cys Ile Asn Met Ala Cys Thr Gly Cys Ser
1               5                   10                  15

<210> SEQ ID NO 161
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 161

Glu Glu Glu Cys Glu Leu Cys Ile Asn Met Ala Cys Thr Gly Cys Ser
1               5                   10                  15

<210> SEQ ID NO 162
<211> LENGTH: 16

```
<212> TYPE: PRT
<213> ORGANISM: Artificial Sequence
<220> FEATURE:
<223> OTHER INFORMATION: Chemically Synthesized

<400> SEQUENCE: 162

Asp Asp Asp Cys Glu Leu Cys Ile Asn Met Ala Cys Thr Gly Cys Ser
1               5                   10                  15

<210> SEQ ID NO 163
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 163

Asp Asp Glu Cys Glu Leu Cys Ile Asn Met Ala Cys Thr Gly Cys Ser
1               5                   10                  15

<210> SEQ ID NO 164
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 164

Asp Glu Asp Cys Glu Leu Cys Ile Asn Met Ala Cys Thr Gly Cys Ser
1               5                   10                  15

<210> SEQ ID NO 165
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 165

Asp Glu Glu Cys Glu Leu Cys Ile Asn Met Ala Cys Thr Gly Cys Ser
1               5                   10                  15

<210> SEQ ID NO 166
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 166

Gln Asp Asp Cys Glu Leu Cys Ile Asn Met Ala Cys Thr Gly Cys Ser
1               5                   10                  15

<210> SEQ ID NO 167
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 167

Gln Asp Glu Cys Glu Leu Cys Ile Asn Met Ala Cys Thr Gly Cys Ser
1               5                   10                  15

<210> SEQ ID NO 168
<211> LENGTH: 16
<212> TYPE: PRT
```

<213> ORGANISM: Artificial Sequence
<220> FEATURE:
<223> OTHER INFORMATION: Chemically Synthesized

<400> SEQUENCE: 168

Gln Glu Asp Cys Glu Leu Cys Ile Asn Met Ala Cys Thr Gly Cys Ser
1               5                   10                  15

<210> SEQ ID NO 169
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 169

Gln Glu Glu Cys Glu Leu Cys Ile Asn Met Ala Cys Thr Gly Cys Ser
1               5                   10                  15

<210> SEQ ID NO 170
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 170

Lys Asp Asp Cys Glu Leu Cys Ile Asn Met Ala Cys Thr Gly Cys Ser
1               5                   10                  15

<210> SEQ ID NO 171
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 171

Lys Asp Glu Cys Glu Leu Cys Ile Asn Met Ala Cys Thr Gly Cys Ser
1               5                   10                  15

<210> SEQ ID NO 172
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 172

Lys Glu Asp Cys Glu Leu Cys Ile Asn Met Ala Cys Thr Gly Cys Ser
1               5                   10                  15

<210> SEQ ID NO 173
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 173

Lys Glu Glu Cys Glu Leu Cys Ile Asn Met Ala Cys Thr Gly Cys Ser
1               5                   10                  15

<210> SEQ ID NO 174
<211> LENGTH: 15
<212> TYPE: PRT
<213> ORGANISM: Artificial Sequence

```
<220> FEATURE:
<223> OTHER INFORMATION: Chemically Synthesized
<220> FEATURE:
<221> NAME/KEY: MISC_FEATURE
<222> LOCATION: (1)..(3)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (4)..(4)
<223> OTHER INFORMATION: wherein XAA is a cysteine, penicillamine,
      homocysteine, or 3-mercaptoproline
<220> FEATURE:
<221> NAME/KEY: MISC_FEATURE
<222> LOCATION: (5)..(6)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (7)..(7)
<223> OTHER INFORMATION: wherein XAA is a cysteine, penicillamine,
      homocysteine, or 3-mercaptoproline
<220> FEATURE:
<221> NAME/KEY: MISC_FEATURE
<222> LOCATION: (8)..(11)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (12)..(12)
<223> OTHER INFORMATION: wherein XAA is a cysteine, penicillamine,
      homocysteine, or 3-mercaptoproline
<220> FEATURE:
<221> NAME/KEY: MISC_FEATURE
<222> LOCATION: (13)..(14)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (15)..(15)
<223> OTHER INFORMATION: wherein XAA is a cysteine, penicillamine,
      homocysteine, or 3-mercaptoproline

<400> SEQUENCE: 174

Xaa Xaa Xaa Xaa Xaa Xaa Xaa Xaa Xaa Xaa Xaa Xaa Xaa Xaa Xaa
1               5                   10                  15

<210> SEQ ID NO 175
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 175

Ser His Thr Cys Glu Ile Cys Ala Phe Ala Ala Cys Ala Gly Cys
1               5                   10                  15

<210> SEQ ID NO 176
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 176

Ser His Thr Cys Glu Ile Cys Ala Asn Ala Ala Cys Ala Gly Cys
1               5                   10                  15

<210> SEQ ID NO 177
<211> LENGTH: 15
<212> TYPE: PRT
<213> ORGANISM: Artificial Sequence
```

```
<220> FEATURE:
<223> OTHER INFORMATION: Chemically Synthesized

<400> SEQUENCE: 177

Ser His Thr Cys Glu Leu Cys Ala Asn Ala Ala Cys Ala Gly Cys
1               5                   10                  15

<210> SEQ ID NO 178
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 178

Ser His Thr Cys Glu Val Cys Ala Asn Ala Ala Cys Ala Gly Cys
1               5                   10                  15

<210> SEQ ID NO 179
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 179

Ser His Thr Cys Glu Tyr Cys Ala Asn Ala Ala Cys Ala Gly Cys
1               5                   10                  15

<210> SEQ ID NO 180
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 180

Ser His Thr Cys Glu Ile Cys Ala Asn Ala Ala Cys Ala Gly Cys
1               5                   10                  15

<210> SEQ ID NO 181
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 181

Ser His Thr Cys Glu Leu Cys Ala Asn Ala Ala Cys Ala Gly Cys
1               5                   10                  15

<210> SEQ ID NO 182
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 182

Ser His Thr Cys Glu Val Cys Ala Asn Ala Ala Cys Ala Gly Cys
1               5                   10                  15

<210> SEQ ID NO 183
<211> LENGTH: 15
<212> TYPE: PRT
<213> ORGANISM: Artificial Sequence
<220> FEATURE:
```

<223> OTHER INFORMATION: Chemically Synthesized

<400> SEQUENCE: 183

Ser His Thr Cys Glu Tyr Cys Ala Asn Ala Ala Cys Ala Gly Cys
1               5                   10                  15

<210> SEQ ID NO 184
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 184

Ser His Thr Cys Glu Ile Cys Ala Asn Ala Ala Cys Ala Gly Cys
1               5                   10                  15

<210> SEQ ID NO 185
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 185

Ser His Thr Cys Glu Leu Cys Ala Asn Ala Ala Cys Ala Gly Cys
1               5                   10                  15

<210> SEQ ID NO 186
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 186

Ser His Thr Cys Glu Val Cys Ala Asn Ala Ala Cys Ala Gly Cys
1               5                   10                  15

<210> SEQ ID NO 187
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 187

Ser His Thr Cys Glu Tyr Cys Ala Asn Ala Ala Cys Ala Gly Cys
1               5                   10                  15

<210> SEQ ID NO 188
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 188

Ser His Thr Cys Glu Ile Cys Ala Asn Ala Ala Cys Ala Gly Cys
1               5                   10                  15

<210> SEQ ID NO 189
<211> LENGTH: 15
<212> TYPE: PRT
<213> ORGANISM: Artificial Sequence
<220> FEATURE:
<223> OTHER INFORMATION: Chemically Synthesized

```
<400> SEQUENCE: 189

Ser His Thr Cys Glu Leu Cys Ala Asn Ala Ala Cys Ala Gly Cys
1               5                   10                  15

<210> SEQ ID NO 190
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 190

Ser His Thr Cys Glu Val Cys Ala Asn Ala Ala Cys Ala Gly Cys
1               5                   10                  15

<210> SEQ ID NO 191
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 191

Ser His Thr Cys Glu Tyr Cys Ala Asn Ala Ala Cys Ala Gly Cys
1               5                   10                  15

<210> SEQ ID NO 192
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 192

Asn Asp Glu Cys Glu Ile Cys Ala Asn Ala Ala Cys Ala Gly Cys
1               5                   10                  15

<210> SEQ ID NO 193
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 193

Asn Asp Glu Cys Glu Leu Cys Ala Asn Ala Ala Cys Ala Gly Cys
1               5                   10                  15

<210> SEQ ID NO 194
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 194

Asn Asp Glu Cys Glu Val Cys Ala Asn Ala Ala Cys Ala Gly Cys
1               5                   10                  15

<210> SEQ ID NO 195
<211> LENGTH: 15
<212> TYPE: PRT
<213> ORGANISM: Artificial Sequence
<220> FEATURE:
<223> OTHER INFORMATION: Chemically Synthesized
```

```
<400> SEQUENCE: 195

Asn Asp Glu Cys Glu Tyr Cys Ala Asn Ala Ala Cys Ala Gly Cys
1               5                   10                  15

<210> SEQ ID NO 196
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 196

Asn Asp Glu Cys Glu Ile Cys Ala Asn Ala Ala Cys Ala Gly Cys
1               5                   10                  15

<210> SEQ ID NO 197
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 197

Asn Asp Glu Cys Glu Leu Cys Ala Asn Ala Ala Cys Ala Gly Cys
1               5                   10                  15

<210> SEQ ID NO 198
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 198

Asn Asp Glu Cys Glu Val Cys Ala Asn Ala Ala Cys Ala Gly Cys
1               5                   10                  15

<210> SEQ ID NO 199
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 199

Asn Asp Glu Cys Glu Tyr Cys Ala Asn Ala Ala Cys Ala Gly Cys
1               5                   10                  15

<210> SEQ ID NO 200
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 200

Asn Asp Glu Cys Glu Ile Cys Ala Asn Ala Ala Cys Ala Gly Cys
1               5                   10                  15

<210> SEQ ID NO 201
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 201
```

Asn Asp Glu Cys Glu Leu Cys Ala Asn Ala Ala Cys Ala Gly Cys
1               5                   10                  15

<210> SEQ ID NO 202
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 202

Asn Asp Glu Cys Glu Val Cys Ala Asn Ala Ala Cys Ala Gly Cys
1               5                   10                  15

<210> SEQ ID NO 203
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 203

Asn Asp Glu Cys Glu Tyr Cys Ala Asn Ala Ala Cys Ala Gly Cys
1               5                   10                  15

<210> SEQ ID NO 204
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 204

Asn Asp Glu Cys Glu Ile Cys Ala Asn Ala Ala Cys Ala Gly Cys
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 205

Asn Asp Glu Cys Glu Leu Cys Ala Asn Ala Ala Cys Ala Gly Cys
1               5                   10                  15

<210> SEQ ID NO 206
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 206

Asn Asp Glu Cys Glu Val Cys Ala Asn Ala Ala Cys Ala Gly Cys
1               5                   10                  15

<210> SEQ ID NO 207
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 207

Asn Asp Glu Cys Glu Tyr Cys Ala Asn Ala Ala Cys Ala Gly Cys
1               5                   10                  15

<210> SEQ ID NO 208
<211> LENGTH: 17
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(3)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (4)..(4)
<223> OTHER INFORMATION: wherein XAA is a cysteine, penicillamine,
      homocysteine, or 3-mercaptoproline
<220> FEATURE:
<221> NAME/KEY: MISC_FEATURE
<222> LOCATION: (5)..(6)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (7)..(7)
<223> OTHER INFORMATION: wherein XAA is a cysteine, penicillamine,
      homocysteine, or 3-mercaptoproline
<220> FEATURE:
<221> NAME/KEY: MISC_FEATURE
<222> LOCATION: (8)..(11)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (12)..(12)
<223> OTHER INFORMATION: wherein XAA is a cysteine, penicillamine,
      homocysteine, or 3-mercaptoproline
<220> FEATURE:
<221> NAME/KEY: MISC_FEATURE
<222> LOCATION: (13)..(14)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (15)..(15)
<223> OTHER INFORMATION: XAA is none or a natural, unnatural, analogue,
      L, D, or methylated amino acid or any combination
<220> FEATURE:
<221> NAME/KEY: MISC_FEATURE
<222> LOCATION: (16)..(16)
<223> OTHER INFORMATION: XAA is none or a natural, unnatural, analogue,
      L, D, or methylated amino acid or any combination
<220> FEATURE:
<221> NAME/KEY: MISC_FEATURE
<222> LOCATION: (17)..(17)
<223> OTHER INFORMATION: XAA is any natural, unnatural, analogue, L, D,
      or methylated amino acid or any combination

<400> SEQUENCE: 208

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 209
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 209

Gln Glu Glu Cys Glu Leu Cys Ile Asn Met Ala Cys Thr Gly Tyr

```
1               5                   10                  15

<210> SEQ ID NO 210
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 210

Gln Glu Glu Cys Glu Thr Cys Ile Asn Met Ala Cys Thr Gly Tyr
1               5                   10                  15

<210> SEQ ID NO 211
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 211

Gln Asp Glu Cys Glu Thr Cys Ile Asn Met Ala Cys Thr Gly Tyr
1               5                   10                  15

<210> SEQ ID NO 212
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 212

Gln Asp Asp Cys Glu Thr Cys Ile Asn Met Ala Cys Thr Gly Tyr
1               5                   10                  15

<210> SEQ ID NO 213
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 213

Gln Glu Asp Cys Glu Thr Cys Ile Asn Met Ala Cys Thr Gly Tyr
1               5                   10                  15

<210> SEQ ID NO 214
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 214

Gln Glu Glu Cys Glu Glu Cys Ile Asn Met Ala Cys Thr Gly Tyr
1               5                   10                  15

<210> SEQ ID NO 215
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 215

Gln Asp Glu Cys Glu Glu Cys Ile Asn Met Ala Cys Thr Gly Tyr
1               5                   10                  15
```

<210> SEQ ID NO 216
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 216

Gln Asp Asp Cys Glu Glu Cys Ile Asn Met Ala Cys Thr Gly Tyr
1               5                   10                  15

<210> SEQ ID NO 217
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 217

Gln Glu Asp Cys Glu Glu Cys Ile Asn Met Ala Cys Thr Gly Tyr
1               5                   10                  15

<210> SEQ ID NO 218
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 218

Gln Glu Glu Cys Glu Tyr Cys Ile Asn Met Ala Cys Thr Gly Tyr
1               5                   10                  15

<210> SEQ ID NO 219
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 219

Gln Asp Glu Cys Glu Tyr Cys Ile Asn Met Ala Cys Thr Gly Tyr
1               5                   10                  15

<210> SEQ ID NO 220
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 220

Gln Asp Asp Cys Glu Tyr Cys Ile Asn Met Ala Cys Thr Gly Tyr
1               5                   10                  15

<210> SEQ ID NO 221
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 221

Gln Glu Asp Cys Glu Tyr Cys Ile Asn Met Ala Cys Thr Gly Tyr
1               5                   10                  15

```
<210> SEQ ID NO 222
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 222

Gln Glu Glu Cys Glu Ile Cys Ile Asn Met Ala Cys Thr Gly Tyr
1               5                   10                  15

<210> SEQ ID NO 223
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 223

Gln Asp Glu Cys Glu Ile Cys Ile Asn Met Ala Cys Thr Gly Tyr
1               5                   10                  15

<210> SEQ ID NO 224
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 224

Gln Asp Asp Cys Glu Ile Cys Ile Asn Met Ala Cys Thr Gly Tyr
1               5                   10                  15

<210> SEQ ID NO 225
<211> LENGTH: 15
<212> TYPE: PRT
<213> ORGANISM: Artificial Sequence
<220> FEATURE:
<223> OTHER INFORMATION: Chemically Synthesized

<400> SEQUENCE: 225

Gln Glu Asp Cys Glu Ile Cys Ile Asn Met Ala Cys Thr Gly Tyr
1               5                   10                  15

<210> SEQ ID NO 226
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 226

Gln Glu Glu Cys Glu Thr Cys Ile Asn Met Ala Cys Thr Gly Cys Ser
1               5                   10                  15

<210> SEQ ID NO 227
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 227

Gln Asp Glu Cys Glu Thr Cys Ile Asn Met Ala Cys Thr Gly Cys Ser
1               5                   10                  15
```

```
<210> SEQ ID NO 228
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 228

Gln Asp Asp Cys Glu Thr Cys Ile Asn Met Ala Cys Thr Gly Cys Ser
1               5                   10                  15

<210> SEQ ID NO 229
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 229

Gln Glu Asp Cys Glu Thr Cys Ile Asn Met Ala Cys Thr Gly Cys Ser
1               5                   10                  15

<210> SEQ ID NO 230
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 230

Gln Glu Glu Cys Glu Glu Cys Ile Asn Met Ala Cys Thr Gly Cys Ser
1               5                   10                  15

<210> SEQ ID NO 231
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 231

Gln Asp Glu Cys Glu Glu Cys Ile Asn Met Ala Cys Thr Gly Cys Ser
1               5                   10                  15

<210> SEQ ID NO 232
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 232

Gln Asp Asp Cys Glu Glu Cys Ile Asn Met Ala Cys Thr Gly Cys Ser
1               5                   10                  15

<210> SEQ ID NO 233
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 233

Gln Glu Asp Cys Glu Glu Cys Ile Asn Met Ala Cys Thr Gly Cys Ser
1               5                   10                  15

<210> SEQ ID NO 234
```

```
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 234

Gln Glu Glu Cys Glu Tyr Cys Ile Asn Met Ala Cys Thr Gly Cys Ser
1               5                   10                  15

<210> SEQ ID NO 235
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 235

Gln Asp Glu Cys Glu Tyr Cys Ile Asn Met Ala Cys Thr Gly Cys Ser
1               5                   10                  15

<210> SEQ ID NO 236
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 236

Gln Asp Asp Cys Glu Tyr Cys Ile Asn Met Ala Cys Thr Gly Cys Ser
1               5                   10                  15

<210> SEQ ID NO 237
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 237

Gln Glu Asp Cys Glu Tyr Cys Ile Asn Met Ala Cys Thr Gly Cys Ser
1               5                   10                  15

<210> SEQ ID NO 238
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 238

Gln Glu Glu Cys Glu Ile Cys Ile Asn Met Ala Cys Thr Gly Cys Ser
1               5                   10                  15

<210> SEQ ID NO 239
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 239

Gln Asp Glu Cys Glu Ile Cys Ile Asn Met Ala Cys Thr Gly Cys Ser
1               5                   10                  15

<210> SEQ ID NO 240
<211> LENGTH: 16
```

```
<212> TYPE: PRT
<213> ORGANISM: Artificial Sequence
<220> FEATURE:
<223> OTHER INFORMATION: Chemically Synthesized

<400> SEQUENCE: 240

Gln Asp Asp Cys Glu Ile Cys Ile Asn Met Ala Cys Thr Gly Cys Ser
1               5                   10                  15

<210> SEQ ID NO 241
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 241

Gln Glu Asp Cys Glu Ile Cys Ile Asn Met Ala Cys Thr Gly Cys Ser
1               5                   10                  15

<210> SEQ ID NO 242
<211> LENGTH: 22
<212> TYPE: PRT
<213> ORGANISM: Artificial Sequence
<220> FEATURE:
<223> OTHER INFORMATION: Chemically Synthesized

<400> SEQUENCE: 242

Asn Ser Ser Asn Ser Ser Asn Tyr Cys Cys Glu Lys Cys Cys Asn Pro
1               5                   10                  15

Ala Cys Thr Gly Cys Tyr
            20

<210> SEQ ID NO 243
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is attached to polyethylene glycol
<220> FEATURE:
<221> NAME/KEY: MISC_FEATURE
<222> LOCATION: (16)..(16)
<223> OTHER INFORMATION: wherein TYR is attached to polyethylene glycol

<400> SEQUENCE: 243

Asn Phe Cys Cys Glu Thr Cys Cys Asn Pro Ala Cys Thr Gly Cys Tyr
1               5                   10                  15

<210> SEQ ID NO 244
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is attached to polyethylene glycol

<400> SEQUENCE: 244

Asn Phe Cys Cys Glu Thr Cys Cys Asn Pro Ala Cys Thr Gly Cys Tyr
1               5                   10                  15

<210> SEQ ID NO 245
```

```
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein TYR is attached to polyethylene glycol

<400> SEQUENCE: 245

Asn Phe Cys Cys Glu Thr Cys Cys Asn Pro Ala Cys Thr Gly Cys Tyr
1               5                   10                  15

<210> SEQ ID NO 246
<211> LENGTH: 16
<212> TYPE: PRT
<213> ORGANISM: Artificial Sequence
<220> FEATURE:
<223> OTHER INFORMATION: Chemically Synthesized

<400> SEQUENCE: 246

Asn Phe Cys Cys Glu Tyr Cys Cys Asn Pro Ala Cys Thr Gly Cys Tyr
1               5                   10                  15

<210> SEQ ID NO 247
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (16)..(16)
<223> OTHER INFORMATION: wherein TYR is a D amino acid

<400> SEQUENCE: 247

Asn Phe Cys Cys Glu Tyr Cys Cys Asn Pro Ala Cys Thr Gly Cys Tyr
1               5                   10                  15

<210> SEQ ID NO 248
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (16)..(16)
<223> OTHER INFORMATION: wherein TYR is a D amino acid

<400> SEQUENCE: 248

Asn Phe Cys Cys Glu Tyr Cys Cys Asn Pro Ala Cys Thr Gly Cys Tyr
1               5                   10                  15

<210> SEQ ID NO 249
<211> LENGTH: 16
<212> TYPE: PRT
<213> ORGANISM: Artificial Sequence
<220> FEATURE:
<223> OTHER INFORMATION: Chemically Synthesized
<220> FEATURE:
<221> NAME/KEY: MISC_FEATURE
<222> LOCATION: (1)..(1)
<223> OTHER INFORMATION: wherein ASN is a D amino acid

<400> SEQUENCE: 249
```

-continued

Asn Phe Cys Cys Glu Tyr Cys Cys Asn Pro Ala Cys Thr Gly Cys Tyr
1               5                   10                  15

<210> SEQ ID NO 250
<211> LENGTH: 16
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(2)
<223> OTHER INFORMATION: wherein XAA is absent or any natural, unnatural
      amino acid or analogue thereof
<220> FEATURE:
<221> NAME/KEY: MISC_FEATURE
<222> LOCATION: (3)..(3)
<223> OTHER INFORMATION: wherein XAA is any natural, unnatural amino
      acid or analogue thereof
<220> FEATURE:
<221> NAME/KEY: MISC_FEATURE
<222> LOCATION: (5)..(11)
<223> OTHER INFORMATION: wherein XAA is any natural, unnatural amino
      acid or analogue thereof
<220> FEATURE:
<221> NAME/KEY: MISC_FEATURE
<222> LOCATION: (13)..(15)
<223> OTHER INFORMATION: wherein XAA is any natural, unnatural amino
      acid or analogue thereof
<220> FEATURE:
<221> NAME/KEY: MISC_FEATURE
<222> LOCATION: (16)..(16)
<223> OTHER INFORMATION: wherein XAA is absent or any natural, unnatural
      amino acid or analogue thereof

<400> SEQUENCE: 250

Xaa Xaa Xaa Cys Xaa Xaa Xaa Xaa Xaa Xaa Xaa Cys Xaa Xaa Xaa Xaa
1               5                   10                  15

<210> SEQ ID NO 251
<211> LENGTH: 16
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: wherein XAA is a pyroglutamic acid

<400> SEQUENCE: 251

Xaa Asp Glu Cys Glu Leu Cys Val Asn Val Ala Cys Thr Gly Cys Leu
1               5                   10                  15

<210> SEQ ID NO 252
<211> LENGTH: 15
<212> TYPE: PRT
<213> ORGANISM: Homo sapiens

<400> SEQUENCE: 252

Pro Gly Thr Cys Glu Ile Cys Ala Tyr Ala Ala Cys Thr Gly Cys
1               5                   10                  15

<210> SEQ ID NO 253
<211> LENGTH: 16
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE

```
<222> LOCATION: (1)..(1)
<223> OTHER INFORMATION: wherein ASN is a D amino acid
<220> FEATURE:
<221> NAME/KEY: MISC_FEATURE
<222> LOCATION: (3)..(3)
<223> OTHER INFORMATION: wherein XAA is alpha-aminoadipic acid
<220> FEATURE:
<221> NAME/KEY: MISC_FEATURE
<222> LOCATION: (16)..(16)
<223> OTHER INFORMATION: wherein LEU is a D amino acid

<400> SEQUENCE: 253

Asn Asp Xaa Cys Glu Leu Cys Val Asn Val Ala Cys Thr Gly Cys Leu
1               5                   10                  15

<210> SEQ ID NO 254
<211> LENGTH: 16
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: wherein XAA is a pyroglutamic acid
<220> FEATURE:
<221> NAME/KEY: MISC_FEATURE
<222> LOCATION: (3)..(3)
<223> OTHER INFORMATION: wherein XAA is alpha-aminoadipic acid
<220> FEATURE:
<221> NAME/KEY: MISC_FEATURE
<222> LOCATION: (16)..(16)
<223> OTHER INFORMATION: wherein LEU is a D amino acid
<220> FEATURE:
<221> NAME/KEY: MISC_FEATURE
<222> LOCATION: (16)..(16)
<223> OTHER INFORMATION: wherein LEU is conjugated to an AMIDE

<400> SEQUENCE: 254

Xaa Asp Xaa Cys Glu Leu Cys Val Asn Val Ala Cys Thr Gly Cys Leu
1               5                   10                  15

<210> SEQ ID NO 255
<211> LENGTH: 16
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (3)..(3)
<223> OTHER INFORMATION: wherein XAA is alpha-aminoadipic acid
<220> FEATURE:
<221> NAME/KEY: MISC_FEATURE
<222> LOCATION: (16)..(16)
<223> OTHER INFORMATION: wherein SER is a D amino acid

<400> SEQUENCE: 255
```

Asn Asp Xaa Cys Glu Leu Cys Val Asn Val Ala Cys Thr Gly Cys Ser
1               5                   10                  15

<210> SEQ ID NO 256
<211> LENGTH: 16
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: wherein ASN is a D amino acid
<220> FEATURE:
<221> NAME/KEY: MISC_FEATURE
<222> LOCATION: (3)..(3)
<223> OTHER INFORMATION: wherein XAA is alpha-aminoadipic acid
<220> FEATURE:
<221> NAME/KEY: MISC_FEATURE
<222> LOCATION: (16)..(16)
<223> OTHER INFORMATION: wherein Tyr is a D amino acid

<400> SEQUENCE: 256

Asn Asp Xaa Cys Glu Leu Cys Val Asn Val Ala Cys Thr Gly Cys Tyr
1               5                   10                  15

<210> SEQ ID NO 257
<211> LENGTH: 16
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: XAA is none or a natural, unnatural or an
      analogue amino acid, may be L, D, or a methylated amino acid, or
      any combination
<220> FEATURE:
<221> NAME/KEY: MISC_FEATURE
<222> LOCATION: (2)..(2)
<223> OTHER INFORMATION: XAA is none or a natural, unnatural or an
      analogue amino acid, may be L, D, or a methylated amino acid, or
      any combination
<220> FEATURE:
<221> NAME/KEY: MISC_FEATURE
<222> LOCATION: (3)..(3)
<223> OTHER INFORMATION: XAA is any natural, unnatural or an analogue
      amino acid, may be L, D, or a methylated amino acid, or any
      combination
<220> FEATURE:
<221> NAME/KEY: MISC_FEATURE
<222> LOCATION: (5)..(11)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (13)..(15)
<223> OTHER INFORMATION: XAA is natural, unnatural, analogue, L, D, or
      methylated amino acid or any combination
<220> FEATURE:
<221> NAME/KEY: MISC_FEATURE
<222> LOCATION: (16)..(16)
<223> OTHER INFORMATION: XAA is none or one natural, unnatural or an
      analogue amino acid, may be L, D, or a methylated amino acid, or
      any combination

<400> SEQUENCE: 257

Xaa Xaa Xaa Cys Xaa Xaa Xaa Xaa Xaa Xaa Xaa Cys Xaa Xaa Xaa Xaa
1               5                   10                  15

<210> SEQ ID NO 258
<211> LENGTH: 16

```
<212> TYPE: PRT
<213> ORGANISM: Artificial Sequence
<220> FEATURE:
<223> OTHER INFORMATION: Chemically synthesized
<220> FEATURE:
<221> NAME/KEY: MISC_FEATURE
<222> LOCATION: (3)..(3)
<223> OTHER INFORMATION: wherein XAA is alpha-aminoadipic acid

<400> SEQUENCE: 258

Asn Asp Xaa Cys Glu Leu Cys Val Asn Val Ala Cys Thr Gly Cys Leu
1               5                   10                  15
```